(12) United States Patent
Fan et al.

(10) Patent No.: US 10,783,632 B2
(45) Date of Patent: Sep. 22, 2020

(54) MACHINE LEARNING SYSTEMS AND METHOD FOR ASSESSMENT, HEALING PREDICTION, AND TREATMENT OF WOUNDS

(71) Applicant: SPECTRAL MD, INC., Dallas, TX (US)

(72) Inventors: Wensheng Fan, Plano, TX (US); John Michael DiMaio, Dallas, TX (US); Jeffrey E. Thatcher, Irving, TX (US); Peiran Quan, Dallas, TX (US); Faliu Yi, Allen, TX (US); Kevin Plant, Dallas, TX (US); Ronald Baxter, Grand Prairie, TX (US); Brian McCall, Dallas, TX (US); Zhicun Gao, Plano, TX (US); Jason Dwight, Dallas, TX (US)

(73) Assignee: SPECTRAL MD, INC., Dallas, TX (US)

(*) Notice: Subject to any disclaimer, the term of this patent is extended or adjusted under 35 U.S.C. 154(b) by 0 days.

(21) Appl. No.: 16/738,911

(22) Filed: Jan. 9, 2020

(65) Prior Publication Data
US 2020/0193597 A1    Jun. 18, 2020

Related U.S. Application Data

(63) Continuation of application No. PCT/US2019/065820, filed on Dec. 11, 2019.
(Continued)

(51) Int. Cl.
*G06K 9/00* (2006.01)
*G06K 9/62* (2006.01)
(Continued)

(52) U.S. Cl.
CPC ............ *G06T 7/0012* (2013.01); *A61B 5/445* (2013.01); *A61B 5/7275* (2013.01); *G06T 7/11* (2017.01);
(Continued)

(58) Field of Classification Search
USPC .................. 382/128, 190, 155; 600/306, 476
See application file for complete search history.

(56) References Cited

U.S. PATENT DOCUMENTS

| 4,170,987 A | 10/1979 | Anselmo et al. |
| 5,074,306 A | 12/1991 | Green et al. |

(Continued)

FOREIGN PATENT DOCUMENTS

| CA | 2287687 | 5/2000 |
| CN | 1543325 | 11/2004 |

(Continued)

OTHER PUBLICATIONS

2011 National Burn Repository: Report of Data from 2001-2010. American Burn Association (2011) pp. 134.
(Continued)

*Primary Examiner* — Kathleen Y Dulaney
(74) *Attorney, Agent, or Firm* — Knobbe Martens Olson & Bear, LLP

(57) ABSTRACT

Machine learning systems and methods are disclosed for prediction of wound healing, such as for diabetic foot ulcers or other wounds, and for assessment implementations such as segmentation of images into wound regions and non-wound regions. Systems for assessing or predicting wound healing can include a light detection element configured to collect light of at least a first wavelength reflected from a tissue region including a wound, and one or more processors configured to generate an image based on a signal from the light detection element having pixels depicting the tissue
(Continued)

region, determine reflectance intensity values for at least a subset of the pixels, determine one or more quantitative features of the subset of the plurality of pixels based on the reflectance intensity values, and generate a predicted or assessed healing parameter associated with the wound over a predetermined time interval.

20 Claims, 39 Drawing Sheets

Related U.S. Application Data

(60) Provisional application No. 62/780,854, filed on Dec. 17, 2018, provisional application No. 62/780,121, filed on Dec. 14, 2018, provisional application No. 62/818,375, filed on Mar. 14, 2019.

(51) Int. Cl.
| | |
|---|---|
| G06K 9/46 | (2006.01) |
| A61B 5/00 | (2006.01) |
| A61B 6/00 | (2006.01) |
| G06T 7/00 | (2017.01) |
| G06T 7/11 | (2017.01) |
| G16H 30/40 | (2018.01) |
| G16H 50/30 | (2018.01) |

(52) U.S. Cl.
CPC .......... *G16H 30/40* (2018.01); *G16H 50/30* (2018.01); *A61B 5/0077* (2013.01); *G06T 2207/20081* (2013.01); *G06T 2207/30088* (2013.01); *G06T 2207/30096* (2013.01)

(56) References Cited

U.S. PATENT DOCUMENTS

| | | | |
|---|---|---|---|
| 5,701,902 A | 12/1997 | Vari et al. | |
| 5,982,497 A | 11/1999 | Hopkins | |
| 6,008,889 A | 12/1999 | Zeng et al. | |
| 6,058,352 A | 5/2000 | Lu et al. | |
| 6,081,612 A | 6/2000 | Gutkowicz-Krusin et al. | |
| 6,352,517 B1 | 3/2002 | Flock et al. | |
| 6,353,753 B1 | 3/2002 | Flock et al. | |
| 6,381,488 B1 | 4/2002 | Dickey et al. | |
| 6,411,907 B1 | 6/2002 | Lu et al. | |
| 6,638,668 B2 | 10/2003 | Buchsbaum et al. | |
| 6,640,132 B1 | 10/2003 | Freeman et al. | |
| 6,889,075 B2 | 5/2005 | Marchitto et al. | |
| 7,433,042 B1 | 10/2008 | Cavanaugh et al. | |
| 7,612,822 B2 | 11/2009 | Ajito et al. | |
| 7,648,808 B2 | 1/2010 | Buchsbaum et al. | |
| 7,729,750 B2 | 6/2010 | Tromberg et al. | |
| 7,733,389 B2 | 6/2010 | Kurosawa et al. | |
| 7,835,002 B2 | 11/2010 | Muhammed et al. | |
| 7,860,554 B2 | 12/2010 | Leonardi et al. | |
| 8,081,311 B2 | 12/2011 | Themelis | |
| 8,233,148 B2 | 7/2012 | Bodkin et al. | |
| 8,488,024 B2 | 7/2013 | Yano et al. | |
| 8,509,879 B2 | 8/2013 | Durkin et al. | |
| 8,583,216 B2 | 11/2013 | Pershing et al. | |
| 8,605,172 B2 | 12/2013 | Nikkanen et al. | |
| 8,692,912 B2 | 4/2014 | Fish et al. | |
| 8,704,917 B2 | 4/2014 | Rodrigues et al. | |
| 8,812,083 B2 | 8/2014 | Papazoglou et al. | |
| 8,838,211 B2 | 9/2014 | Melendez et al. | |
| 8,892,192 B2 | 11/2014 | Cuccia et al. | |
| 9,078,619 B2 | 7/2015 | Panasyuk et al. | |
| 9,295,402 B1 | 3/2016 | Arbab et al. | |
| 9,372,118 B1 | 6/2016 | Tablin et al. | |
| 9,547,178 B2 | 1/2017 | Erdogan et al. | |
| 9,648,254 B2 | 5/2017 | Darty et al. | |
| 9,717,417 B2 | 8/2017 | DiMaio et al. | |
| 9,766,382 B2 | 9/2017 | Darty | |
| 9,962,090 B2 | 5/2018 | DiMaio et al. | |
| 10,066,997 B2 | 9/2018 | Körner et al. | |
| 2002/0016533 A1 | 2/2002 | Marchitto et al. | |
| 2006/0155193 A1 | 7/2006 | Leonardi et al. | |
| 2006/0184043 A1 | 8/2006 | Tromberg et al. | |
| 2007/0016079 A1* | 1/2007 | Freeman ................ G16H 50/20 | |
| | | | 600/476 |
| 2007/0038042 A1* | 2/2007 | Freeman ............ A61B 5/14552 | |
| | | | 600/310 |
| 2007/0232930 A1* | 10/2007 | Freeman ............ A61B 5/14551 | |
| | | | 600/476 |
| 2007/0249913 A1* | 10/2007 | Freeman ................ A61B 5/412 | |
| | | | 600/300 |
| 2008/0278602 A1 | 11/2008 | Otsu | |
| 2009/0072142 A1 | 3/2009 | Blitzer | |
| 2009/0118600 A1 | 5/2009 | Ortiz et al. | |
| 2009/0118622 A1 | 5/2009 | Durkin et al. | |
| 2009/0275808 A1 | 11/2009 | DiMaio et al. | |
| 2009/0275841 A1 | 11/2009 | Melendez et al. | |
| 2010/0042004 A1 | 2/2010 | Dhawan | |
| 2010/0210931 A1 | 8/2010 | Cuccia | |
| 2010/0292549 A1 | 11/2010 | Shuler | |
| 2011/0124987 A1 | 5/2011 | Papazoglou et al. | |
| 2011/0124988 A1 | 5/2011 | Cuccia | |
| 2011/0205052 A1 | 8/2011 | Clawson | |
| 2012/0078088 A1 | 3/2012 | Whitestone et al. | |
| 2012/0141000 A1 | 6/2012 | Jeanne et al. | |
| 2012/0172243 A1 | 7/2012 | Davicioni et al. | |
| 2012/0190944 A1 | 7/2012 | Thaveeprungsriporn et al. | |
| 2012/0200700 A1 | 8/2012 | Bennett et al. | |
| 2012/0209095 A1 | 8/2012 | Huiku | |
| 2012/0245473 A1 | 9/2012 | Mycek et al. | |
| 2012/0288230 A1 | 11/2012 | Pologe et al. | |
| 2012/0321759 A1 | 12/2012 | Marinkovich et al. | |
| 2013/0064441 A1 | 3/2013 | Kask | |
| 2013/0274612 A1 | 10/2013 | Cuccia et al. | |
| 2013/0342670 A1 | 12/2013 | Kyal et al. | |
| 2014/0012225 A1 | 1/2014 | Yoo et al. | |
| 2014/0092288 A1 | 4/2014 | Hattery et al. | |
| 2014/0128744 A1 | 5/2014 | Cuccia et al. | |
| 2014/0155757 A1 | 6/2014 | Yang et al. | |
| 2014/0155818 A1 | 6/2014 | Salinas et al. | |
| 2014/0193050 A1 | 7/2014 | Miller | |
| 2014/0213910 A1 | 7/2014 | Durkin et al. | |
| 2015/0011892 A1 | 1/2015 | Sostek | |
| 2015/0044098 A1 | 1/2015 | Smart et al. | |
| 2015/0080742 A1 | 3/2015 | Andre et al. | |
| 2015/0141839 A1 | 5/2015 | Cuccia et al. | |
| 2015/0208923 A1 | 7/2015 | Akl et al. | |
| 2015/0285685 A1 | 10/2015 | Wax et al. | |
| 2015/0369664 A1 | 12/2015 | Garsha et al. | |
| 2015/0374276 A1 | 12/2015 | Farkas et al. | |
| 2015/0374309 A1 | 12/2015 | Farkas et al. | |
| 2016/0100790 A1* | 4/2016 | Cantu .................. A61B 5/0064 | |
| | | | 600/306 |
| 2016/0321414 A1 | 11/2016 | Salganicoff et al. | |
| 2016/0345888 A1 | 12/2016 | Wu et al. | |
| 2017/0079530 A1* | 3/2017 | DiMaio ................ A61B 5/445 | |
| 2017/0084024 A1* | 3/2017 | Gurevich ............. A61B 5/7239 | |
| 2017/0150903 A1 | 6/2017 | Barnes et al. | |
| 2017/0319073 A1 | 11/2017 | DiMaio et al. | |
| 2017/0354358 A1* | 12/2017 | Rajab .................... A61B 5/444 | |
| 2017/0367580 A1* | 12/2017 | DiMaio ................ A61B 5/445 | |
| 2018/0028079 A1* | 2/2018 | Gurevich ............. A61B 5/0261 | |
| 2018/0061046 A1 | 3/2018 | Bozorgtabar et al. | |
| 2018/0184015 A1 | 6/2018 | Richarte et al. | |
| 2018/0247153 A1 | 8/2018 | Ganapati et al. | |
| 2018/0310828 A1 | 11/2018 | DiMaio et al. | |
| 2019/0277753 A1 | 9/2019 | Waxman et al. | |
| 2019/0290117 A1 | 9/2019 | Wang et al. | |
| 2020/0138360 A1 | 5/2020 | Fan et al. | |
| 2020/0193580 A1 | 6/2020 | McCall et al. | |

FOREIGN PATENT DOCUMENTS

| | | |
|---|---|---|
| CN | 1745294 | 3/2006 |
| CN | 101627902 | 1/2010 |
| CN | 102641126 | 8/2012 |

(56) References Cited

FOREIGN PATENT DOCUMENTS

| | | |
|---|---|---|
| CN | 103228205 | 7/2013 |
| CN | 103815875 | 6/2015 |
| CN | 105143448 | 12/2015 |
| CN | 103327894 | 5/2016 |
| EP | 2944930 A2 | 11/2015 |
| JP | H05-505117 | 8/1993 |
| JP | H10-505768 | 6/1998 |
| JP | 2000-139846 | 5/2000 |
| JP | 2001-503645 | 3/2001 |
| JP | 2008-525158 | 7/2008 |
| JP | 2010-043979 A | 2/2010 |
| JP | 2010-503475 | 2/2010 |
| WO | WO 2014/041543 | 3/2014 |
| WO | WO 2014/125250 | 8/2014 |
| WO | WO 2016/069788 A1 | 5/2016 |
| WO | WO 2017/053609 A1 | 3/2017 |
| WO | WO 2017/074505 | 5/2017 |
| WO | WO 2018/160963 | 9/2018 |
| WO | WO 2020/123722 | 6/2020 |
| WO | WO 2020/123724 | 6/2020 |

OTHER PUBLICATIONS

Afromowitz et al., "Clinical Evaluation of Burn Injuries Using an Optical Reflectance Technique," IEEE Transactions on Biomedical Engineering, 1987; 34(2):114-27.

Afromowitz et al., "Multispectral imaging of burn wounds: a new clinical instrument for evaluating burn depth". IEEE transactions on bio-medical engineering, 1988; 35(10):842-850.

Aldrich, John "R. A. Fisher and the Making of Maximum likelihood 1912-1922", Statistical Science, 1997; 12(3):162-176.

Alian et al., "Photoplethysmography," Best Pract. Res. Clin. Anaesthesiol., 2014; 28(4):395-406; ePub Sep. 9, 2014.

Allen, John "Photoplethysmography and its application in clinical physiological measurement.," Physiol. Meas., 2007; 28:R1-R39.

Anselmo et al., "Multispectral Photographic Analysis—A New Quantitative Tool to Assist in the Early Diagnosis of Thermal Burn Depth." Annals of Biomed Engin. 1977; 5:179-193.

Antonutto et al., "Noninvasive assessment of cardiac output from arterial pressure profiles during exercise," Eur J Appl Physiol. 1995; 72:18-24.

Arsenault et al., "The Use of Transcutaneous Oximetry to Predict Healing Complications of Lower Limb Amputations: A Systematic Review and Meta-Analysis," Eur J Vasc Endovasc Surg. 2012; 43:329-336.

Bajwa et al., "Assessment of Tissue Perfusion in the Lower Limb: Current Methods and Techniques Under Development," Circ Cardiovasc Imag. Sep. 2014; 7:836-843.

Bak et al., "Hemodynamic Changes During Resuscitation After Burns Using The Parkland Formula". J Trauma-Injury Infect Crit Care, 2009; 66(2):329-336.

Benitez et al., "Contemporary assessment of foot perfusion in patients with critical limb ischemia," Semin Vasc Surg. Mar. 2014; 27:3-15.

Branski et al., "A procine model of full-thickness burn, excision, and skin autografting," Burns 2008; 34(8):1119-1127.

Burgess et al., "Segmental Transcutaneous Measurements of PO2 in Patients Requiring Below-The-Knee Amputation for Peripheral Vascular Insufficiency," J Bone Jt Surg Am 1982; 64:378-82.

Cancio et al., "Burn Support for Operation Iraqi Freedom and related operations, 2003 to 2004", J Burn Care Rehabil. (2005) 26(2): 151-161.

CDC, Diabetes Public Health Resource, "Number (in Thousands) of Hospital Discharges for Non-Traumatic Lower Extremity Amputation with Diabetes as a Listed Diagnosis, United States, 1988-2006," Centers for Disease Control and Prevention, Oct. 20, 2016, Available at: http://www.cdc.gov/diabetes/statistics/lea/fig1.htm; 3 pages.

Cheong et al., "A Review of the Optical Properties of Biological Tissues", IEEE J Quantum Electronics; 1990; 26(12): 2166-2185.

Cortes et al., "Support-Vectors Networks," Machine Learning 1995; 20:273-297.

Cousineau et al., "Outliers detection and treatment: a review," Inter J Psycholog Res. 2010; 3(1):58-67.

Cover et al., "Nearest Neighbor Pattern Classification", IEEE Transactions on Information Theory; 1967; 13(1):21-27.

Cross et al., "Near infrared point and imaging spectroscopy for burn depth assessment", Int'l Congress Series (2005) 1281: 137-142.

Cross et al., "Clinical Utilization of Near-infrared Spectroscopy Devices for burn depth assessment", Wound Rep Reg. (2007) 15: 332-340.

Cuccia et al., "Quantitation and mapping of tissue optical properties using modulated imaging," J Biomed Opt., 2009; 14(2): 1-31.

Desai et al., "Early Burn Wound Excision Significantly Reduces Blood Loss," Ann. Surg. 1990; (6):753-62.

Dillingham et al., "Reamputation, Mortality, and Health Care Costs Among Persons with Dysvascular Lower-Limb Amputations," Arch Phys Med Rehabil. 2005; 86:480-486.

Eisenbeiss et al., "Reflection-optical multispectral imaging method for objective determination of burn depth," Burns. 1999; 25:697-704.

Eneroth, M., "Factors affecting wound healing after major amputation for vascular disease: a review," Prosth Ortho Internat. 1999; 23:195-208.

Engrav et al., "Early Excision and Grafting vs. Nonoperative Treatment of Burns of Indeterminant Depth: A Randomized Prospective Study," J of Trauma, 1983; 23(11):1001-1004.

Fischer et al., "Multispectral and Hyperspectral imaging technologies in conservation: current research and potential applications," Stud Conserv. 2006; 7: 3-16.

Franklin et al., "Cost of lower-limb amputation in US veterans with diabetes using health services data in fiscal years 2004 and 2010," J Rehabil Res Dev (JRRD) 2014; 51(8):1325-1330.

Graham et al., "Wound Healing of Cutaneous Sulfur Mustard Injuries: Strategies for the Development of Improved Therapies," J Burns and Wounds. 2005; 4:1-45.

Grubbs, Frank E., "Procedures for detection outlying observations in samples", Ballistic Research Laboratories, Aberdeen Proving Ground, 1974; BRL Report No. 1713; 53 pages.

Guo et al., "Factors Affecting Wound Healing," J Dent Res. 2010; 89(3):219-229.

Gufinkel et al., "Development of a Novel Animal Burn Model Using Radiant Heat in Rats and Swine," Acad Emerg Med. 2010; 17(5):514-520.

Gurfinkel et al., "Histological assessment of tangentially excised burn eschars," Can J Plast Surg. 2010; 18(3):e33-e36.

Guyon et al., "An Introduction to Variables and Feature Selection", J Machine Learn Res. 2003; 3:1157-1182.

HCUP Nationwide Inpatient Sample (NIS)—2009, Healthcare Cost and Utilization Project—HCUP, A Federal-State-Industry Partnership in Health Data Issued May 2011, Updated Nov. 2015, 89 pages, Retrievable at http://www.hcup-us.ahrq.gov; 89 pages.

Heimbach et al., Surgical management of the burn wound, Cover and Table of Contents, New York: Raven Press, 1984; TOC only.

Heimbach, David M., "Early Burn Excision and Grafting," Surgical Clinics of North America [Burns], 1987; 67(1):93-107.

Heredia-Juesas et al., "Non-Invasive Optical Imaging Techniques for Burn-Injured Tissue Detection for Debridement Surgery," Conf Proc IEEE/EMBS, Aug. 2016; 2893-2896.

Hu et al., "Development of Effective Photoplethysmographic Measurement Techniques: From Contact to Non-Contact and from Point to Imaging." 31st Annual International Conference of the IEEE/EMBS. 2009; 6550-6553.

HyperMed Imaging Inc., FDA-DHHS Reply to 510(k), "Hyperview Hyperspectral Tissue Oxygenation Measurement System" dated Dec. 16, 2016 with enclosures; in 15 pages.

HyperMed Medical Spectral Imaging, Product Overview "HyperView", 2017 in 4 pages.

IMEC, "Hyperspectral Imaging", downloaded from https://www.imec-int.com/en/hyperspectral-imaging on Jul. 24, 2018 in 10 pages.

(56) References Cited

OTHER PUBLICATIONS

IMMS et al., "A high performance biometric signal and image processing method to reveal blood perfusion towards 3d oxygen saturation mapping", Progress Biomed Optics & Imaging [SPIE] (2014) 8947:89470 in 11 pages.
Israel et al., "Variations in Burn Excision and Grafting: A Survey of the American Burn Association", J Burn Care Res. (2017) 38(1): 125-132.
Jackson D. "The diagnosis of the depth of burning." Br J Surg. 1953; 40:588-596.
Jacques et al., "Absorption spectra for biological tissues," ECE532 Biomedical Optics, 1998, Available from: http://omlc.org/education/ece532/class3/muaspectra.html; 1 page.
Jacques, Steven L., "Optical properties of biological tissues: A review", Phys Med. Biol., 2013, 58 (12), R37-61 and Corrigendum 2013 58:5007-5008.
Jaskille et al., "Critical Review of burn depth assessment techniques: Part II. Review of Laser Doppler Technology", J Burn Care Res. (2010) 31(1): 151-157.
Jones et al., "Snapshot Spectral Imaging Technologies for On-Site Inspection", Presentation given at CTBTO Science and Technology 2015 (SnT2015) Jun. 26, 2015; Vienna, Austria; in 20 pages.
Kaiser et al., "Noninvasive assessment of burn wound severity using optical technology: A review of current and future modalities." Burns. 2011; 37(3): 377-386.
Kauvar et al., "Comparison of Combat and Non-Combat Burns From Ongoing U.S. Military Operations", J Surg Res. (2006) 132(1): 195-200.
Kearns et al., "Disaster planning: The past, present, and future concepts and principles of managing a surge of burn injured patients for those involved in hospital facility planning and preparedness," J Burn Care Res. Jan./Feb. 2014; 35(1):e33-e42.
King, Paul, Book Reviews; "Design of Pulse Oximeters," IEEE Eng. Med. Biol. Mag., 1998; p. 117.
King et al., "Surgical wound debridement sequentially characterized in a porcine burn model with multispectral imaging," Burns, 2015; 41:1478-1487.
Kono et al., "Identifying the incidence of and risk factors for reamputation among patients who underwent foot amputation," Ann Vasc Surg 2012; 26:1120-1126.
Lee et al., "Operative wound management," Chapter 13, ©2012 Elsevier Ltd, Inc, BV, DOI: 10.1016/B978-1-4377-2786-9l00013-8, pp. 157-172e2.
Li et al., "Review of spectral imaging technology in biomedical engineering: achievements and challenges," J Biomed Optics. 2013; 18(10):100901; 29 pages.
Li et al., "Burn injury diagnostic imaging device's accuracy improved by outlier detection and removal," Proc. Of SPIE, vol. 9472, 2015 SPIE, pp. 947206-1 to 947206-11.
Li et al., "Outlier detection and removal improves accuracy of machine learning approach to multispectral burn diagnostic imaging," J. Bio. Optics. Dec. 2015; 20(12):121305-1 to 121305-9.
Liu et al., "Toward integrating feature selection algorithms for classification and clustering." IEEE Transactions on Knowledge and Data Engineering. 2005. 17(4): 491-502; 35 pages.
Lu et al., "Medical hyperspectral imaging: A review," J Biomed Optics Jan. 2014; 19(1):0101901, 24 pages.
Macri et al., "Immediate burn excision fails to reduce injury progression," J Burn Care Res. 2013; 34(3):153-160.
Marimont et al., "Nearest Neighbor searches and the curse of Dimensionality," J Inst Math Applics 1979; 24 (1): 59-70.
Mertens et al., "Outpatient Burn Management," Nursing Clinics of North America, Burn Mgmt. 1997; 32(2):343-364.
Middlekoop et al., "Porcine wound models for skin substitution and burn treatment," Biomaterials. 2004;25:1559-1567.
Mo et al., "The importance of illumination in a non-contact photoplethysmography imaging system for burn wound assessment", Proc. SPIE 9303 Photonic Therapeutics and Diagnostics XI, 93030M, Feb. 2015; 10 pages.
Mook et al., "Instruments and techniques: Spectrophotometric determination of oxygen saturation of blood independent of the presence of indocyanine green," Cardiovascular Research, 1979; 13:233-237.
Moor Instruments, "Early and Accurate Burn Assessment with Laser Doppler Imaging", Product Brochure; Dec. 2014; 16 pages.
Moza et al., "Deep-Tissue Dynamic Monitoring of Decubitus Ulcers: Wound Care and Assessment," IEEE Eng Med Biol Mag. 2010; 29(2):71-77.
National Limb Loss Information Center, "Fact Sheet: Amputation Statistics by Cause: Limb Loss in the United States," National Limb Loss Information Center, Fact Sheet. Revised 2008, 3 pages.
Nehler et al., "Functional outcome in a contemporary series of major lower extremity amputations," J Vasc Surg. 2003; 38:7-14.
Nguyen et al., "Spatial frequency domain imaging of burn wounds in a preclinical model of graded burn severity." J Biomed Optics. 2013; 18(6): 066010; 8 pages.
Nilsson, Lena M. "Respiration Signals from Photoplethysmography.," Anesth Analg. 2013; 117(4):859-65.
Norgren et al., Inter-Society Consensus for the Management of Peripheral Arterial Disease (TASC II), J Vasc Surg. 2007; 45(Supp 1):S5A-S67A.
Nouri et al., "Colour and multispectral imaging for wound healing evaluation in the context of a comparative preclinical study", Proc Opt Diagnostics of Living Cells II, (2013) 8669:866923 in 11 pages.
Obermeyer et al., "Predicting the Future—Big Data, Machine Learning, and Clinical Medicine", N Engl J Med. (Sep. 2016) 375(13): 1216-1219.
Optics.org—The business of photonics, IMEC Launches TDI, multispectral and hyperspectral sensors; News-Release of Feb. 8, 2017; SPIE Europe in 4 pages.
Orgill, D., "Excision and skin grafting of thermal burns," New Eng J Med. 2011; 360:893-901.
Ortiz-Pujols et al., "Burn care: Are there sufficient providers and facilities?" Chapel Hill, North Carolina. American College of Surgeons Health Policy Research Institute, Nov. 2011; 9:4 pages.
Pape et al., "An audit of the use of laster Doppler imaging (LDI) in the assessment of burns of intermediate depth," Burns 2001; 27:233-239.
Peng et al., "Feature Selection Based on Mutual Information: Criteria of Max-Dependency, Max-Relevance, and Min-Redundancy," IEEE Trans. on Pattern Analysis and Machine Intelligence, 2005; 27(8):1226-1238.
Perkins et al., "Genie: A Hybrid Genetic Algorithm for Feature Classification in Multi-Spectral Images", in Applications and science of neural networks, fuzzy systems, and evolutionary computation III; Inter'l Society of Optics and Photonics (2000) 4120:52-63.
Petricoin et al., "SELDI-TOF-based serum proteomic pattern diagnostics for early detection of cancer", Curr Opin Biotechnol. (2004) 15(1): 24-30.
Reisner et al., "Utility of the Photoplethysmogram in Circulatory Monitoring", Anesthesiol. 2008; 108:950-958.
Resch et al., "Estimation of burn depth at burn centers in the United States: a survey." J Burn Care Res. Nov./Dec. 2014; 35: 491-497.
Resurge International, "Burns: The Neglected but Solvable Health Crisis" from Reconstructive Surgery for the World's Poor since 1969; accessed <http://www.resurge.org/transforming_lives/story_burns.cfm> Accessed Feb. 9, 2015; 3 pages.
Rogers et al., "The right to bear legs-An amendment to healthcare: how preventing amputations can save billions for the US health-care system," J Am Podiatr Med Assoc 2008; 98:166-168.
Rousseeuw, Peter J. "Least Median of Squares Regression". J Am Stat Assoc. 1984; 79(388):871-880.
Severinghaus et al., "History of Blood Gas Analysis. VII. Pulse Oximetry." J Clin Monitor. 1987; 3(2):135-138.
Singer et al., "A porcine burn model," Meth Mol Med. 2003; 78:107-119.
Sokolova et al., "A systematic analysis of performance measures for classification tasks." Info Proc Manag. 2009; 45: 427-437.
Sowa et al., "Near infrared spectroscopic assessment of hemodynamic changes in the early post-burn period", Burns (2001) 27: 241-249.
Sowa et al., "Classification of burn injuries using near-infrared spectroscopy", J Biomed Optics. (Sep. 2006) 11(5): 6 pages.

(56) References Cited

OTHER PUBLICATIONS

Spectral MD, Inc., "DeepView Digital Video Physiological Portable Imaging System", FDA Traditional 510(k) Application as filed Dec. 28, 2012; 528 pages.
Squiers et al., "Multispectral imaging burn wound tissue classification system: a comparison of test accuracies between several common machine learning algorithms," Proc. Of SPIE, 2016; 9785:97853L-1 to 97853L-10.
Thatcher et al., "Dynamic tissue phantoms and their use in assessment of a noninvasive optical plethysmography imaging device," SPIE Sensing Technology + Applications, May 2014; 910718, 18 pages.
Thatcher et al., "Imaging Techniques for Clinical Burn Assessment with a Focus on Multispectral Imaging," Advan Wound Care, Mar. 2016; 5(8):360-378.
Thatcher et al., "Multispectral and Photophlethysmography Optical Imaging Techniques Identify Important Tissue Characteristics in an Animal Model of Tangential Burn Excision," J Burn Care & Res., Jan./Feb. 2016, 37(1):38-52.
Themelis et al.,"Multispectral Imaging Using Multiple-bandpass filters", Opt Lett., May 2008; 33(9):1023-1025.
Tuchin, Valery V., "Light-Tissue Interactions", Biomedical Photonics Handbook, CRC Press, Boca Raton, Florida 2003; Chapter 3; pp. 123-167.
Usman et al., "Second Derivative of Photoplethysmogram in Estimating Vascular Aging Among Diabetic Patients," in Internet Conf for Technical Postgraduates 2009, TECHPOS 2009, 3 pages.
Vemulapalli et al., "Peripheral arterial testing before lower extremity amputation among Medicare beneficiaries, 2000 to 2010," Circ Cardiovasc Qual Outcomes, Jan. 2014, 7:142-150.
Vogel et al., "Using Non-Invasive Multi-Spectral Imaging to Quantitatively Assess Tissue Vasculature", J Biomed Optics (2007) 12(5): 051604 in 32 pages.
Waters et al., "Energy cost of walking of amputees: the influence of level of amputation," J Bone Joint Surg. 1975; 58(1):42-46.
Watts et al., "Burn depth and its histological measurement," Burns 27 (2001) 154-160.
Webb, Steve [Ed.], The physics of medical imaging, ©1988, IOP Publishing Ltd., TOC only.
Webster, J.G. [Ed.], Design of Pulse Oximeters, Medical Science Series, ©IOP Publishing Ltd. 1997;.
Worsley et al., "Back to basics: biophysical methods in tissue viability research," (Draft); J Wound Care, 2013; 22(8):434-439.
Wütschert et al., "Determination of Amputation Level in Ischemic Limbs—Reappraisal of the measurement of TcPo2", Diabetes Care, 1997; 20(8):1315-1318.
Ziegler-Graham et al., "Estimating the Prevalence of Limb Loss in the United States: 2005 to 2050," Arch Phys Med Rehabil. 2008; 89:422-429.
Zonios et al., "Skin melanin, hemoglobin, and light scattering properties can be quantitatively assessed in vivo using diffuse reflectance spectroscopy", J Invest Dermatol. (2001) 117(6): 1452-1457.
International Search Report and Written Opinion dated Feb. 20, 2020 for International Application No. PCT/US2019/065818.
Badrinarayanan et al., "SegNet: A Deep Convolutional Encoder-Decoder Architecture for Robust Semantic Pixel-Wise Labelling", Computer Science, CVPR 2015, https://arxiv.org/abs/1505.07293, May 2015.
Duda et al., *Pattern Classification*, Second Edition, John Wiley & Sons, Nov. 2000.
Ioffe et al., "Batch Normalization: Acceleration Deep Network Training by Reducing Internal Covariate Shift", https://arxiv.org/abs/1502.03167, 2015.
Kendall et al., "Bayesian SegNet: Model Uncertainty in Deep Convolutional Encoder-Decoder Architectures for Scene Understanding", https://arxiv.org/abs/1511.02680, Oct. 2016.
Spigulis et al., "A Device for Mulimodal Imaging of Skin", Multimodal Biomedical Imaging VIII, Proc. SPIE, vol. 8574, p. 85740J, Feb. 2013, 7 pages.
Steinberg et al., "Sample size for positive and negative predictive value in diagnostic research using case-control designs". Biostatistics, vol. 10, No. 1, pp. 94-105, 2009.
Siew, Ronian [Ed.], Multiple-Field Multispectral Imaging, Independently (2017); Chapter 1, pp. 1-12.
International Search Report and Written Opinion dated Apr. 20, 2020 for PCT/US2019/065820.
Elmasry et al., "Chapter 1: Principles of Hyperspectral Imaging Technology", *Hyperspectral Imaging for Food Quality Analysis and Control*, Dec. 2010, pp. 3-43.
Grubbs, Frank E., "Procedures for Detecting Outlying Observations in Samples", Technometrics, vol. 11(1), Feb. 1969, pp. 1-21.
Haberal et al., "Fluid management in major burn injuries", Indian J. Plast. Surg., Sep. 2010, vol. 43(Suppl), S29-S36.
Jolivot et al., "Skin Parameter Map Retrieval from a Dedicated Multispectral Imaging System Applied to Dermatology/Cosmetology", International Journal of Biomedical Imaging, Sep. 2013; vol. 3:978289, in 16 pages.
Lieberman, J.I. et al., National Preparedness: Countermeasures for Thermal Burns. United States Government Accountability Office. GAO-12-304R, Feb. 22, 2012.
Mohler, Emile R., "Screening for Peripheral Artery Disease", Circulation, Aug. 2012, vol. 126:e111-e112 in 2 pages.
Regensteiner et al, "The impact of peripheral arterial disease on health-related quality of life in the Peripheral Arterial Disease Awareness, Risk, and Treatment: New Resources for Survival (Partners) Program", Vascular Medicine, Feb. 2008, vol. 13:15-24.
Li et al., "Simultaneous measurement of deep tissue blood flow and oxygenation using noncontact diffuse correlation spectroscopy flow-oximeter", Scientific Reports, Feb. 2013, 3:1358, pp. 1-10.
Chinese Office Action in CN Application No. 201680076887.X, dated Jun. 3, 2020.

* cited by examiner

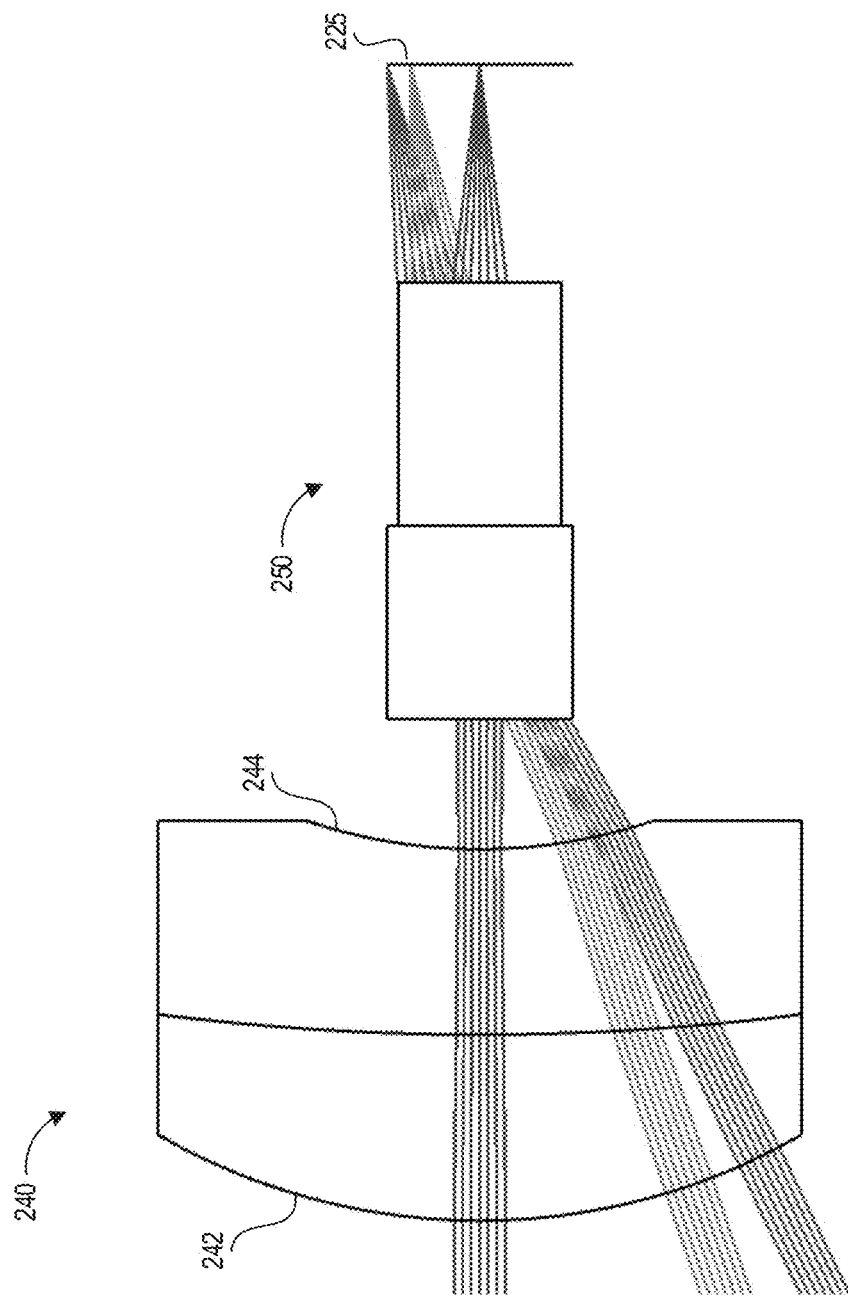

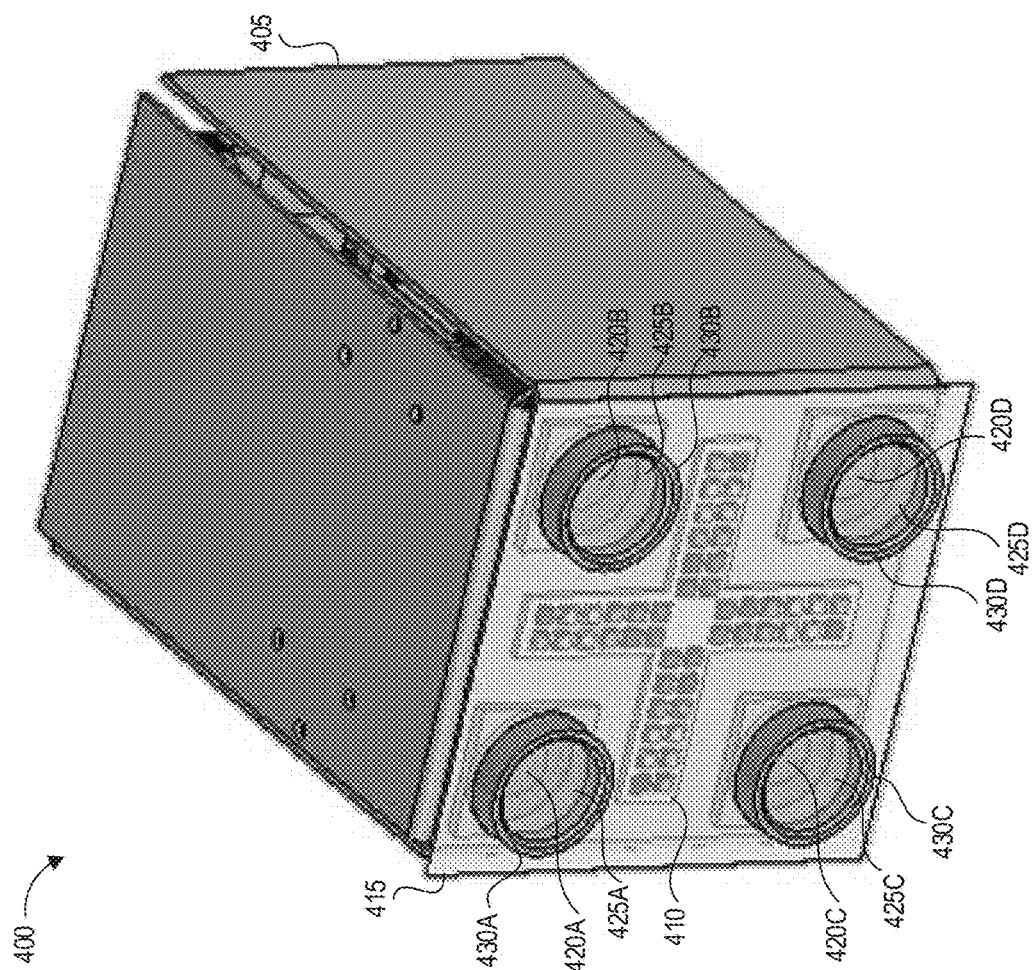

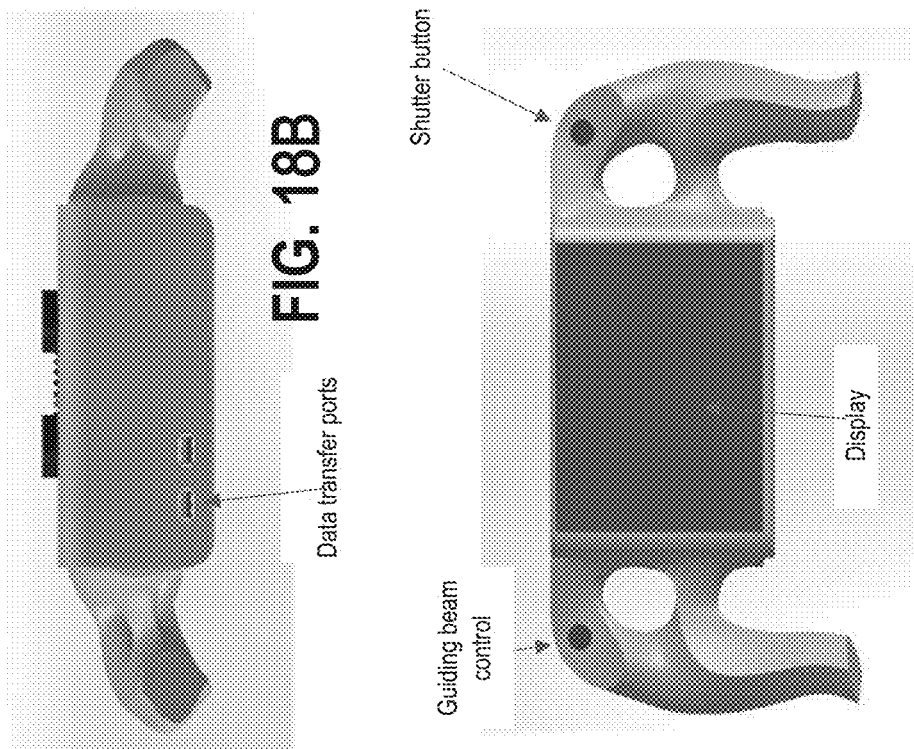
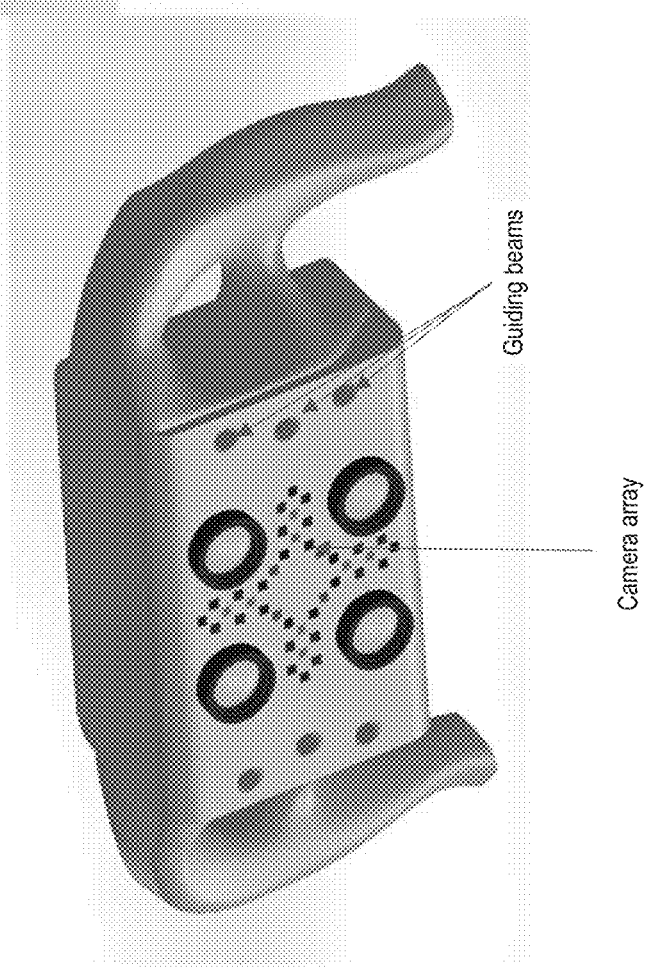
FIG. 18B
FIG. 18C — Shutter button, Display, Guiding beam control
FIG. 18A — Guiding beams, Camera array
Data transfer ports

MACHINE LEARNING SYSTEMS AND METHOD FOR ASSESSMENT, HEALING PREDICTION, AND TREATMENT OF WOUNDS

CROSS-REFERENCE TO RELATED APPLICATIONS

This application is a continuation of PCT/US2019/065820, filed Dec. 11, 2019, entitled "MACHINE LEARNING SYSTEMS AND TECHNIQUES FOR ASSESSMENT, HEALING PREDICTION, AND TREATMENT OF WOUNDS," which claims the benefit of U.S. Provisional Application Ser. No. 62/780,854, filed Dec. 17, 2018, entitled "PREDICTION OF DIABETIC FOOT ULCER HEALING UPON INITIAL VISIT USING ARTIFICIAL INTELLIGENCE," U.S. Provisional Application Ser. No. 62/780,121, filed Dec. 14, 2018, entitled "SYSTEM AND METHOD FOR HIGH PRECISION MULTI-APERTURE SPECTRAL IMAGING," and U.S. Provisional Application Ser. No. 62/818,375, filed Mar. 14, 2019, entitled "SYSTEM AND METHOD FOR HIGH PRECISION MULTI-APERTURE SPECTRAL IMAGING," all of which are hereby expressly incorporated by reference in their entirety and for all purposes.

STATEMENT REGARDING FEDERALLY SPONSORED R&D

Some of the work described in this disclosure was made with United States Government support under Contract No. HHSO100201300022C, awarded by the Biomedical Advanced Research and Development Authority (BARDA), within the Office of the Assistant Secretary for Preparedness and Response in the U.S. Department of Health and Human Services. Some of the work described in this disclosure was made with United Government support under Contract Nos. W81XWH-17-C-0170 and/or W81XWH-18-C-0114, awarded by the U.S. Defense Health Agency (DHA). The United States Government may have certain rights in this invention.

TECHNICAL FIELD

The systems and methods disclosed herein are directed to medical imaging, and, more particularly, to wound assessment, healing prediction, and treatment using machine learning techniques.

BACKGROUND

Optical imaging is an emerging technology with potential for improving disease prevention, diagnosis, and treatment at the scene of an emergency, in the medical office, at the bedside, or in the operating room. Optical imaging technologies can noninvasively differentiate among tissues, and between native tissues and tissue labeled with either endogenous or exogenous contrast media, measuring their different photon absorption or scattering profiles at different wavelengths. Such photon absorption and scattering differences offers potential for providing specific tissue contrasts, and enables studying functional and molecular level activities that are the basis for health and disease.

The electromagnetic spectrum is the range of wavelengths or frequencies over which electromagnetic radiation (e.g., light) extends. In order from longer wavelengths to shorter wavelengths, the electromagnetic spectrum includes radio waves, microwaves, infrared (IR) light, visible light (that is, light that is detectable by the structures of the human eye), ultraviolet (UV) light, x-rays, and gamma rays. Spectral imaging refers to a branch of spectroscopy and photography in which some spectral information or a complete spectrum is collected at locations in an image plane. Some spectral imaging systems can capture one or more spectral bands. Multispectral imaging systems can capture multiple spectral bands (on the order of a dozen or less and typically at discrete spectral regions), for which spectral band measurements are collected at each pixel, and can refer to bandwidths of about tens of nanometers per spectral channel. Hyperspectral imaging systems measure a greater number of spectral bands, for example as many as 200 or more, with some providing a continuous sampling of narrow bands (e.g., spectral bandwidths on the order of nanometers or less) along a portion of the electromagnetic spectrum.

SUMMARY

Aspects of the technology described herein relate to devices and methods that can be used to assess and/or classify tissue regions at or near a wound using non-contact, non-invasive, and non-radiation optical imaging. Such devices and methods may, for example, identify tissue regions corresponding to different tissue health classifications relating to wounds and/or determine predicted healing parameters for a wound or a portion thereof, and can output a visual representation of the identified regions and/or parameters for use by a clinician in determining a wound healing prognosis or selecting an appropriate wound care therapy or both. In some embodiments, the devices and methods of the present technology can provide such classification and/or prediction based on imaging at a single wavelength or at a plurality of wavelengths. There has been a long felt need for non-invasive imaging techniques that can provide physicians with information for quantitatively predicting healing for wounds or portions thereof.

In one aspect, a system for assessing or predicting wound healing comprises at least one light detection element configured to collect light of at least a first wavelength after being reflected from a tissue region comprising a wound, and one or more processors in communication with the at least one light detection element. The one or more processors are configured to receive a signal from the at least one light detection element, the signal representing light of the first wavelength reflected from the tissue region; generate, based on the signal, an image having a plurality of pixels depicting the tissue region; determine, based on the signal, a reflectance intensity value at the first wavelength for each pixel of at least a subset of the plurality of pixels; determine one or more quantitative features of the subset of the plurality of pixels based on the reflectance intensity values of each pixel of the subset; and generate, using one or more machine learning algorithms, at least one scalar value based on the one or more quantitative features of the subset of the plurality of pixels, the at least one scalar value corresponding to a predicted or assessed healing parameter over a predetermined time interval.

In some embodiments, the wound is a diabetic foot ulcer. In some embodiments, the predicted healing parameter is a predicted amount of healing of the wound. In some embodiments, the predicted healing parameter is a predicted percent area reduction of the wound. In some embodiments, the at least one scalar value comprises a plurality of scalar values, each scalar value of the plurality of scalar values corresponding to a probability of healing of an individual pixel of the subset or of a subgroup of individual pixels of the subset. In some embodiments, the one or more processors are further configured to output a visual representation of the plurality of scalar values for display to a user. In some embodiments, the visual representation comprises the image having each pixel of the subset displayed with a particular visual representation selected based on the probability of healing corresponding to the pixel, wherein pixels associated with different probabilities of healing are displayed in different visual representations. In some embodiments, the one or more machine learning algorithms comprise a SegNet pre-trained using a wound, burn, or ulcer image database. In some embodiments, the wound image database comprises a diabetic foot ulcer image database. In some embodiments, the wound image database comprises a burn image database. In some embodiments, the predetermined time interval is 30 days. In some embodiments, the one or more processors are further configured to identify at least one patient health metric value corresponding to a patient having the tissue region, and wherein the at least one scalar value is generated based on the one or more quantitative features of the subset of the plurality of pixels and on the at least one patient health metric value. In some embodiments, the at least one patient health metric value comprises at least one variable selected from the group consisting of demographic variables, diabetic foot ulcer history variables, compliance variables, endocrine variables, cardiovascular variables, musculoskeletal variables, nutrition variables, infectious disease variables, renal variables, obstetrics or gynecology variables, drug use variables, other disease variables, or laboratory values. In some embodiments, the at least one patient health metric value comprises one or more clinical features. In some embodiments, the one or more clinical features comprise at least one feature selected from the group consisting of an age of the patient, a level of chronic kidney disease of the patient, a length of the wound on a day when the image is generated, and a width of the wound on the day when the image is generated. In some embodiments, the first wavelength is within the range of 420 nm±20 nm, 525 nm±35 nm, 581 nm±20 nm, 620 nm±20 nm, 660 nm±20 nm, 726 nm±41 nm, 820 nm±20 nm, or 855 nm±30 nm. In some embodiments, the first wavelength is within the range of 620 nm±20 nm, 660 nm±20 nm, or 420 nm±20 nm. In some embodiments, the one or more machine learning algorithms comprise a random forest ensemble. In some embodiments, the first wavelength is within the range of 726 nm±41 nm, 855 nm±30 nm, 525 nm±35 nm, 581 nm±20 nm, or 820 nm±20 nm. In some embodiments, the one or more machine learning algorithms comprise an ensemble of classifiers. In some embodiments, the system further comprises an optical bandpass filter configured to pass light of at least the first wavelength. In some embodiments, the one or more processors are further configured to automatically segment the plurality of pixels of the image into wound pixels and non-wound pixels, and select the subset of the plurality of pixels to comprise the wound pixels. In some embodiments, the one or more processors are further configured to automatically segment the non-wound pixels into callus pixels and background pixels. In some embodiments, the one or more processors are further configured to automatically segment the non-wound pixels into callus pixels, normal skin pixels, and background pixels. In some embodiments, the one or more processors automatically segment the plurality of pixels using a segmentation algorithm comprising a convolutional neural network. In some embodiments, the segmentation algorithm is at least one of a U-Net comprising a plurality of convolutional layers and a SegNet comprising a plurality of convolutional layers. In some embodiments, the one or more quantitative features of the subset of the plurality of pixels comprise one or more aggregate quantitative features of the plurality of pixels. In some embodiments, the one or more aggregate quantitative features of the subset of the plurality of pixels are selected from the group consisting of a mean of the reflectance intensity values of the pixels of the subset, a standard deviation of the reflectance intensity values of the pixels of the subset, and a median reflectance intensity value of the pixels of the subset. In some embodiments, the one or more processors are further configured to individually apply a plurality of filter kernels to the image by convolution to generate a plurality of image transformations; construct a 3D matrix from the plurality of image transformations; and determine one or more quantitative features of the 3D matrix, wherein the at least one scalar value is generated based on the one or more quantitative features of the subset of the plurality of pixels and on the one or more quantitative features of the 3D matrix. In some embodiments, the one or more quantitative features of the 3D matrix are selected from the group consisting of a mean of the values of the 3D matrix, a standard deviation of the values of the 3D matrix, a median value of the 3D matrix, and a product of the mean and the median of the 3D matrix. In some embodiments, the at least one scalar value is generated based on the mean of the reflectance intensity values of the pixels of the subset, the standard deviation of the reflectance intensity values of the pixels of the subset, the median reflectance intensity value of the pixels of the subset, the mean of the values of the 3D matrix, the standard deviation of the values of the 3D matrix, and the median value of the 3D matrix. In some embodiments, the at least one light detection element is further configured to collect light of at least a second wavelength after being reflected from the tissue region, and the one or more processors are further configured to receive a second signal from the at least one light detection element, the second signal representing light of the second wavelength reflected from the tissue region; determine, based on the second signal, a reflectance intensity value at the second wavelength for each pixel of at least the subset of the plurality of pixels; and determine one or more additional quantitative features of the subset of the plurality of pixels based on the reflectance intensity values of each pixel at the second wavelength, wherein the at least one scalar value is generated based at least in part on the one or more additional quantitative features of the subset of the plurality of pixels.

In a second aspect, a system for wound assessment comprises at least one light detection element configured to collect light of at least a first wavelength after being reflected form a tissue region comprising a wound, and one or more processors in communication with the at least one light detection element. The one or more processors are configured to receive a signal from the at least one light detection element, the signal representing light of the first wavelength reflected from the tissue region; generate, based on the signal, an image having a plurality of pixels depicting the tissue region; determine, based on the signal, a reflectance intensity value at the first wavelength for each pixel of the plurality of pixels; and automatically segment, using a machine learning algorithm, individual pixels of the plurality of pixels into at least a first subset of the plurality of pixels comprising wound pixels and a second subset of the plurality of pixels comprising non-wound pixels, based on individual reflectance intensity values of the plurality of pixels.

In some embodiments, the one or more processors are further configured to automatically segment the second subset of the plurality of pixels into at least two categories of non-wound pixels, the at least two categories selected from the group consisting of callus pixels, normal skin pixels, and background pixels. In some embodiments, the machine learning algorithm comprises a convolutional neural network. In some embodiments, the machine learning algorithm is at least one of a U-Net comprising a plurality of convolutional layers and a SegNet comprising a plurality of convolutional layers. In some embodiments, the machine learning algorithm is trained based on a dataset comprising a plurality of segmented images of wounds, ulcers, or burns. In some embodiments, the wound is a diabetic foot ulcer. In some embodiments, the one or more processors are further configured to output a visual representation of the segmented plurality of pixels for display to a user. In some embodiments, the visual representation comprises the image having each pixel displayed with a particular visual representation selected based on the segmentation of the pixel, wherein wound pixels and non-wound pixels are displayed in different visual representations.

In another aspect, a method of predicting wound healing using a system for assessing or predicting wound healing comprises illuminating the tissue region with light of at least the first wavelength such that the tissue region reflects at least a portion of the light to the at least one light detection element, using the system to generate the at least one scalar value, and determining the predicted healing parameter over the predetermined time interval.

In some embodiments, illuminating the tissue region comprises activating one or more light emitters configured to emit light of at least the first wavelength. In some embodiments, illuminating the tissue region comprises exposing the tissue region to ambient light. In some embodiments, determining the predicted healing parameter comprises determining an expected percent area reduction of the wound over the predetermined time interval. In some embodiments, the method further comprises measuring one or more dimensions of the wound after the predetermined time interval has elapsed following the determination of the predicted amount of healing of the wound, determining an actual amount of healing of the wound over the predetermined time interval, and updating at least one machine learning algorithm of the one or more machine learning algorithms by providing at least the image and the actual amount of healing of the wound as training data. In some embodiments, the method further comprises selecting between a standard wound care therapy and an advanced wound care therapy based at least in part on the predicted healing parameter. In some embodiments, selecting between the standard wound care therapy and the advanced wound care therapy comprises, when the predicted healing parameter indicates that the wound, preferably a DFU, will heal or close by greater than 50% in 30 days, indicating or applying one or more standard therapies selected from the group consisting of optimization of nutritional status, debridement by any means to remove devitalized tissue, maintenance of a clean moist bed of granulation tissue with appropriate moist dressings, necessary therapy to resolve any infection that may be present, addressing any deficiencies in vascular perfusion to the extremity with the DFU, offloading of pressure from the DFU, and appropriate glucose control; and when the predicted healing parameter indicates that the wound, preferably a DFU, will not heal or close by greater than 50% in 30 days, indicating or applying one or more advanced care therapies selected from the group consisting of hyperbaric oxygen therapy, negative-pressure wound therapy, bioengineered skin substitutes, synthetic growth factors, extracellular matrix proteins, matrix metalloproteinase modulators, and electrical stimulation therapy.

BRIEF DESCRIPTION OF THE DRAWINGS

FIGS. 3B-3D depict example optical designs for optical components of one light path of the multi-aperture imaging system of FIG. 3A.

FIG. 5 depicts another embodiment of a multispectral multi-aperture imaging system, with an optical design as described with respect to FIGS. 3A and 3B.

FIGS. 18A-18C illustrate an example handheld embodiment of a multispectral, multi-aperture imaging system.

DETAILED DESCRIPTION

Figure 1B:
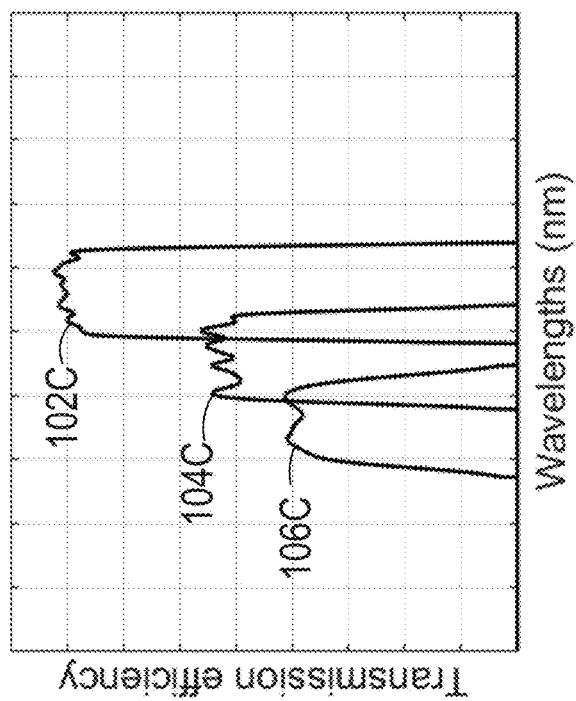
FIG. 1B is a graph illustrating example transmission efficiencies provided by the filter of FIG. 1A for various chief ray angles.

Approximately 15-25% of the 26 million Americans with diabetes will develop a diabetic foot ulcer (DFU). These wounds lead to a loss of mobility, and lower quality of life. As many as 40% of those who develop a DFU will develop a wound infection that increases the risk of amputation and death. Mortality related to DFUs alone is as high as 5% during the first year and as high as 42% within five years. This is heightened by a high annual risk of major amputation (4.7%) and minor amputation (39.8%). Furthermore, the cost to treat one DFU annually is approximately $22,000 to $44,000, and the overall burden to the U.S. healthcare system due to DFUs is in the range of $9 billion to $13 billion per year.

It is generally accepted that DFUs with greater than 50% area reduction (PAR) after 30 days will heal by 12 weeks with standard of care therapy. However, using this metric requires four weeks of wound care before one can determine if a more effective therapy (e.g., an advanced care therapy) should be used. In a typical clinical approach to wound care for non-urgent initial presentation, such as for a DFU, a patient receives standard wound care therapy (e.g., correction of vascular problems, optimization of nutrition, glucose control, debridement, dressings, and/or off-loading) for approximately 30 days following the presentation and initial assessment of the wound. At approximately day 30, the wound is assessed to determine if it is healing (e.g., percent area reduction of greater than 50%). If the wound is not healing sufficiently, the treatment is supplemented with one or more advanced wound management therapies, which may include growth factors, bioengineered tissues, hyperbaric oxygen, negative pressure, amputation, recombinant human platelet-derived growth factor (e.g., Regranex™ Gel), bio-engineered human dermal substitutes (e.g., Dermagraft™), and/or living, bi-layered skin substitutes (e.g., Apligraf™). However, approximately 60% of DFUs fail to show sufficient healing after 30 days of standard wound care therapy. In addition, approximately 40% of DFUs with early healing still fail to heal by 12 weeks, and median DFU healing time has been estimated at 147 days, 188 days, and 237 days for toe, midfoot, and heel ulcers, respectively.

DFUs that fail to achieve desirable healing after 30 days of conventional or standard of care wound thereapy would benefit from the provision of advanced wound care therapies as early as possible e.g., during the initial 30 days of wound therapy. However, using conventional assessment methods, physicians typically cannot accurately identify a DFU that will not respond to 30 days of standard wound care therapy. Many successful strategies that improve DFU therapy are available but are not prescribed until standard wound care therapy is ruled out empirically. Physiologic measurement devices have been used to attempt to diagnose the healing potential of a DFU, such as transcutaneous oxygen measurement, laser Doppler imaging, and indocyanine green videoangiography. However, these devices have suffered from inaccuracy, lack of useful data, lack of sensitivity, and prohibitively high cost, and thuse have not been suitable for widespread use in the assessment of DFUs and other wounds. Clearly, an earlier and more accurate means of predicting DFU or other wound healing is important to quickly determine the best therapy and reduce time to wound closure.

Generally described, the present technology provides non-invasive and point-of-care imaging devices capable of diagnosing the healing potential of DFUs, burns, and other wounds. In various embodiments, the systems and methods of the present technology can enable a clinician to determine, at or shortly after the time of presentation or initial assessment, the healing potential of the wound. In some embodiments, the present technology can enable the determination of healing potential of individual sections of a wound, such as a DFU or burn. Based on the predicted healing potential, a decision between standard and advanced wound care therapies can be made on or near day 0 of therapy, rather than being deferred until over 4 weeks from the initial presentation. Accordingly, the present technology may result in reduced healing times and fewer amputations.
Example Spectral and Multi-spectral Imaging Systems Various spectral and multi-spectral imaging systems will now be described, each of which may be used in accordance with the DFU and other wound assement, prediction, and therapeutic methods disclosed herein. In some embodiments, images for wound assessment may be captured with spectral imaging systems configured to image light within a single wavelength band. In other embodiments, images may be captured with spectral imaging systems configured to capture two or more wavelength bads. In one particular example, images may be captured with a monochrome, RGB, and/or infrared imaging device such as those included in commercially available mobile devices. Further embodiments relate to spectral imaging using a multi-aperture system with curved multi-bandpass filters positioned over each aperture. However, it will be understood that the wound assessment, prediction, and therapeutic methods of the present technology are not limited to the specific image acquisition devices disclosed herein, and may equally be implemented with any imaging device capable of acquiring image data in one or more known wavelength bands.

The present disclosure further relates to techniques for implementing spectral unmixing and image registration to generate a spectral datacube using image information received from such imaging systems. The disclosed technology addresses a number of challenges that are typically present in spectral imaging, described below, in order to yield image data that represents precise information about wavelength bands that were reflected from an imaged object. In some embodiments, the systems and methods described herein acquire images from a wide area of tissue (e.g., 5.9×7.9 inches) in a short amount of time (e.g., within 6 seconds or less) and can do so without requiring the injection of imaging contrast agents. In some aspects, for example, the multispectral image system described herein is configured to acquire images from a wide area of tissue, e.g., 5.9×7.9 inches, within 6 seconds or less and, wherein said multispectral image system is also configured to provide tissue analysis information, such as identification of a plurality of burn states, wound states, ulcer states, healing potential, a clinical characteristic including a cancerous or non-cancerous state of the imaged tissue, wound depth, wound volume, a margin for debridement, or the presence of a diabetic, non-diabetic, or chronic ulcer in the absence of imaging contrast agents. Similarly, in some of the methods described herein, the multispectral image system acquires images from a wide area of tissue, e.g., 5.9×7.9 inches, within 6 seconds or less and said multispectral image system ouputs tissue analysis information, such as identification of a plurality of burn states, wound states, healing potential, a clinical characteristic including a cancerous or non-cancerous state of the imaged tissue, wound depth, wound volume, a margin for debridement, or the presence of a diabetic, non-diabetic, or chronic ulcer in the absence of imaging contrast agents.

One such challenge in existing solutions is that captured images can suffer from color distortions or disparity that compromise the quality of the image data. This can be particularly problematic for applications that depend upon precise detection and analysis of certain wavelengths of light using optical filters. Specifically, color shading is a position dependent variation in the wavelength of light across the area of the image sensor, due to the fact that transmittance of a color filter shifts to shorter wavelengths as the angle of light incident on the filter increases. Typically, this effect is observed in interference-based filters, which are manufactured through the deposition of thin layers with varying refractive indices onto a transparent substrate. Accordingly, longer wavelengths (such as red light) can be blocked more at the edges of the image sensor due to larger incident light ray angles, resulting in the same incoming wavelength of light being detected as a spatially non-uniform color across the image sensor. If left uncorrected, color shading manifests as shift in color near the edges of the captured image.

The technology of the present disclosure provides many more benefits relative to other multi-spectral imaging systems on the market because it is not restrictive in the configuration of lens and/or image sensors and their respective fields of view or aperture sizes. It will be understood that changes to lenses, image sensors, aperture sizes, or other components of the presently disclosed imaging systems may involve other adjustments to the imaging system as would be known to those of ordinary skill in the art. The technology of the present disclosure also provides improvements over other multi-spectral imaging systems in that the components that perform the function of resolving wavelengths or causing the system as a whole to be able to resolve wavelengths (e.g., optical filters or the like) can be seperable from the components that transduce light energy into digital outputs (e.g., image sensors or the like). This reduces the cost, complexity, and/or development time to re-configure imaging systems for different multi-spectral wavelengths. The technology of the present disclosure may be more robust than other multi-spectral imaging systems in that it can accomplish the same imaging characteristics as other multi-spectral imaging systems on the market in a smaller and lighter form factor. The technology of the present disclosure is also beneficial relative to other multi-spectral imaging systems in that it can acquire multi-spectral images in a snapshot, video rate, or high speed video rate. The technology of the present disclosure also provides a more robust implementation of multi-spectral imaging systems based on multi-aperture technology as the ability to multiplex several spectral bands into each aperture reduces the number of apertures necessary to acquire any particular number of spectral bands in an imaging data set, thus reducing costs through a reduced number of apertures and improved light collection (e.g., as larger apertures may be used within the fixed size and dimensions of commercially available sensor arrays). Finally, the technology of the present disclosure can provide all of these benefits without a trade-off with respect to resolution or image quality.

Figure 1A:
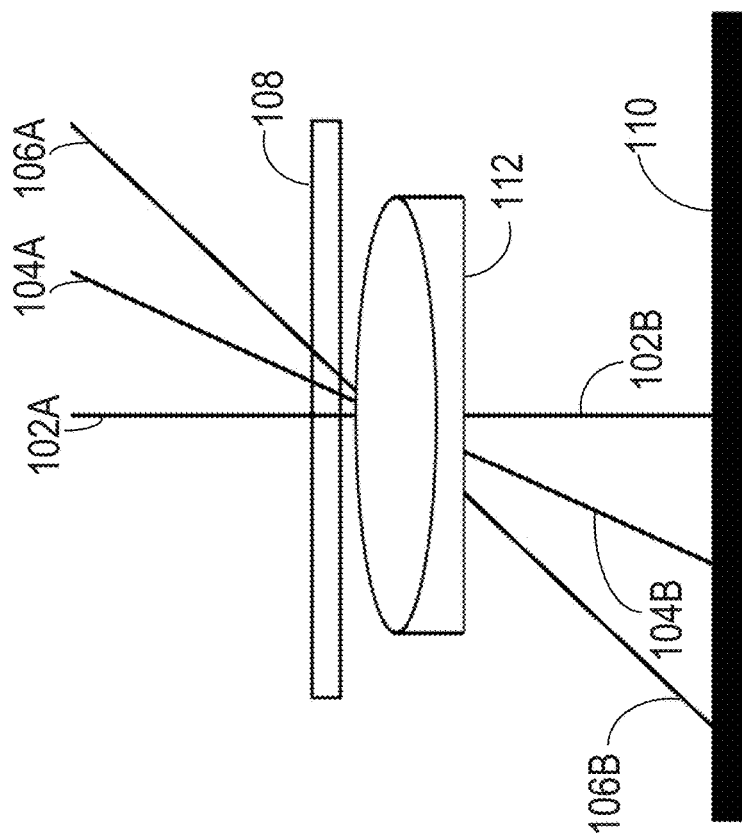
FIG. 1A illustrates an example of light incident on a filter at different chief ray angles.

FIG. 1A illustrates an example of a filter 108 positioned along the path of light towards an image sensor 110, and also illustrates light incident on the filter 108 at different ray angles. The rays 102A, 104A, 106A are represented as lines which, after passing through the filter 108, are refracted onto the sensor 110 by a lens 112, which may also be substituted with any other image-forming optics, including but not limited to a mirror and/or an aperture. The light for each ray is presumed in FIG. 1A to be broadband, for example, having a spectral composition extending over a large wavelength range to be selectively filtered by filter 108. The three rays 102A, 104A, 106A each arrive at the filter 108 at a different angle. For illustrative purposes, light ray 102A is shown as being incident substantially normal to filter 108, light ray 104A has a greater angle of incidence than light ray 102A, and light ray 106A has a greater angle of incidence than light ray 104A. The resulting filtered rays 102B, 104B, 106B exhibit a unique spectrum due to the angular dependence of the transmittance properties of the filter 108 as seen by the sensor 110. The effect of this dependence causes a shift in the bandpass of the filter 108 towards shorter wavelengths as the angle of incidence increases. Additionally, the dependence may cause a reduction in the transmission efficiency of the filter 108 and an altering of the spectral shape of the bandpass of the filter 108. These combined effects are referred to as the angular-dependent spectral transmission. FIG. 1B depicts the spectrum of each light ray in FIG. 1A as seen by a hypothetical spectrometer at the location of sensor 110 to illustrate the shifting of the spectral bandpass of filter 108 in response to increasing angle of incidence. The curves 102C, 104C, and 106C demonstrate the shortening of the center wavelength of the bandpass; hence, the shortening of the wavelengths of light passed by the optical system in the example. Also shown, the shape of the bandpass and the peak transmission are altered due to the angle incidence, as well. For certain consumer applications, image processing can be applied to remove the visible effects of this angular-dependent spectral transmission. However, these post-processing techniques do not allow for recovery of precise information regarding which wavelength of light was actually incident upon the filter 108. Accordingly, the resulting image data may be unusable for certain high-precision applications.

Figure 2A:
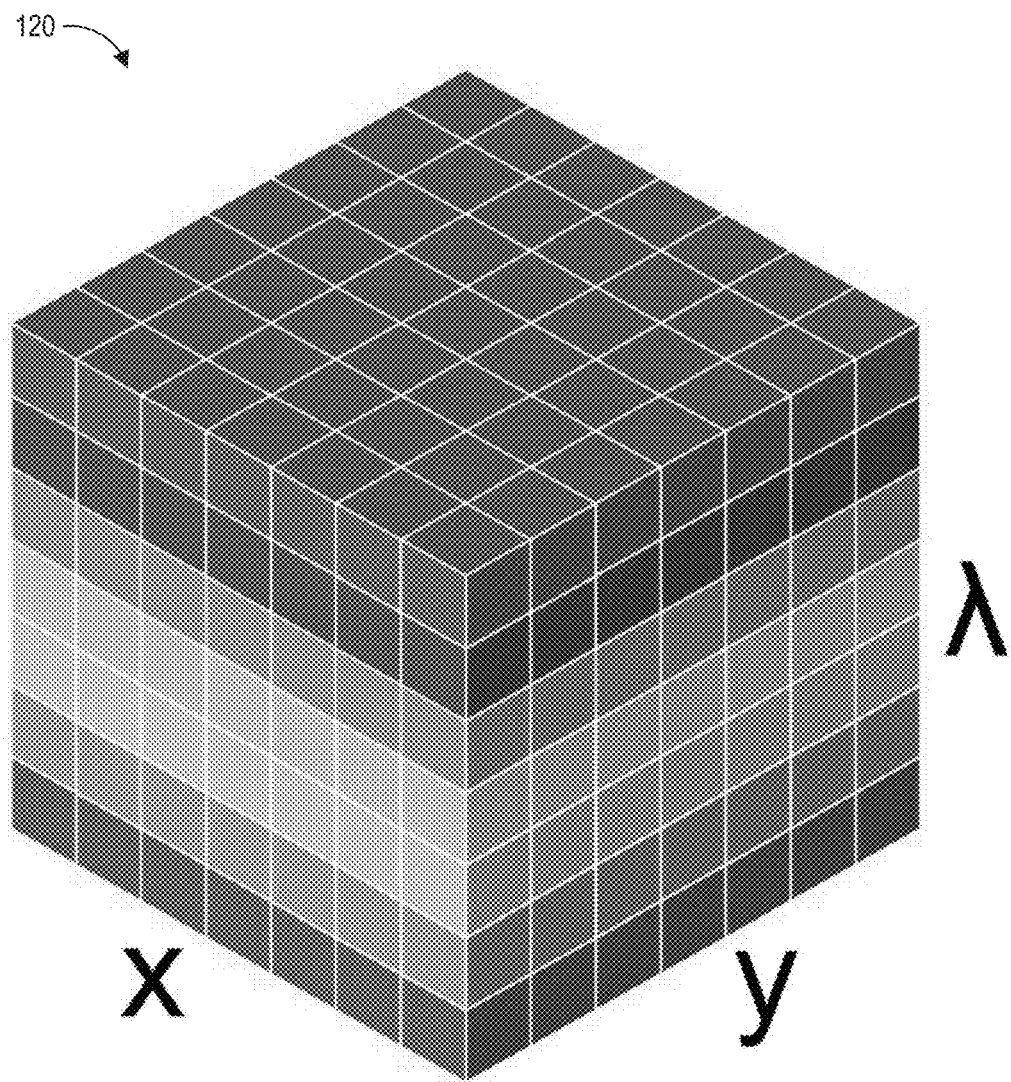
FIG. 2A illustrates an example of a multispectral image datacube.

Another challenge faced by certain existing spectral imaging systems is the time required for capture of a complete set of spectral image data, as discussed in connection with FIGS. 2A and 2B. Spectral imaging sensors sample the spectral irradiance $I(x,y,\lambda)$ of a scene and thus collect a three-dimensional (3D) dataset typically called a datacube. FIG. 2A illustrates an example of a spectral image datacube 120. As illustrated, the datacube 120 represents three dimensions of image data: two spatial dimensions (x and y) corresponding to the two-dimensional (2D) surface of the image sensor, and a spectral dimension ($\lambda$) corresponding to a particular wavelength band. The dimensions of the datacube 120 can be given by $N_x N_y N_\lambda$, where $N_x$, $N_y$, and $N_\lambda$ are the number of sample elements along the (x, y) spatial dimensions and spectral axes $\lambda$, respectively. Because datacubes are of a higher dimensionality than 2D detector arrays (e.g., image sensors) that are currently available, typical spectral imaging systems either capture time-sequential 2D slices, or planes, of the datacube 120 (referred to herein as "scanning" imaging systems), or simultaneously measure all elements of the datacube by dividing it into multiple 2D elements that can be recombined into datacube 120 in processing (referred to herein as "snapshot" imaging systems).

Figure 2B:
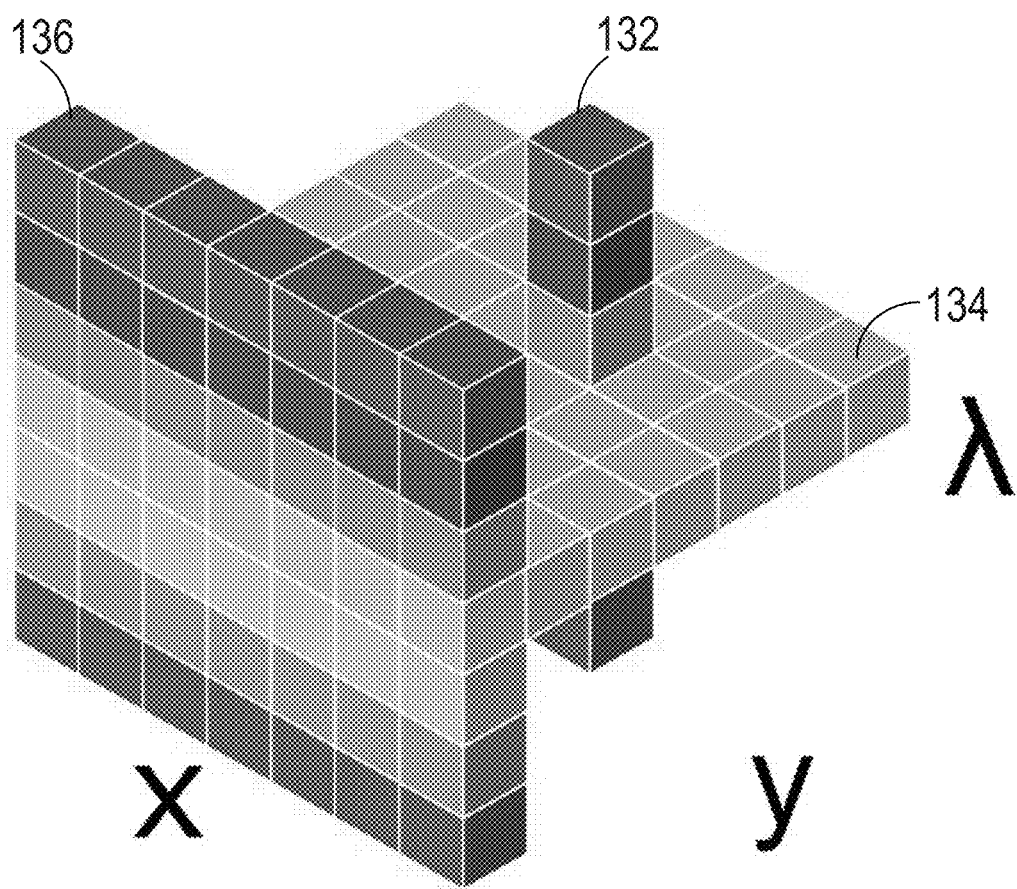
FIG. 2B illustrates examples of how certain multispectral imaging technologies generate the datacube of FIG. 2A.

FIG. 2B illustrates examples of how certain scanning spectral imaging technologies generate the datacube 120. Specifically, FIG. 2B illustrates the portions 132, 134, and 136 of the datacube 120 that can be collected during a single detector integration period. A point scanning spectrometer, for example, can capture a portion 132 that extends across all spectral planes $\lambda$ at a single (x, y) spatial position. A point scanning spectrometer can be used to build the datacube 120 by performing a number of integrations corresponding to each (x, y) position across the spatial dimensions. A filter wheel imaging system, for example, can capture a portion 134 that extends across the entirety of both spatial dimensions x and y, but only a single spectral plane $\lambda$. A wavelength scanning imaging system, such as a filter wheel imaging system, can be used to build the datacube 120 by performing a number of integrations corresponding to the number of spectral planes $\lambda$. A line scanning spectrometer, for example, can capture a portion 136 that extends across all spectral dimensions $\lambda$ and all of one of the spatial dimension (x or y), but only a single point along the other spatial dimension (y or x). A line scanning spectrometer can be used to build the datacube 120 by performing a number of integrations corresponding to each position of this other spatial dimension (y or x).

For applications in which the target object and imaging system are both motionless (or remain relatively still over the exposure times), such scanning imaging systems provide the benefit of yielding a high resolution datacube 120. For line scanning and wavelength scanning imaging systems, this can be due to the fact that each spectral or spatial image is captured using the entire area of the image sensor. However, movement of the imaging system and/or object between exposures can cause artifacts in the resulting image data. For example, the same (x, y) position in the datacube 120 can actually represent a different physical location on the imaged object across the spectral dimension $\lambda$. This can lead to errors in downstream analysis and/or impose an additional requirement for performing registration (e.g., aligning the spectral dimension $\lambda$ so that a particular (x, y) position corresponds to the same physical location on the object).

Figure 2C:
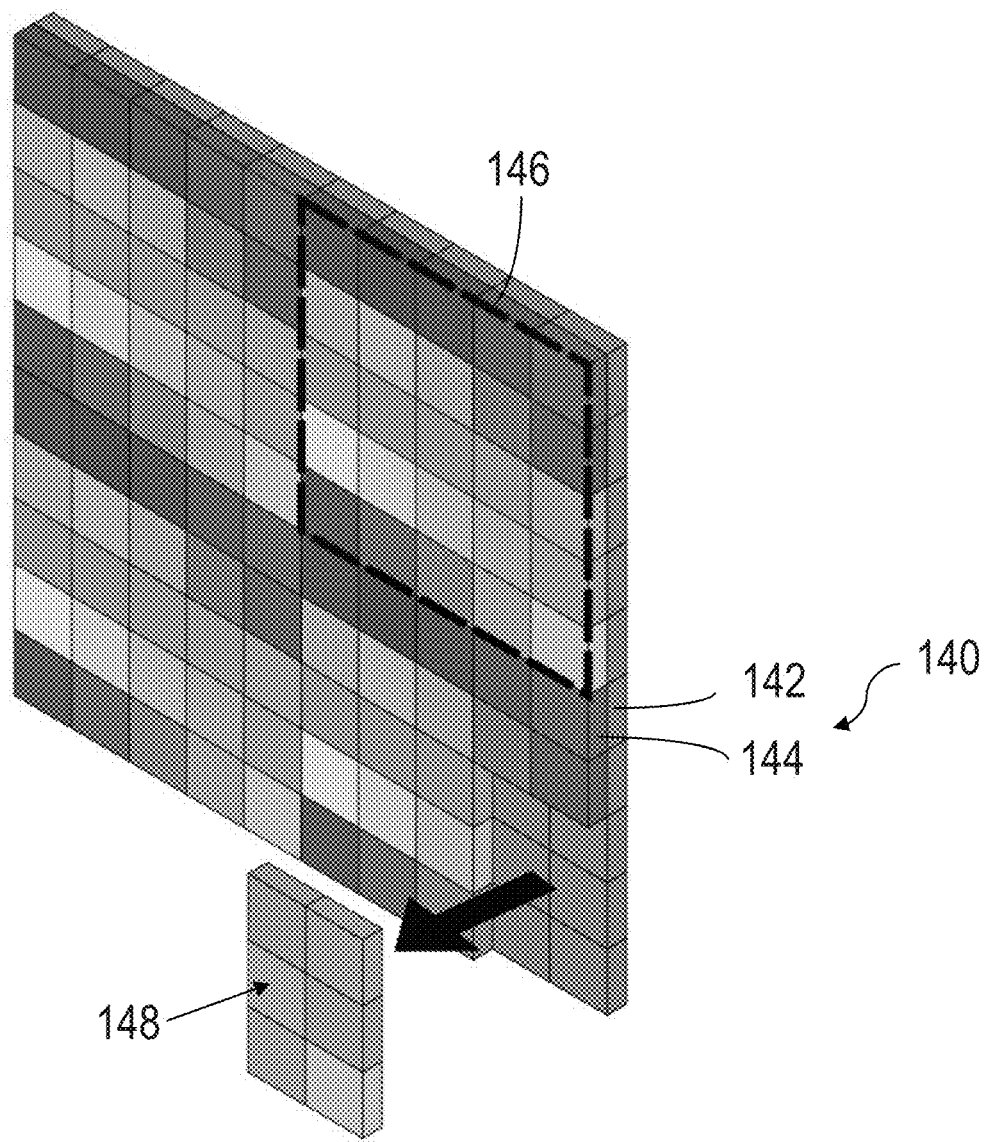
FIG. 2C depicts an example snapshot imaging system that can generate the datacube of FIG. 2A.

In comparison, a snapshot imaging system 140 can capture an entire datacube 120 in a single integration period or exposure, thereby avoiding such motion-induced image quality issues. FIG. 2C depicts an example image sensor 142 and an optical filter array such as a color filter array (CFA) 144 that can be used to create a snapshot imaging system. The CFA 144 in this example is a repeating pattern of color filter units 146 across the surface of the image sensor 142. This method of acquiring spectral information can also be referred to as a multispectral filter array (MSFA) or a spectrally resolved detector array (SRDA). In the illustrated example, the color filter unit 146 includes a 5×5 arrangement of different color filters, which would generate 25 spectral channels in the resulting image data. By way of these different color filters, the CFA can split incoming light into the bands of the filters, and direct the split light to dedicated photoreceptors on the image sensor. In this way, for a given color 148, only $\frac{1}{25}^{th}$ of the photoreceptors actually detect a signal represent light of that wavelength. Thus, although 25 different color channels can be generated in a single exposure with this snapshot imaging system 140, each color channel represents a smaller quantity of measured data than the total output of the sensor 142. In some embodiments, a CFA may include one or more of a filter array (MSFA), a spectrally resolved detector array (SRDA), and/or may include a conventional Bayer filter, CMYK filter, or any other absorption-based or interference-based filters. One type of interference based filter would be an array of thin film filters arranged in a grid with each element of the grid corresponding to one or more sensor elements. Another type of interference based filter is a Fabry-Pérot filter. Nanoetched interference Fabry-Pérot filters, which exhibit typical bandpass full-width-at-half-maxima (FWHM) on the order of 20 to 50 nm, are advantageous because they can be used in some embodiments due to the slow roll-off of the filters' passband seen in the transition from its center wavelength to its blocking band. These filters also exhibit a low OD in these blocking bands further enabling increased sensitivity to light outside of their passbands. These combined effects makes these specific filters sensitive to spectral regions that would otherwise be blocked by the fast roll-off of a high OD interference filter with a similar FWHM made with many thin film layers in a coating deposition process such as in evaporative deposition or in ion-beam sputtering. In embodiments with dye-based CMYK or RGB (Bayer) filter configurations, the slow spectral roll-off and the large FWHM of individual filter passbands are preferred and provide a unique spectral transmission percentage to individual wavelengths throughout an observed spectrum.

Accordingly, the datacube 120 that results from a snapshot imaging system will have one of two properties that can be problematic for precision imaging applications. As a first option, the datacube 120 that results from a snapshot imaging system can have smaller $N_x$ and $N_y$ sizes than the (x, y) size of the detector array and, thus be of lower resolution than the datacube 120, which would be generated by a scanning imaging system having the same image sensor. As a second option, the datacube 120 that results from a snapshot imaging system can have the same $N_x$ and $N_y$ sizes as the (x, y) size of the detector array due to interpolating values for certain (x, y) positions. However, the interpolation used to generate such a datacube means that certain values in the datacube are not actual measurements of the wavelength of light incident on the sensor, but rather estimates of what the actual measurement may be based on surrounding values.

Another existing option for single-exposure multispectral imaging is the multispectral beamsplitter. In such imaging systems, beamsplitter cubes split incident light into distinct color bands, with each band observed by independent image sensors. While one can change the beamsplitter designs to adjust the measured spectral bands, it is not easy to divide the incident light into more than four beams without compromising the system performance. Thus, four spectral channels appear to be the practical limit of this approach. A closely related method is to use thin-film filters instead of the bulkier beamsplitter cubes/prisms to split the light, however this approach is still limited to about six spectral channels due to space limitations and cumulative transmission losses through successive filters.

The aforementioned problems, among others, are addressed in some embodiments by the disclosed multi-aperture spectral imaging system with, multi-bandpass filters, preferably curved multi-bandpass filters, to filter light incoming through each aperture, and the associated image data processing techniques. This particular configuration is able to achieve all of the design goals of fast imaging speeds, high resolution images, and precise fidelity of detected wavelengths. Accordingly, the disclosed optical design and associated image data processing techniques can be used in portable spectral imaging systems and/or to image moving targets, while still yielding a datacube suitable for high precision applications (e.g., clinical tissue analysis, biometric recognition, transient clinical events). These higher precision applications may include the diagnosis of melanoma in the preceeding stages (0 through 3) before metastasis, the classification of a wound or burn severity on skin tissue, or the tissue diagnosis of diabetic foot ulcer severity. Accordingly, the small form factor and the snapshot spectral acquisition as depicted in some embodiments will enable the use of this invention in clinical environments with transient events, which include the diagnosis of several different retinopathies (e.g. non proliferative diabetic retinopathy, proliferative diabetic retinopathy, and age-related macular degeneration) and the imaging of moving pediatric patients. Accordingly, it will be appreciated by one of skill in the art that the use of a multi-aperture system with flat or curved multi-bandpass filters, as disclosed herein, represents a significant technological advance over prior spectral imaging implementations. Specifically, the multi-aperture system may enable the collection of 3D spatial images of or relating to object curvature, depth, volume, and/or area based on the calculated disparity of the perspective differences between each aperture. However, the multi-aperture strategies presented here are not limited to any specific filter and may include flat and/or thin filters, based on either interference or absorptive filtering. This invention, as disclosed herein, can be modified to include flat filters in the image space of the imaging system in the event of suitable lenses or apertures that use a small or acceptable range of incidence angles. Filters may also be placed at the aperture stop or at the entrance/exit pupil of the imaging lenses as one skilled in the art of optical engineering may see fit to do so.

Various aspects of the disclosure will now be described with regard to certain examples and embodiments, which are intended to illustrate but not limit the disclosure. Although the examples and embodiments described herein will focus, for the purpose of illustration, on specific calculations and algorithms, one of skill in the art will appreciate the examples are to illustrate only, and are not intended to be limiting. For example, although some examples are presented in the context of a multispectral imaging, the disclosed multi-aperture imaging system and associated filters can be configured to achieve hyperspectral imaging in other implementations. Further, although certain examples are presented as achieving benefits for handheld and/or moving target applications, it will be appreciated that the disclosed imaging system design and associated processing techniques can yield a high precision datacube suitable for fixed imaging systems and/or for analysis of relatively motionless targets.

Overview of Electromagnetic Ranges and Image Sensors

Certain colors or portions of the electromagnetic spectrum are referred to herein, and will now be discussed with respect to their wavelength as defined by the ISO 21348 definitions of irradiance spectral categories. As described further below, in certain imaging applications the wavelength ranges for specific colors can be grouped together to pass through a certain filter.

Electromagnetic radiation ranging from wavelengths of or approximately 760 nm to wavelengths of or approximately 380 nm are typically considered the "visible" spectrum, that is, the portion of the spectrum recognizable by the color receptors of the human eye. Within the visible spectrum, red light typically is considered to have a wavelength of or approximately 700 nanometers (nm), or to be in the range of or approximately 760 nm to 610 nm or approximately 610 nm. Orange light typically is considered to have a wavelength of or approximately 600 nm, or to be in the range of or approximately 610 nm to approximately 591 nm or 591 nm. Yellow light typically is considered to have a wavelength of or approximately 580 nm, or to be in the range of or approximately 591 nm to approximately 570 nm or 570nm. Green light typically is considered to have a wavelength of or approximately 550 nm, or to be in the range of or approximately 570 nm to approximately 500 nm or 500 nm. Blue light typically is considered to have a wavelength of or approximately 475 nm, or to be in the range of or approximately 500 nm to approximately 450 nm or 450 nm. Violet (purple) light typically is considered to have a wavelength of or approximately 400 nm, or to be in the range of or approximately 450 nm to approximately 360 nm or 360 nm.

Turning to ranges outside of the visible spectrum, infrared (IR) refers to electromagnetic radiation with longer wavelengths than those of visible light, and is generally invisible to the human eye. IR wavelengths extend from the nominal red edge of the visible spectrum at approximately 760 nm or 760 nm to approximately 1 millimeter (mm) or 1 mm. Within this range, near infrared (NIR) refers to the portion of the spectrum that is adjacent to the red range, ranging from wavelengths between approximately 760 nm or 760 nm to approximately 1400 nm or 1400 nm.

Ultraviolet (UV) radiation refers to some electromagnetic radiation with shorter wavelengths than those of visible light, and is generally invisible to the human eye. UV wavelengths extend from the nominal violet edge of the visible spectrum at approximately 40 nm or 40 nm to approximately 400 nm. Within this range, near ultraviolet (NUV) refers to the portion of the spectrum that is adjacent to the violet range, ranging from wavelengths between approximately 400 nm or 400 nm to approximately 300 nm or 300 nm, middle ultraviolet (MUV) ranges from wavelengths between approximately 300 nm or 300 nm to approximately 200 nm or 200 nm, and far ultraviolet (FUV) ranges from wavelengths between approximately 200 nm or 200 nm to approximately 122 nm or 122 nm.

The image sensors described herein can be configured to detect electromagnetic radiation in any of the above-described ranges, depending upon the particular wavelength ranges that are suitable for a particular application. The spectral sensitivity of a typical silicon-based charge-coupled device (CCD) or complementary metal-oxide-semiconductor (CMOS) sensor extends across the visible spectrum, and also extends considerably into the near-infrared (IR) spectrum and sometimes into the UV spectrum. Some implementations can alternatively or additionally use back-illuminated or front-illuminated CCD or CMOS arrays. For applications requiring high SNR and scientific-grade measurements, some implementations can alternatively or additionally use either scientific complementary metal-oxide-semiconductor (sCMOS) cameras or electron multiplying CCD cameras (EMCCD). Other implementations can alternatively or additionally use sensors known to operate in specific color ranges (e.g., short-wave infrared (SWIR), mid-wave infrared (MWIR), or long-wave infrared (LWIR)) and corresponding optical filter arryas, based on the intended applications. These may alternatively or additionally include cameras based around detector materials including indium gallium arsenide (InGaAs) or indium antimonide (InSb) or based around microbolometer arrays.

The image sensors used in the disclosed multispectral imaging techniques may be used in conjunction with an optical filter array such as a color filter array (CFA). Some CFAs can split incoming light in the visible range into red (R), green (G), and blue (B) categories to direct the split visible light to dedicated red, green, or blue photodiode receptors on the image sensor. A common example for a CFA is the Bayer pattern, which is a specific pattern for arranging RGB color filters on a rectangular grid of photosensors. The Bayer pattern is 50% green, 25% red and 25% blue with rows of repeating red and green color filters alternating with rows of repeating blue and green color filters. Some CFAs (e.g., for RGB-NIR sensors) can also separate out the NIR light and direct the split NIR light to dedicated photodiode receptors on the image sensor.

As such, the wavelength ranges of the filter components of the CFA can determine the wavelength ranges represented by each image channel in a captured image. Accordingly, a red channel of an image may correspond to the red wavelength regions of the color filter and can include some yellow and orange light, ranging from approximately 570 nm or 570 nm to approximately 760 nm or 760 nm in various embodiments. A green channel of an image may correspond to a green wavelength region of a color filter and can include some yellow light, ranging from approximately 570 nm or 570 nm to approximately 480 nm or 480 nm in various embodiments. A blue channel of an image may correspond to a blue wavelength region of a color filter and can include some violet light, ranging from approximately 490 nm or 490 nm to approximately 400 nm or 400 nm in various embodiments. As a person of ordinary skill in the art will appreciate, exact beginning and ending wavelengths (or portions of the electromagnetic spectrum) that define colors of a CFA (for example, red, green, and blue) can vary depending upon the CFA implementation.

Further, typical visible light CFAs are transparent to light outside the visible spectrum. Therefore, in many image sensors the IR sensitivity is limited by a thin-film reflective IR filter at the face of the sensor that blocks the infrared wavelength while passing visible light. However, this may be omitted in some of the disclosed imaging systems to allow of passage of IR light. Thus, the red, green, and/or blue channels may also be used to collect IR wavelength bands. In some implementations the blue channel may also be used to collect certain NUV wavelength bands. The distinct spectral responses of the red, green, and blue channels with regard to their unique transmission efficiencies at each wavelength in a spectral image stack may provide a uniquely weighted response of spectral bands to be unmixed using the known transmission profiles. For example, this may include the known transmission response in IR and UV wavelength regions for the red, blue, and green channels, enabling their use in the collection of bands from these regions.

As described in further detail below, additional color filters can be placed before the CFA along the path of light towards the image sensor in order to selectively refine the specific bands of light that become incident on the image sensor. Some of the disclosed filters can be either a combination of dichroic (thin-film) and/or absorptive filters or a single dichroic and/or absorptive filter. Some of the disclosed color filters can be bandpass filters that pass frequencies within a certain range (in a passband) and reject (attenuates) frequencies outside that range (in a blocking range). Some of the disclosed color filters can be multi-bandpass filters that pass multiple discontinuous ranges of wavelengths. These "wavebands" can have smaller passband ranges, larger blocking range attenuation, and sharper spectral roll-off, which is defined as the steepness of the spectral response as the filter transitions from the passband to the blocking range, than the larger color range of the CFA filter. For example, these disclosed color filters can cover a passband of approximately 20 nm or 20 nm or approximately 40 nm or 40 nm. The particular configuration of such color filters can determine the actual wavelength bands that are incident upon the sensor, which can increase the precision of the disclosed imaging techniques. The color filters described herein can be configured to selectively block or pass specific bands of electromagnetic radiation in any of the above-described ranges, depending upon the particular wavelength bands that are suitable for a particular application.

As described herein, a "pixel" can be used to describe the output generated by an element of the 2D detector array. In comparison, a photodiode, a single photosensitive element in this array, behaves as a transducer capable of converting photons into electrons via the photoelectric effect, which is then in turn converted into a usable signal used to determine the pixel value. A single element of the datacube can be referred to as a "voxel" (e.g., a volume element). A "spectral vector" refers to a vector describing the spectral data at a particular (x, y) position in a datacube (e.g., the spectrum of light received from a particular point in the object space). A single horizontal plane of the datacube (e.g., an image representing a single spectral dimension), is referred to herein as a an "image channel". Certain embodiments described herein may capture spectral video information, and the resulting data dimensions can assume the "hypercube" form $N_x N_y N_\lambda N_t$, where $N_t$ is the number of frames captured during a video sequence.

Figure 3A:
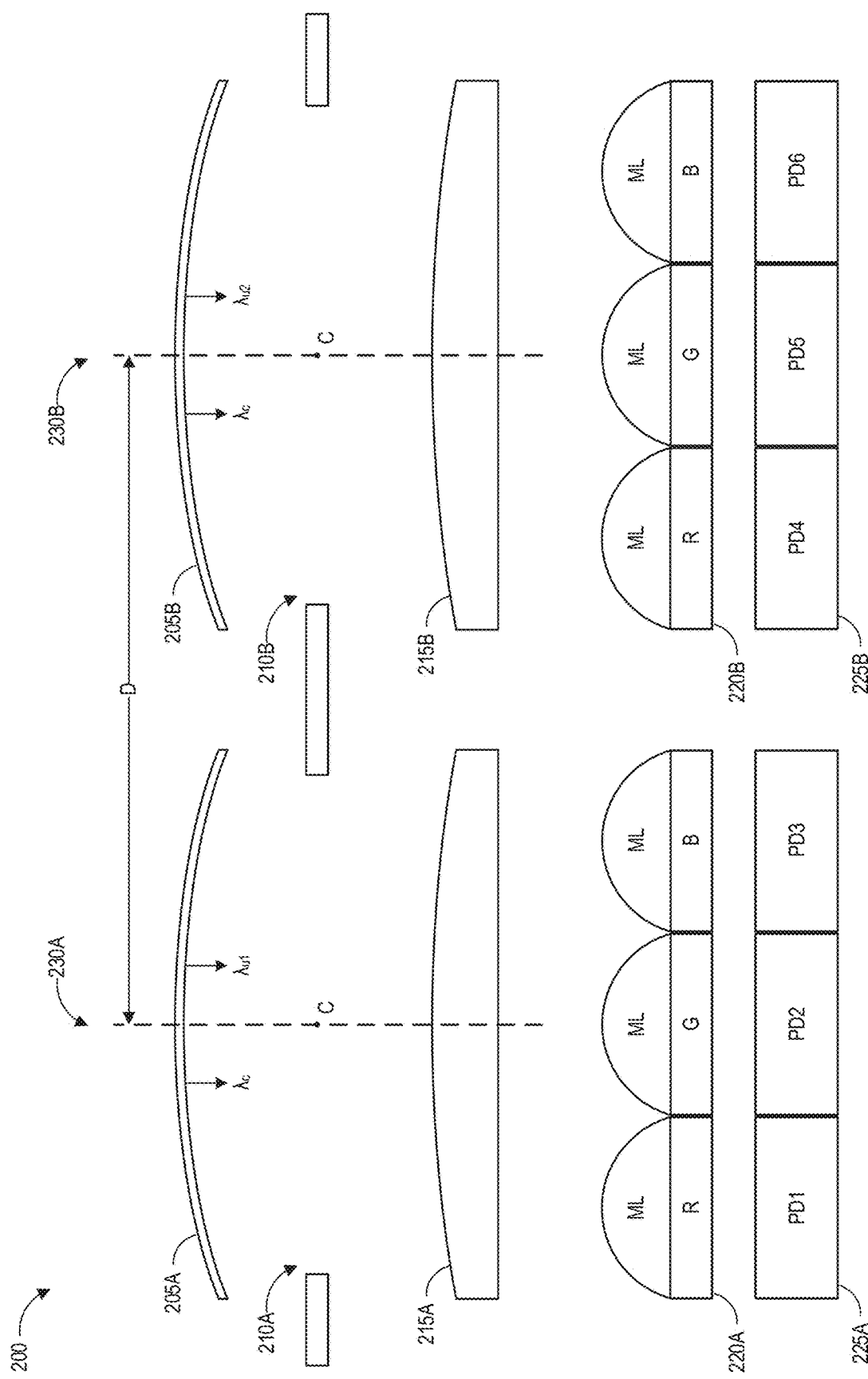
FIG. 3A depicts a schematic cross-sectional view of an optical design of an example multi-aperture imaging system with curved multi-bandpass filters, according to the present disclosure.

Overview of Example Multi-Aperture Imaging Systems with Curved Multi-Bandpass Filters FIG. 3A depicts a schematic view of an example multi-aperture imaging system 200 with curved multi-bandpass filters, according to the present disclosure. The illustrated view includes a first image sensor region 225A (photodiodes PD1-PD3) and a second image sensor region 225B (photodiodes PD4-PD6). The photodiodes PD1-PD6 can be, for example, photodiodes formed in a semiconductor substrate, for example in a CMOS image sensor. Generally, each of the photodiodes PD1-PD6 can be a single unit of any material, semiconductor, sensor element or other device that converts incident light into current. It will be appreciated that a small portion of the overall system is illustrated for the purpose of explaining its structure and operation, and that in implementation image sensor regions can have hundreds or thousands of photodiodes (and corresponding color filters). The image sensor regions 225A and 225B may be implemented as separate sensors, or as separate regions of the same image sensor, depending upon the implementation. Although FIG. 3A depicts two apertures and corresponding light paths and sensor regions, it will be appreciated that the optical design principles illustrated by FIG. 3A can be extended to three or more apertures and corresponding light paths and sensor regions, depending upon the implementation.

The multi-aperture imaging system 200 includes a first opening 210A that provides a first light path towards the first sensor region 225A, and a second opening 210B that provides a first light path towards the second sensor region 225B. These apertures may be adjustable to increase or decrease the brightness of the light that falls on the image, or so that the duration of particular image exposures can be changed and the brightness of the light that falls on the image sensor regions does not change. These apertures may also be located at any position along the optical axes of this multi-aperture system as deemed reasonable by one skilled in the art of optical design. The optical axis of the optical components positioned along the first light path is illustrated by dashed line 230A and the optical axis of the optical components positioned along the second light path is illustrated by dashed line 230B, and it will be appreciated that these dashed lines do not represent a physical structure of the multi-aperture imaging system 200. The optical axes 230A, 230B are separated by a distance D, which can result in disparity between the images captured by the first and second sensor regions 225A, 225B. Disparity refers to the distance between two corresponding points in the left and right (or upper and lower) images of a stereoscopic pair, such that the same physical point in the object space can appear in different locations in each image. Processing techniques to compensate for and leverage this disparity are described in further detail below.

Each optical axis 230A, 230B passes through a center C of the corresponding aperture, and the optical components can also be centered along these optical axes (e.g., the point of rotational symmetry of an optical component can be positioned along the optical axis). For example, the first curved multi-bandpass filter 205A and first imaging lens 215A can be centered along the first optical axis 230A, and the second curved multi-bandpass filter 205B and second imaging lens 215B can be centered along the second optical axis 230B.

As used herein with respect to positioning of optical elements, "over" and "above" refer to the position of a structure (for example, a color filter or lens) such that light entering the imaging system 200 from the object space propagates through the structure before it reaches (or is incident upon) another structure. To illustrate, along the first light path, the curved multi-bandpass filter 205A is positioned above the aperture 210A, the aperture 210A is positioned above imaging lens 215A, the imaging lens 215A is positioned above the CFA 220A, and the CFA 220A is positioned above the first image sensor region 225A. Accordingly, light from the object space (e.g., the physical space being imaged) first passes through the curved multi-bandpass filter 205A, then the aperture 210A, then the imaging lens 215A, then the CFA 220A, and finally is incident on the first image sensor region 225A. The second light path (e.g., curved multi-bandpass filter 205B, aperture 210B, imaging lens 215B, CFA 220B, second image sensor region 225B) follows a similar arrangement. In other implementations, the aperture 210A, 210B and/or imaging lenses 215A, 215B can be positioned above the curved multi-bandpass filter 205A, 205B. Additionally, other implementations may not use a physical aperture and may rely on the clear aperture of the optics to control the brightness of light that is imaged onto the sensor region 225A, 225B. Accordingly, the lens 215A, 215B may be placed above the aperture 210A, 210B and curved multi-bandpass filter 205A, 205B. In this implementation, the aperture 210A, 210B and lens 215A, 215B may be also be placed over or under each other as deemed necessary by one skilled in the art of optical design.

The first CFA 220A positioned over the first sensor region 225A and the second CFA 220B positioned over the second sensor region 225B can act as wavelength-selective pass filters and split incoming light in the visible range into red, green, and blue ranges (as indicated by the R, G, and B notation). The light is "split" by allowing only certain selected wavelengths to pass through each of the color filters in the first and second CFAs 220A, 220B. The split light is received by dedicated red, green, or blue diodes on the image sensor. Although red, blue, and green color filters are commonly used, in other embodiments the color filters can vary according to the color channel requirements of the captured image data, for example including ultraviolet, infrared, or near-infrared pass filters, as with an RGB-IR CFA.

As illustrated, each filter of the CFA is positioned over a single photodiode PD1-PD6. FIG. 3A also illustrates example microlenses (denoted by ML) that can be formed on or otherwise positioned over each color filter, in order to focus incoming light onto active detector regions. Other implementations may have multiple photodiodes under a single filter (e.g., clusters of 2, 4, or more adjacent photodiodes). In the illustrated example, photodiode PD1 and photodiode PD4 are under red color filters and thus would output red channel pixel information; photodiode PD2 and photodiode PD5 are under green color filters and, thus would output green channel pixel information; and photodiode PD3 and photodiode PD6 are under blue color filters and thus would output blue channel pixel information. Further, as described in more detail below, the specific color channels output by given photodiodes can be further limited to narrower wavebands based on activated illuminants and/or the specific wavebands passed by the multi-bandpass filters 205A, 205B, such that a given photodiode can output different image channel information during different exposures.

The imaging lenses 215A, 215B can be shaped to focus an image of the object scene onto the sensor regions 225A, 225B. Each imaging lens 215A, 215B may be composed of as many optical elements and surfaces needed for image formation and are not limited to single convex lenses as presented in FIG. 3A, enabling the use of a wide variety of imaging lenses or lens assemblies that would be available commercially or by custom design. Each element or lens assembly may be formed or bonded together in a stack or held in series using an optomechanical barrel with a retaining ring or bezel. In some embodiments, elements or lens assemblies may include one or more bonded lens groups, such as two or more optical components cemented or otherwise bonded together. In various embodiments, any of the multi-bandpass filters described herein may be positioned in front of a lens assembly of the multispectral image system, in front of a singlet of the multispectral image system, behind a lens assembly of the multispectral image system, behind a singlet of the multispectral image system, inside a lens assembly of the multispectral image system, inside a bonded lens group of the multispectral image system, directly onto a surface of a singlet of the multispectral image system, or directly onto a surface of an element of a lens assembly of the multispectral image system. Further, the aperture 210A and 210B may be removed, and the lenses 215A, 215B may be of the variety typically used in photography with either digital-single-lens-reflex (DSLR) or mirrorless cameras. Additionally, these lenses may be of the variety used in machine vision using C-mount or S-mount threading for mounting. Focus adjustment can be provided by movement of the imaging lenses 215A, 215B relative to the sensor regions 225A, 225B or movement of the sensor regions 225A, 225B relative to the imaging lenses 215A, 215B, for example based on manual focusing, contrast-based autofocus, or other suitable autofocus techniques.

The multi-bandpass filters 205A, 205B can be each configured to selectively pass multiple narrow wavebands of light, for example wavebands of 10-50 nm in some embodiments (or wider or narrower wavebands in other embodiments). As illustrated in FIG. 3A, both multi-bandpass filters 205A, 205B can pass waveband $\lambda_c$ (the "common waveband"). In implementations with three or more light paths, each multi-bandpass filter can pass this common waveband. In this manner, each sensor region captures image information at the same waveband (the "common channel"). This image information in this common channel can be used to register the sets of images captured by each sensor region, as described in further detail below. Some implementations may have one common waveband and corresponding common channel, or may have multiple common wavebands and corresponding common channels.

In addition to the common waveband $\lambda_c$, each multi-bandpass filters 205A, 205B can be each configured to selectively pass one or more unique wavebands. In this manner, the imaging system 200 is able to increase the number of distinct spectral channels captured collectively by the sensor regions 205A, 205B beyond what can be captured by a single sensor region. This is illustrated in FIG. 3A by multi-bandpass filters 205A passing unique waveband $\lambda_{u1}$, and multi-bandpass filters 205B passing unique waveband $\lambda_{u2}$, where $\lambda_{u1}$ and $\lambda_{u2}$ represent different wavebands from one another. Although depicted as passing two wavebands, the disclosed multi-bandpass can each pass a set of two or more wavebands. For example, some implementations can pass four wavebands each, as described with respect to FIGS. 11A and 11B. In various embodiments, a larger number of wavebands may be passed. For example, some four-camera implementations may include multi-bandpass filters configured to pass 8 wavebands. In some embodiments, the number of wavebands may be, for example, 4, 5, 6, 7, 8, 9, 10, 12, 15, 16, or more wavebands.

The multi-bandpass filters 205A, 205B have a curvature selected to reduce the angular-dependent spectral transmission across the respective sensor regions 225A, 225B. As a result, when receiving narrowband illumination from the object space, each photodiode across the area of the sensor regions 225A, 225B that is sensitive to that wavelength (e.g., the overlying color filter passes that wavelength) should receive substantially the same wavelength of light, rather than photodiodes near the edge of the sensor experiencing the wavelength shift described above with respect to FIG. 1A. This can generate more precise spectral image data than using flat filters.

FIG. 3B depicts an example optical design for optical components of one light path of the multi-aperture imaging system of FIG. 3A. Specifically, FIG. 3B depicts a custom achromatic doublet 240 that can be used to provide the multi-bandpass filters 205A, 205B. The custom achromatic doublet 240 passes light through a housing 250 to an image sensor 225. The housing 250 can include openings 210A, 210B and imaging lens 215A, 215B described above.

The achromatic doublet 240 is configured to correct for optical abberations as introduced by the incorporation of surfaces required for the multi-bandpass filter coatings 205A, 205B. The illustrated achromatic doublet 240 includes two individual lenses, which can be made from glasses or other optical materials having different amounts of dispersion and different refractive indicies. Other implementations may use three or more lenses. These achromatic doublet lenses can be designed to incorporate the multi-bandpass filter coatings 205A, 205B on the curved front surface 242 while eliminating optical aberrations introduced that would otherwise be present through the incorporation of a curved singlet optical surface with the deposited filter coatings 205A, 205B while still limiting optical or focusing power provided by the achromatic doublet 240 due to the combinatorial effect of the curved front surface 242 and the curved back surface of 244 while still keeping the primary elements for focusing light restricted to the lenses housed in housing 250. Thus, the achromatic doublet 240 can contribute to the high precision of image data captured by the system 200. These individual lenses can be mounted next to each other, for example being bonded or cemented together, and shaped such that the aberration of one of the lenses is counterbalanced by that of the other. The achromatic doublet 240 curved front surface 242 or the curved back surface 244 can be coated with the multi-bandpass filter coating 205A, 205B. Other doublet designs may be implemented with the systems described herein.

Figure 3C:
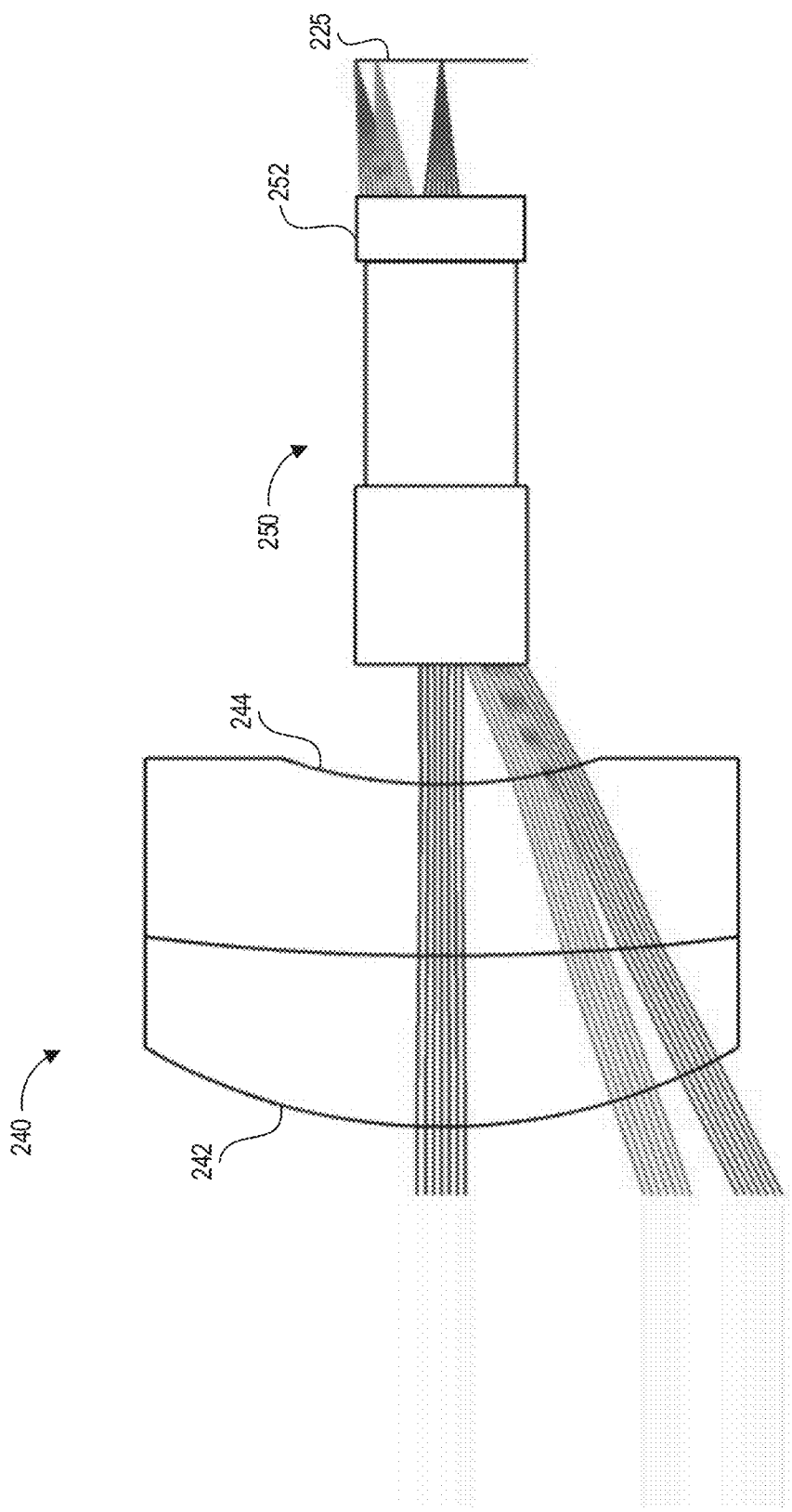
Figure 3D:
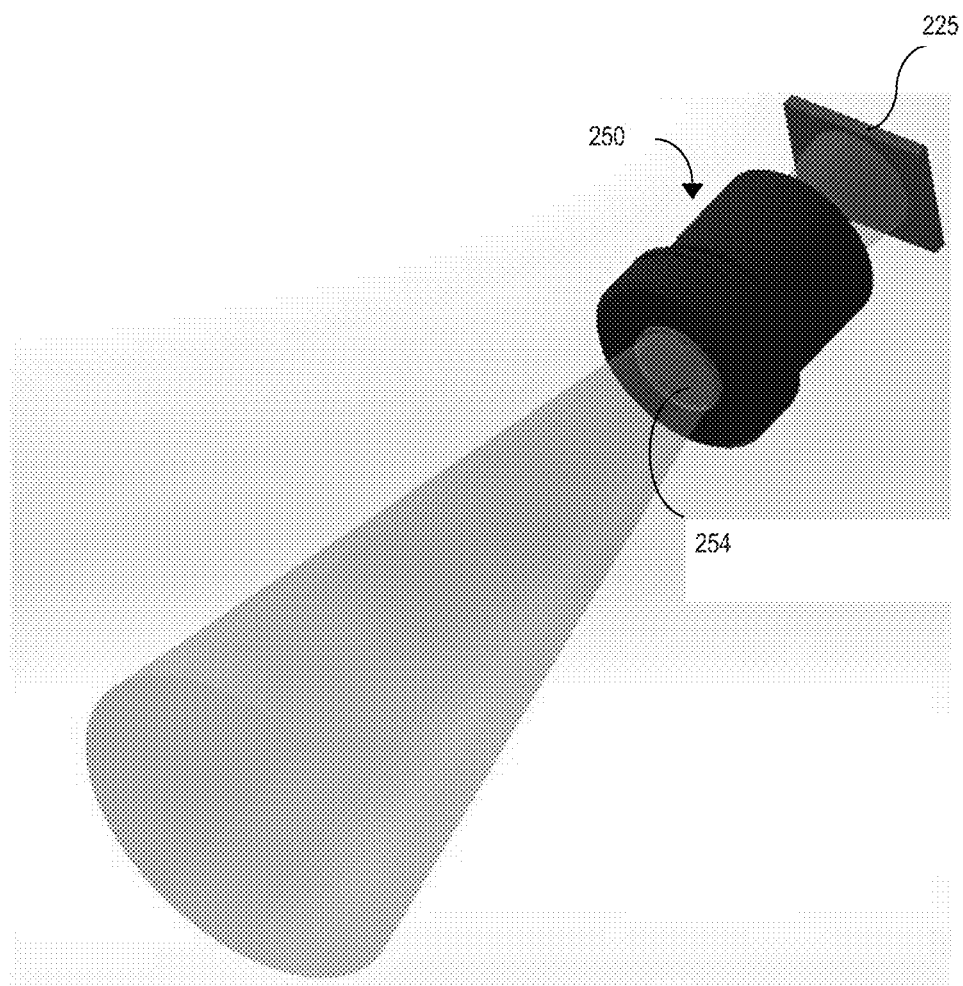

Further variations of the optical designs described herein may be implemented. For example, in some embodiments a light path may include a singlet or other optical singlet such as of the positive or negative meniscus variety as depicted in FIG. 3A instead of the doublet 240 depicted in FIG. 3B. FIG. 3C illustrates an example implementation in which a flat filter 252 is included between the lens housing 250 and the sensor 225. The achromatic doublet 240 in FIG. 3C provides optical aberration correction as introduced by the inclusion of the flat filter 252 containing a multi-bandpass transmission profile while not significantly contributing to the optical power as provided by the lenses contained in housing 250. FIG. 3D illustrates another example of an implementation in which the multi-bandpass coating is implemented by means of a multi-bandpass coating 254 applied to the front surface of the lens assembly contained within the housing 250. As such, this multi-bandpass coating 254 may be applied to any curved surface of any optical element residing within housing 250.

Figure 4A:
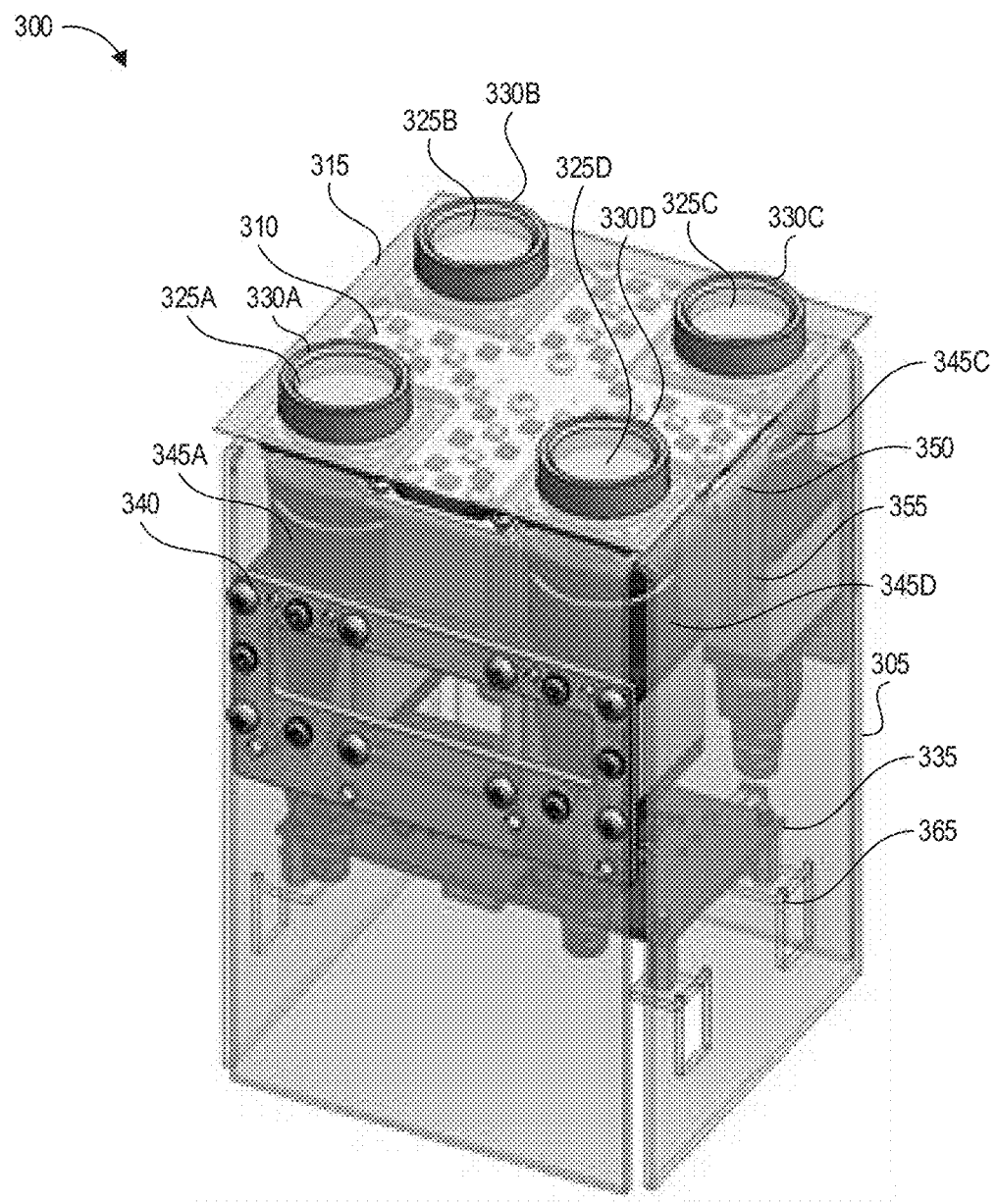
FIGS. 4A-4E depict an embodiment of a multispectral multi-aperture imaging system, with an optical design as described with respect to FIGS. 3A and 3B.
Figure 4C:
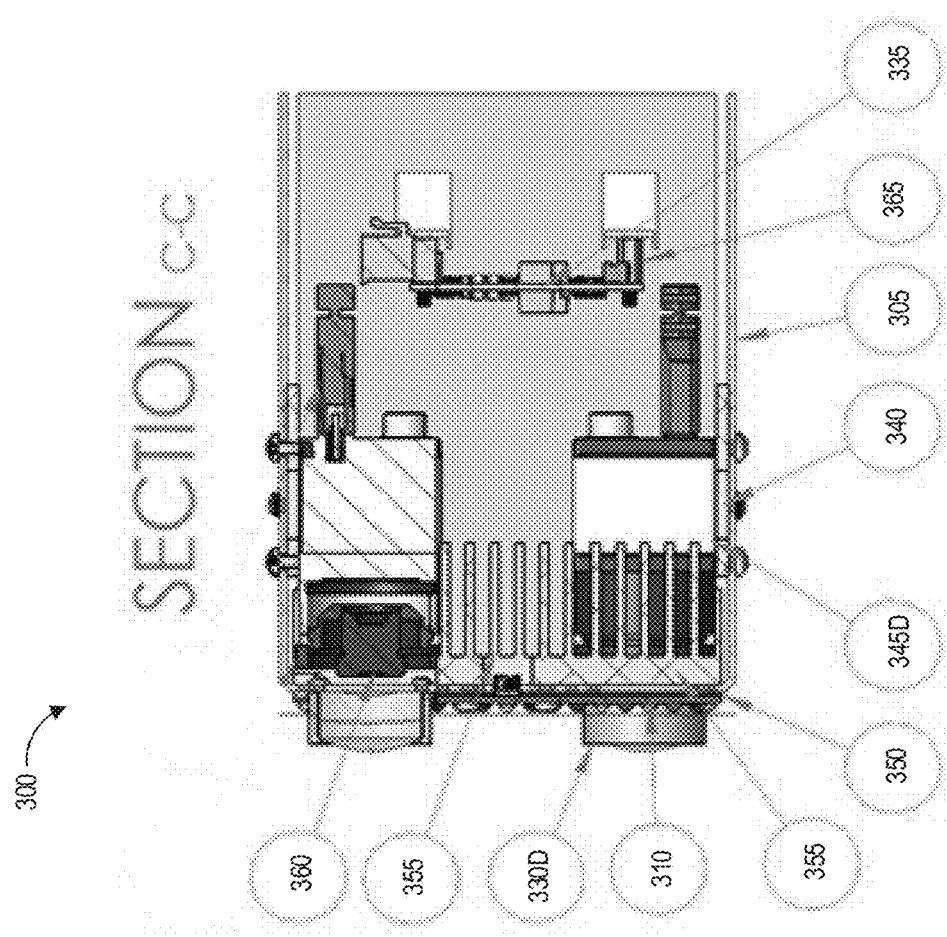
Figure 4B:
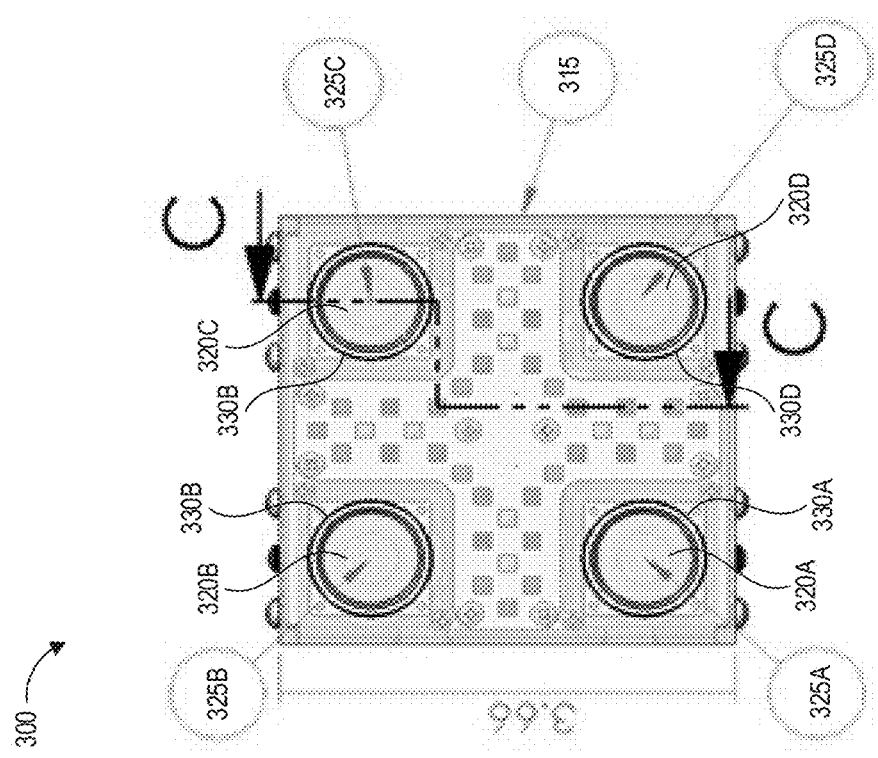
Figure 4E:
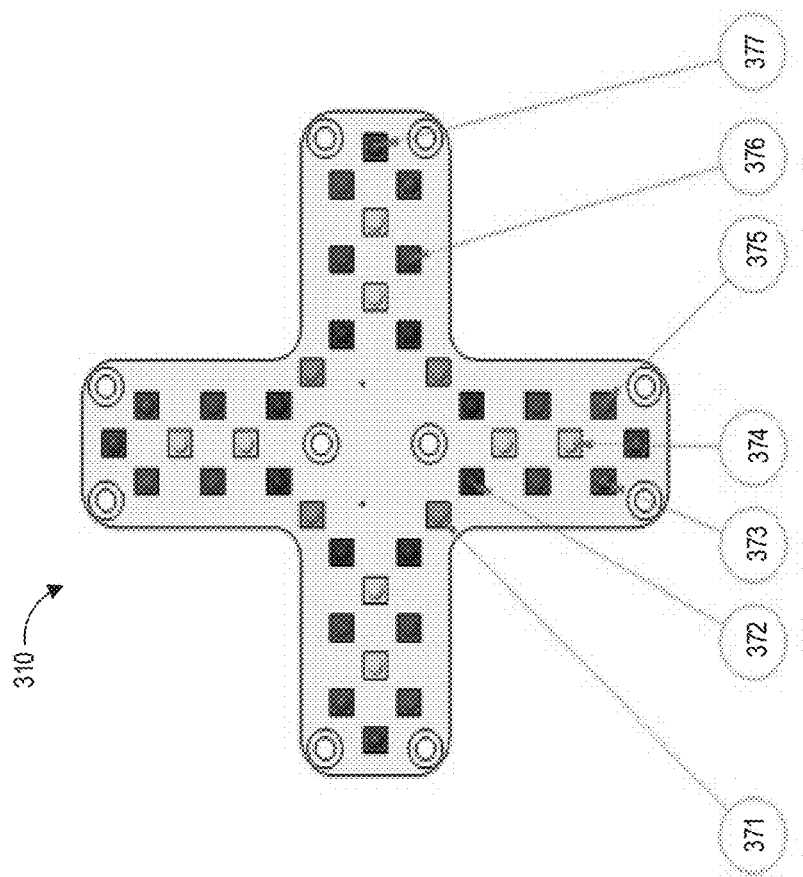
Figure 4D:
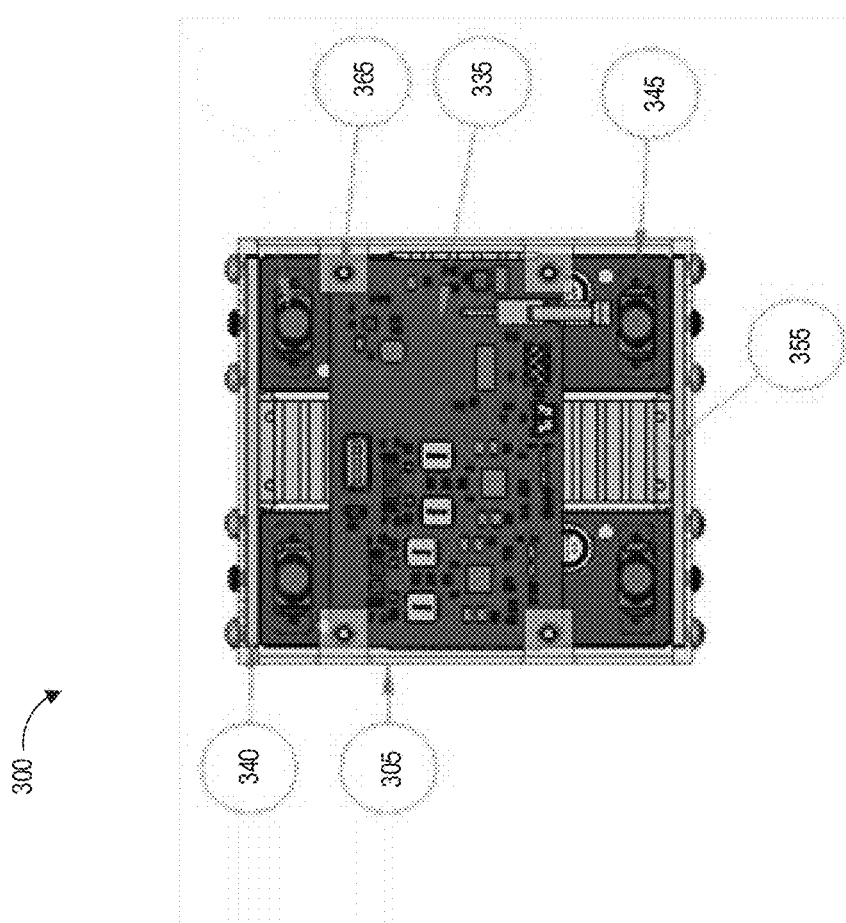

FIGS. 4A-4E depict an embodiment of a multispectral, multi-aperture imaging system 300, with an optical design as described with respect to FIGS. 3A and 3B. Specifically, FIG. 4A depicts a perspective view of the imaging system 300 with the housing 305 illustrated with translucency to reveal interior components. The housing 305 may be larger or smaller relative to the illustrated housing 305, for example, based on a desired amount of embedded computing resources. FIG. 4B depicts a front view of the imaging system 300. FIG. 4C depicts a cutaway side view of the imaging system 300, cut along line C-C illustrated in FIG. 4B. FIG. 4D depicts a bottom view of the imaging system 300 depicting the processing board 335. FIGS. 4A-4D are described together below.

Figures 19A, 19B:
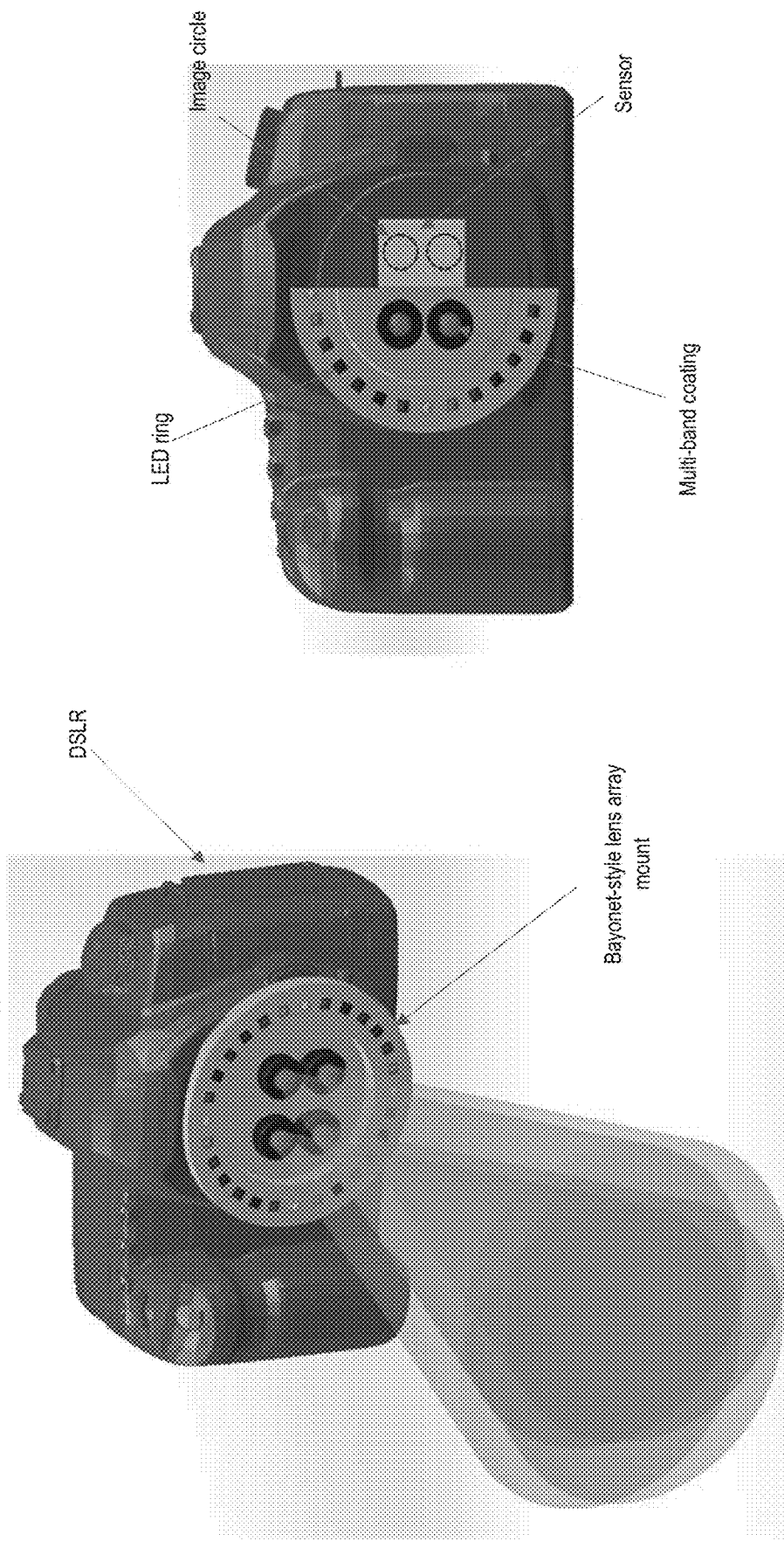
FIGS. 19A and 19B illustrate an example handheld embodiment of a multispectral, multi-aperture imaging system.
Figure 20A:
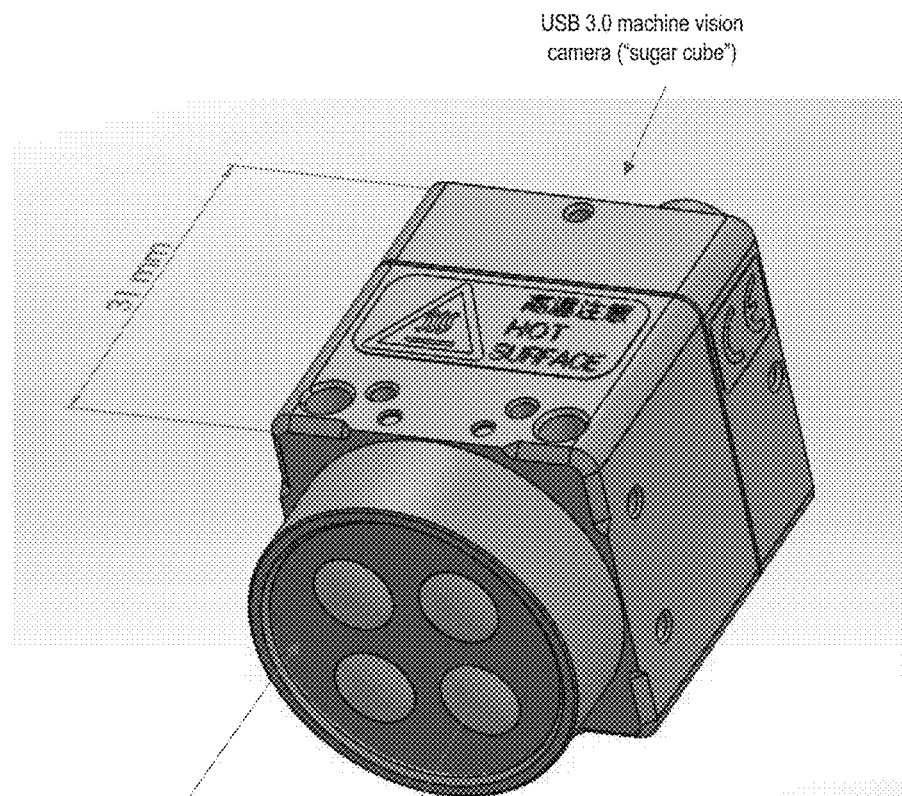
FIGS. 20A and 20B illustrate an example multispectral, multi-aperture imaging system for a small USB 3.0 enclosed in a common camera housing.
Figure 20B:
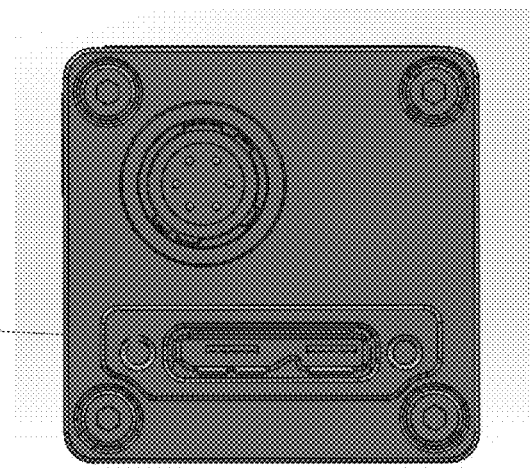

The housing 305 of the imaging system 300 may be encased in another housing. For example, handheld implementations may enclose the system within a housing optionally with one or more handles shaped to facilitate stable holding of the imaging system 300. Example handheld implementations are depicted in greater detail in FIGS. 18A-18C and in FIGS. 19A-19B. The upper surface of the housing 305 includes four openings 320A-320D. A different multi-bandpass filter 325A-325D is positioned over each opening 320A-320D and held in place by a filter cap 330A-330B. The multi-bandpass filters 325A-325D may or may not be curved, and each pass a common waveband and at least one unique waveband, as described herein, in order to achieve high precision multi-spectral imaging across a greater number of spectral channels than would otherwise be captured by the image sensor due to its overlying color filter array. The image sensor, imaging lenses, and color filters described above are positioned within the camera housings 345A-345D. In some embodiments, a single camera housing may enclose the image sensors, imaging lenses, and color filters described above, for example, as shown in FIGS. 20A-20B. In the depicted implementation separate sensors are thus used (e.g., one sensor within each camera housing 345A-345D), but it will be appreciated that a single image sensor spanning across all of the regions exposed through the openings 320A-320D could be used in other implementations. The camera housings 345A-345D are secured to the system housing 305 using supports 340 in this embodiment, and can be secured using other supports in various implementations.

The upper surface of the housing 305 supports an optional illumination board 310 covered by an optical diffusing element 315. The illumination board 310 is described in further detail with respect to FIG. 4E, below. The diffusing element 315 can be composed of glass, plastic, or other optical material for diffusing light emitted from the illumination board 310 such that the object space receives substantially spatially-even illumination. Even illumination of the target object can be beneficial in certain imaging applications, for example clinical analysis of imaged tissue, because it provides, within each wavelength, a substantially even amount of illumination across the object surface. In some embodiments, the imaging systems disclosed herein may utilize ambient light instead of or in addition to light from the optional illumination board.

Due to heat generated by the illumination board 310 in use, the imaging system 300 includes a heat sink 350 including a number of heat dissipating fins 355. The heat dissipating fins 355 can extend into the space between the camera housings 345A-345D, and the upper portion of the heat sink 350 can draw heat from the illumination board 310 to the fins 355. The heat sink 350 can be made from suitable thermally conductive materials. The heat sink 350 may further help to dissipate heat from other components such that some implementations of imaging systems may be fanless.

A number of supports 365 in the housing 305 secure a processing board 335 in communication with the cameras 345A-345D. The processing board 335 can control operation of the imaging system 300. Although not illustrated, the imaging system 300 can also be configured with one or more memories, for example storing data generated by use of the imaging system and/or modules of computer-executable instructions for system control. The processing board 335 can be configured in a variety of ways, depending upon system design goals. For example, the processing board can be configured (e.g., by a module of computer-executable instructions) to control activation of particular LEDs of the illumination board 310. Some implementations can use a highly stable synchronous step-down LED driver, which can enable software control of analog LED current and also detect LED failure. Some implementations can additionally provide image data analysis functionality to the processing board (e.g., by modules of computer-executable instructions) 335 or to a separate processing board. Although not illustrated, the imaging system 300 can include data interconnects between the sensors and the processing board 335 such that the processing board 335 can receive and process data from the sensors, and between the illumination board 310 and the processing board 335 such that the processing board can drive activation of particular LEDs of the illumination board 310.

FIG. 4E depicts an example illumination board 310 that may be included in the imaging system 300, in isolation from the other components. The illumination board 310 includes four arms extending from a central region, with LEDs positioned along each arm in three columns. The spaces between LEDs in adjacent columns are laterally offset from one another to create separation between adjacent LEDs. Each column of LEDs includes a number of rows having different colors of LEDs. Four green LEDs 371 are positioned in the center region, with one green LED in each corner of the center region. Starting from the innermost row (e.g., closest to the center), each column includes a row of two deep red LEDs 372 (for a total of eight deep red LEDs). Continuing radially outward, each arm has a row of one amber LED 374 in the central column, a row of two short blue LEDs 376 in the outermost columns (for a total of eight short blue LEDs), another row of one amber LED 374 in the central column (for a total of eight amber LEDs), a row having one non-PPG NIR LED 373 and one red LED 375 in the outermost columns (for a total of four of each), and one PPG NIR LED 377 in the central column (for a total of four PPG NIR LEDs). A "PPG" LED refers to an LED activated during a number of sequential exposure for capturing photoplethysmographic (PPG) information representing pulsatile blood flow in living tissue. It will be understood that a variety of other colors and/or arrangements thereof may be used in illumination boards of other embodiments.

FIG. 5 depicts another embodiment of a multispectral multi-aperture imaging system, with an optical design as described with respect to FIGS. 3A and 3B. Similar to the design of the imaging system 300, the imaging system 400 includes four light paths, here shown as openings 420A-420D having multi-bandpass filter lens groups 425A-425D, which are secured to housing 405 by retaining rings 430A-430D. The imaging system 400 also includes an illumination board 410 secured to the front face of the housing 405 between the retaining rings 430A-430D, and a diffuser 415 positioned over the illumination board 410 to assist with emitting spatially even light onto the target object.

The illumination board 410 of the system 400 includes four branches of LEDs in a cross shape, with each branch including two columns of closely-spaced LEDs. Thus, the illumination board 410 is more compact than the illumination board 310 described above, and may be suitable for use with imaging systems having smaller form factor requirements. In this example configuration, each branch includes an outermost row having one green LED and one blue LED, and moving inwards includes two rows of yellow LEDs, a row of orange LEDs, a row having one red LED and one deep red LED, and a row having one amber LED and one NIR LED. Accordingly, in this implementation the LEDs are arranged such that LEDs that emit light of longer wavelengths are in the center of the illumination board 410, while LEDs that emit light of shorter wavelengths are at the edges of the illumination board 410.

Figure 6A:
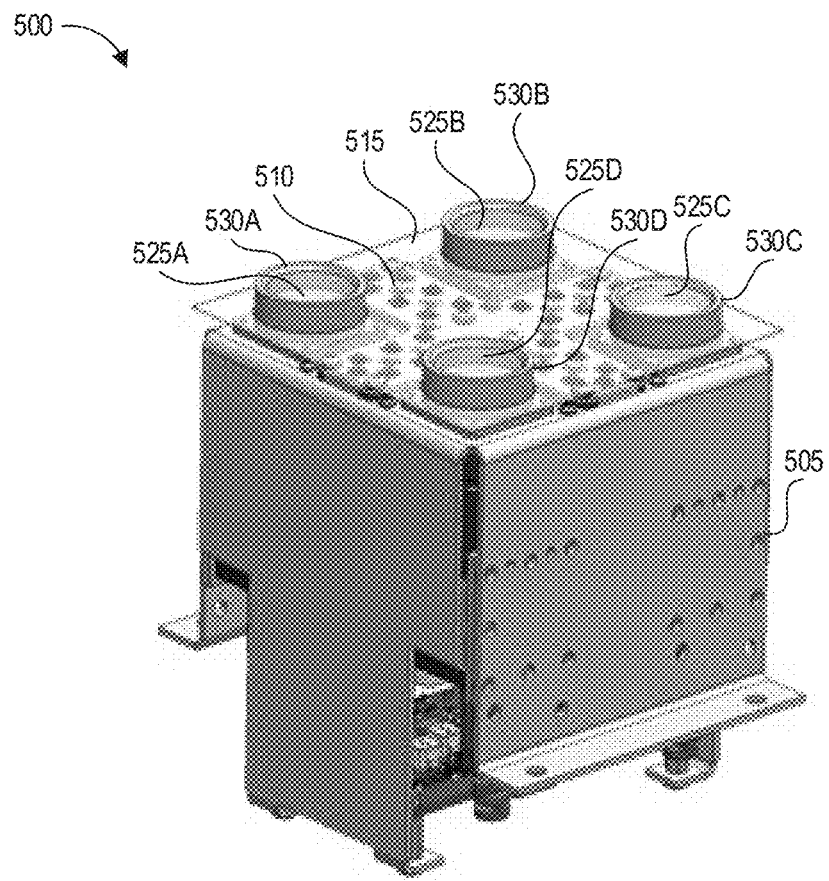
FIGS. 6A-6C depict another embodiment of a multispectral multi-aperture imaging system, with an optical design as described with respect to FIGS. 3A and 3B.
Figure 6C:
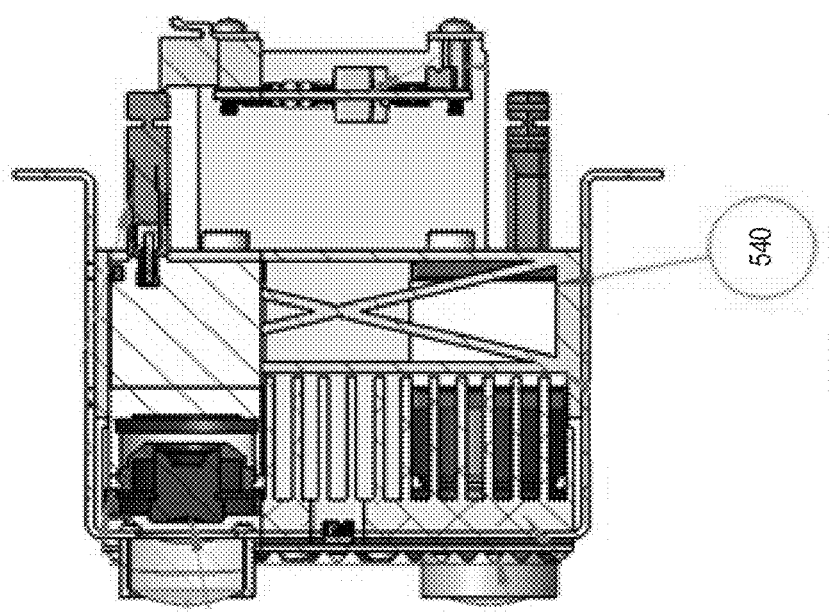
Figure 6B:
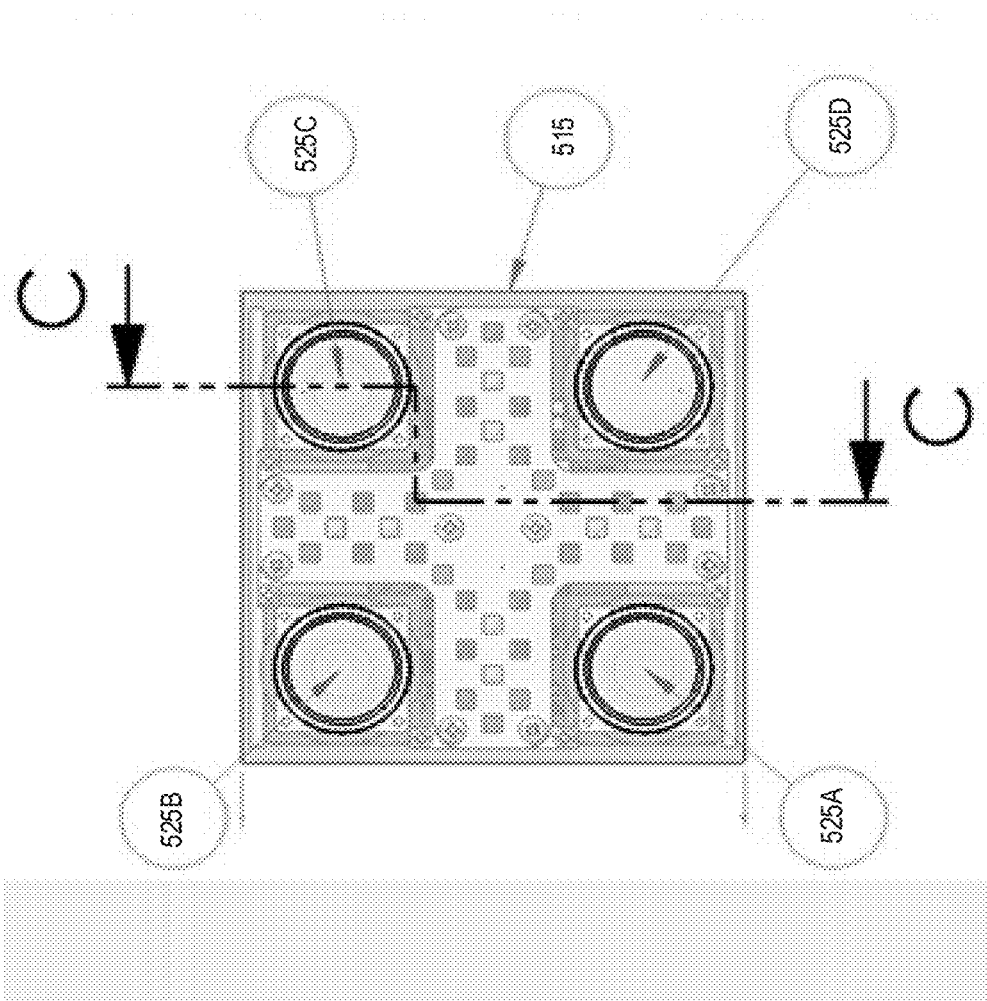

FIGS. 6A-6C depict another embodiment of a multispectral multi-aperture imaging system 500, with an optical design as described with respect to FIGS. 3A and 3B. Specifically, FIG. 6A depicts a perspective view of the imaging system 500, FIG. 6B depicts a front view of the imaging system 500, and FIG. 6C depicts a cutaway side view of the imaging system 500, cut along line C-C illustrated in FIG. 6B. The imaging system 500 includes similar components to those described above with respect to imaging system 300 (e.g., a housing 505, illumination board 510, diffusing plate 515, multi-bandpass filters 525A-525D secured over openings via retaining rings 530A-530D), but depicts a shorter form factor (e.g., in an embodiment with fewer and/or smaller embedded computing components). The system 500 also includes a direct camera-to-frame mount 540 for added rigidity and robustness of camera alignment.

Figure 7B:
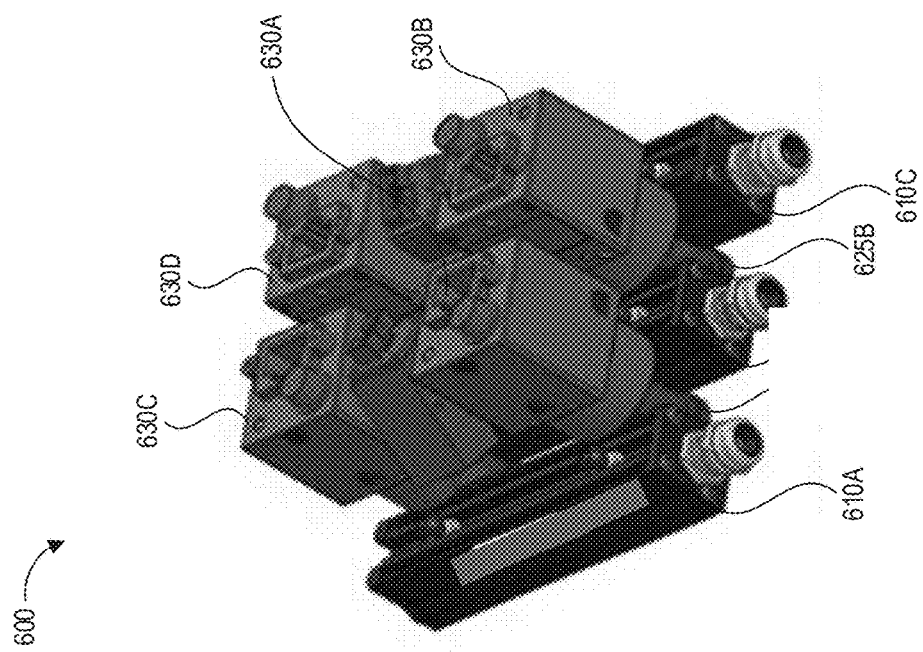
FIGS. 7A-7B depict another embodiment of a multispectral multi-aperture imaging system, with an optical design as described with respect to FIGS. 3A and 3B.
Figure 7A:
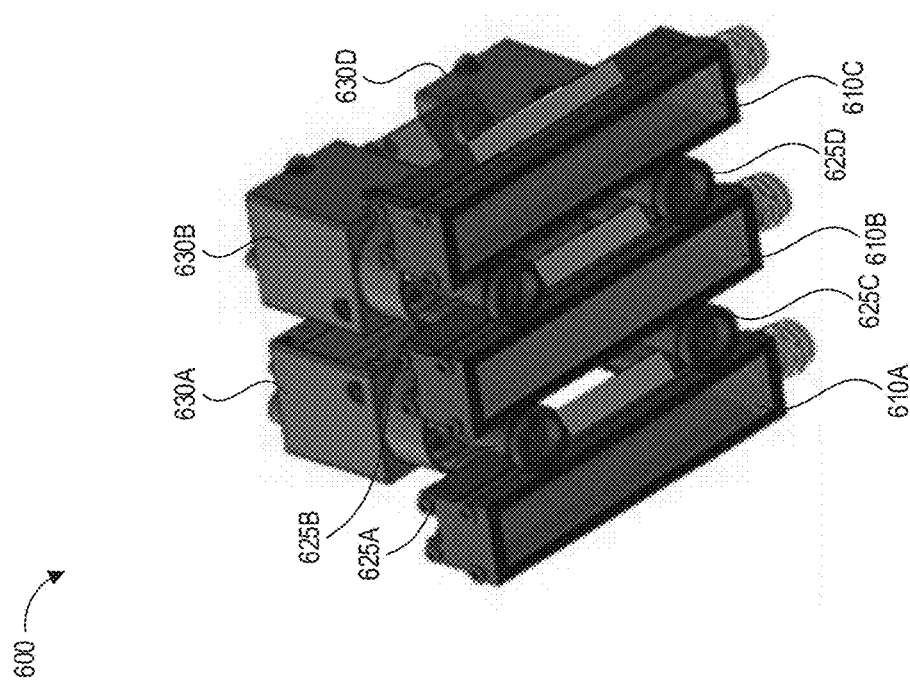

FIGS. 7A-7B depict another embodiment of a multispectral multi-aperture imaging system 600. FIGS. 7A-7B illustrate another possible arrangement of light sources 610A-610C around a multi-aperture imaging system 600. As depicted, four lens assemblies with multi-bandpass filters 625A-625D with an optical design as described with respect to FIGS. 3A-3D can be disposed in a rectangular or square configuration to provide light to four cameras 630A-630D (including image sensors). Three rectangular light emitting elements 610A-610C can be disposed parallel to one another outside of and between the lens assemblies with multi-bandpass filters 625A-625D. These can be broad-spectrum light emitting panels or arrangements of LEDs that emit discrete wavebands of light.

Figure 8B:
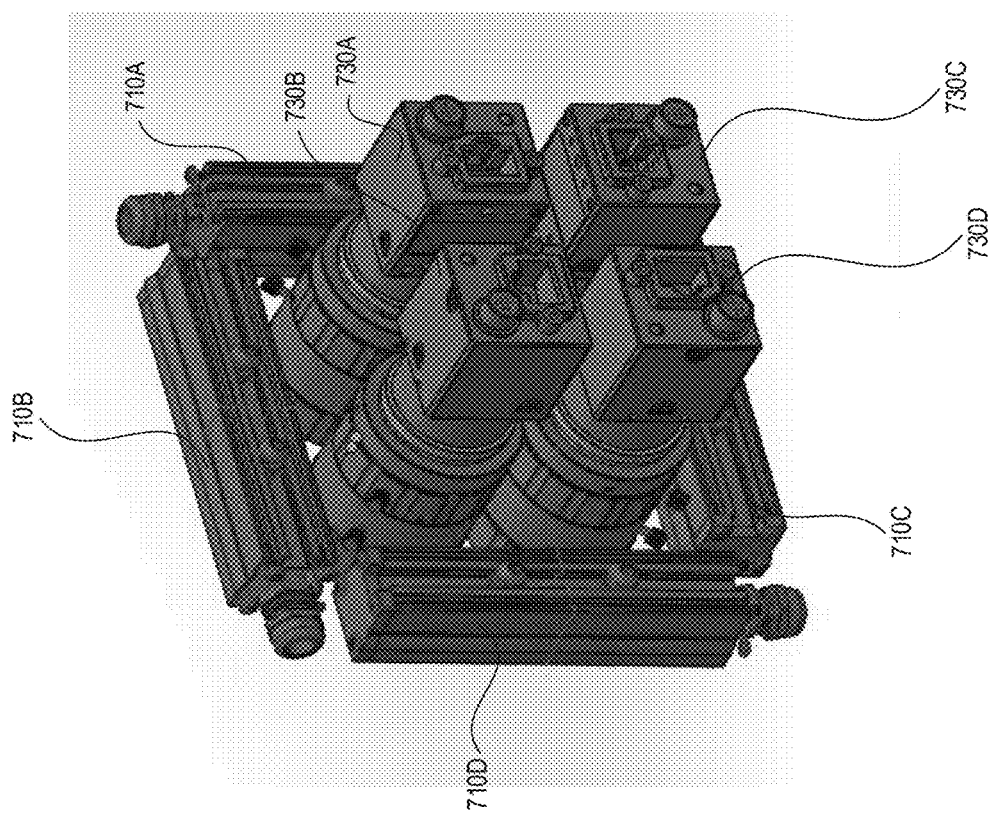
FIGS. 8A-8B depict another embodiment of a multispectral multi-aperture imaging system, with an optical design as described with respect to FIGS. 3A and 3B.
Figure 8A:
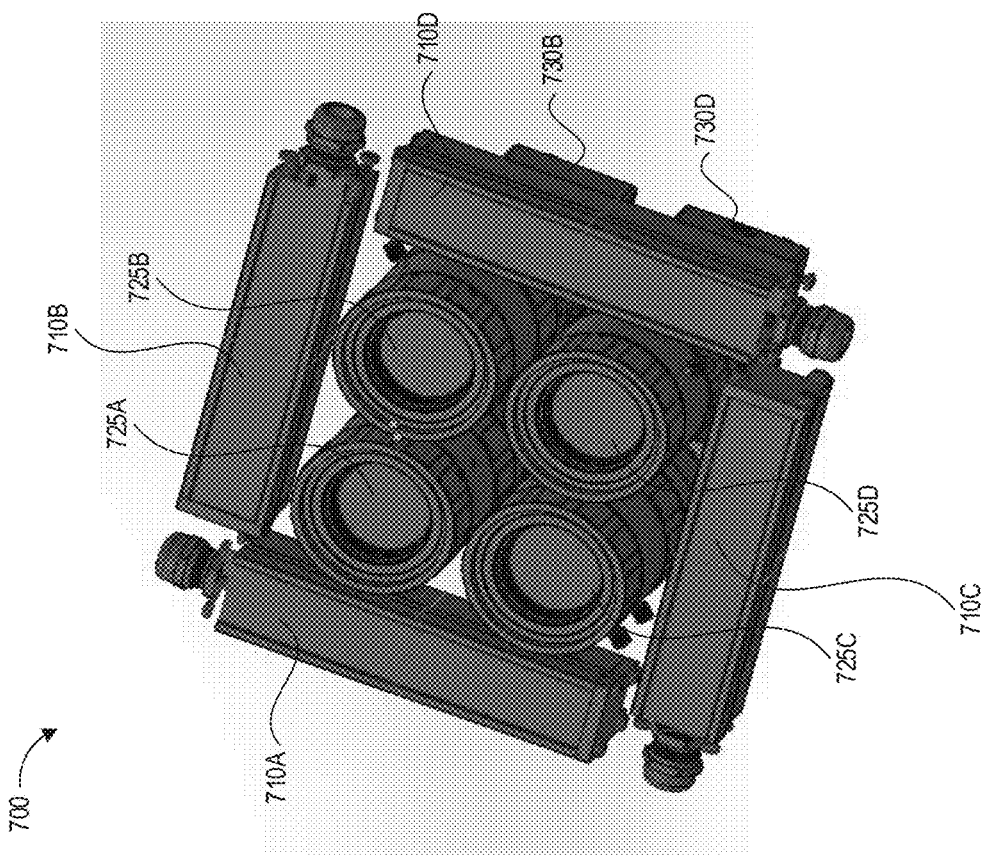

FIGS. 8A-8B depict another embodiment of a multispectral multi-aperture imaging system 700. FIGS. 8A-8B illustrate another possible arrangement of light sources 710A-710D around a multi-aperture imaging system 700. As depicted, four lens assemblies with multi-bandpass filters 725A-725D, employing an optical design as described with respect to FIGS. 3A-3D, can be disposed in a rectangular or square configuration to provide light to four cameras 730A-730D (including image sensors). The four cameras 730A-730D are illustrated in a closer example configuration which may minimize perspective differences between the lenses. Four rectangular light emitting elements 710A-710D can be positioned in a square surrounding the lens assemblies with multi-bandpass filters 725A-725D. These can be broad-spectrum light emitting panels or arrangements of LEDs that emit discrete wavebands of light.

Figure 9A:
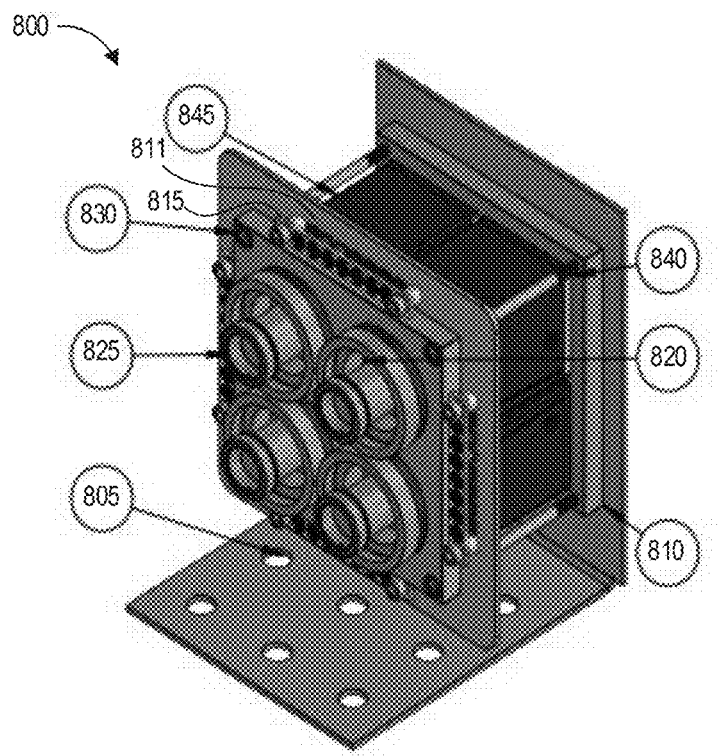
FIGS. 9A-9C depict another embodiment of a multispectral multi-aperture imaging system, with an optical design as described with respect to FIGS. 3A and 3B.
Figure 9B:
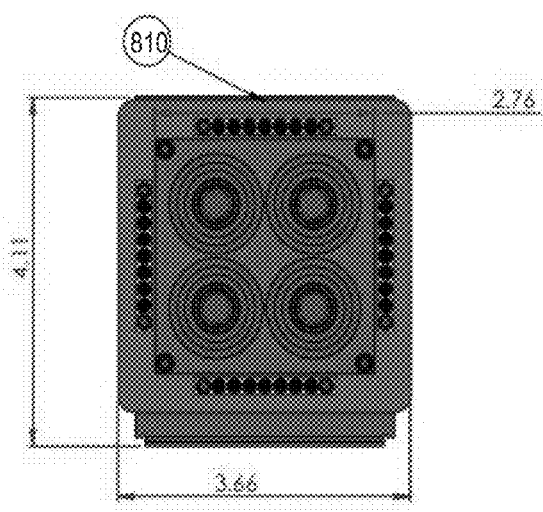
Figure 9C:
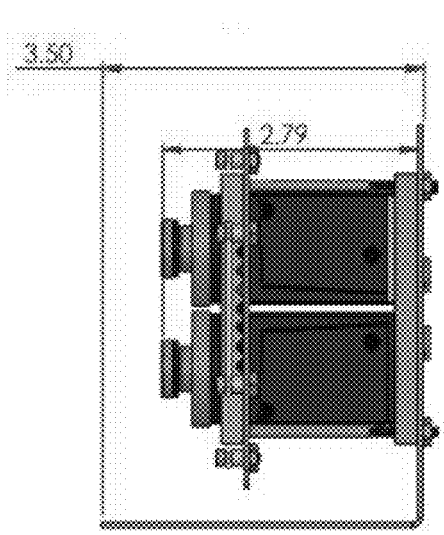

FIGS. 9A-9C depict another embodiment of a multispectral multi-aperture imaging system 800. The imaging system 800 includes a frame 805 coupled to a lens cluster frame front 830 that includes openings 820 and support structures for micro-video lenses 825, which can be provided with multi-bandpass filters using an optical design as described with respect to FIGS. 3A-3D. The micro-video lenses 825 provide light to four cameras 845 (including imaging lenses and image sensor regions) mounted on a lens cluster frame back 840. Four linear arrangements of LEDs 811 are disposed along the four sides of the lens cluster frame front 830, each provided with its own diffusing element 815. FIGS. 9B and 9C depict example dimensions in inches to show one possible size of the multi-aperture imaging system 800.

Figure 10B:
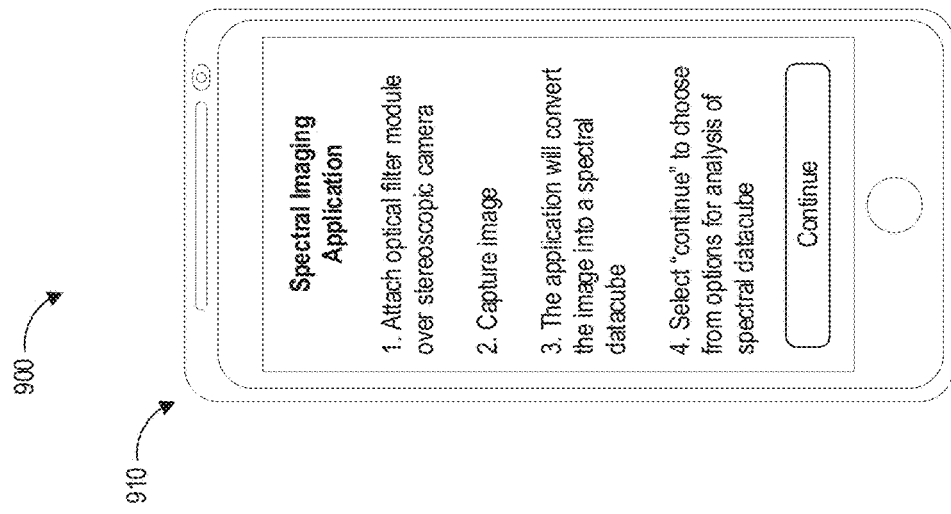
FIGS. 10A-10B depict another embodiment of a multispectral multi-aperture imaging system, with an optical design as described with respect to FIGS. 3A and 3B.
Figure 10A:
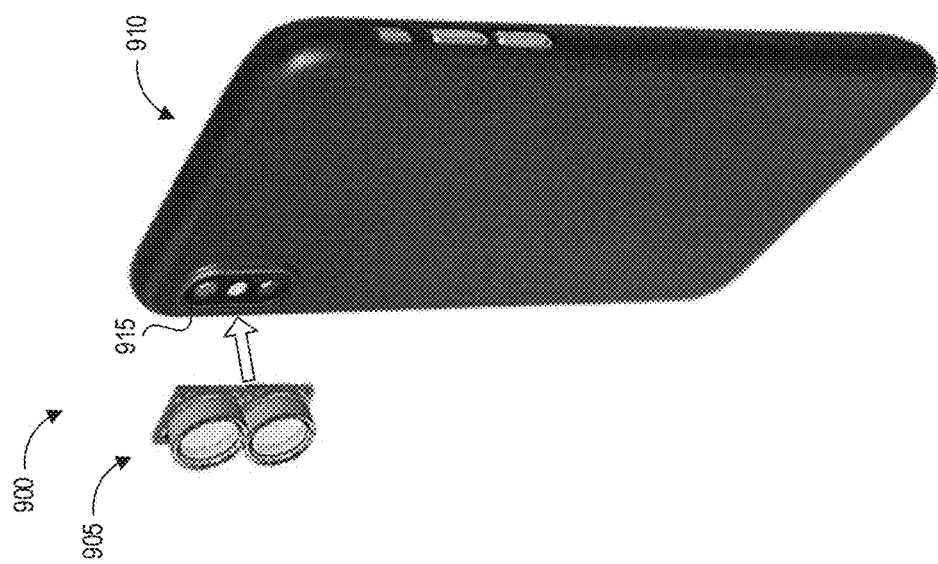

FIG. 10A depicts another embodiment of a multispectral multi-aperture imaging system 900, with an optical design as described with respect to FIGS. 3A-3D. The imaging system 900 can be implemented as a set of multi-bandpass filters 905 that are attachable over a multi-aperture camera 915 of a mobile device 910. For example, certain mobile devices 910 such as smartphones can be equipped with stereoscopic imaging systems having two openings leading to two image sensor regions. The disclosed multi-aperture spectral imaging techniques can be implemented in such devices by providing them with a suitable set of multi-bandpass filters 905 to pass multiple narrower wavebands of light to the sensor regions. Optionally, the set of multi-bandpass filters 905 can be equipped with an illuminant (such as an LED array and diffuser) that provides light at these wavebands to the object space.

The system 900 can also include a mobile application that configures the mobile device to perform the processing that generates the multispectral datacube, as well as processing the multispectral datacube (e.g., for clinical tissue classification, biometric recognition, materials analysis, or other applications). Alternatively, the mobile application may configure the device 910 to send the multispectral datacube over a network to a remote processing system, and then receive and display a result of the analysis. An example user interface 910 for such an application is shown in FIG. 10B.

Figure 11B:
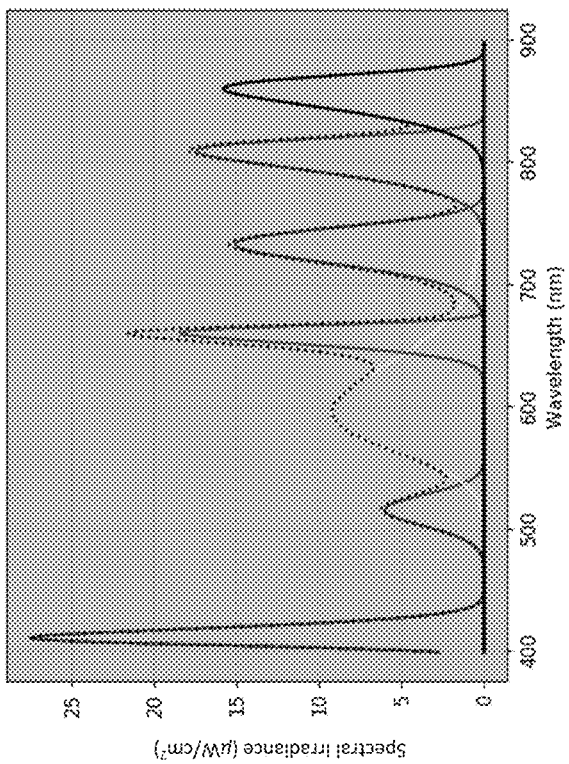
FIGS. 11A-11B depict an example set of wavebands that can be passed by the filters of the multispectral multi-aperture imaging systems of FIGS. 3A-10B.
Figure 11A:
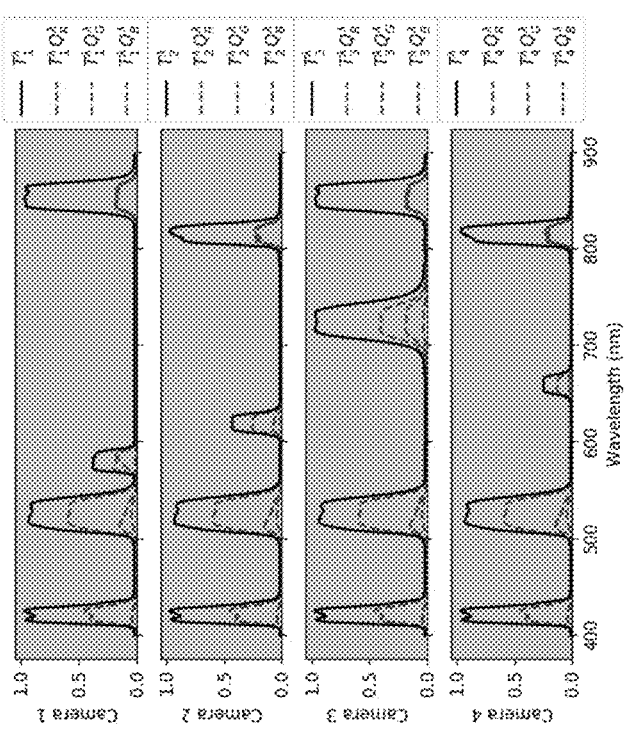

FIGS. 11A-11B depict an example set of wavebands that can be passed by the filters of four-filter implementations of the multispectral multi-aperture imaging systems of FIGS. 3A-10B, for example to an image sensor having the Bayer CFA (or another RGB or RGB-IR CFA). The spectral transmission response of wavebands as passed by the multi-bandpass filters are shown by the solid lines in the graphs 1000 of FIG. 11A and are denoted by $T_n^\lambda$, where n represents the camera number, ranging from 1 through 4. The dashed lines represent the combined spectral response of $T_n^\lambda$ with either the spectral transmission of a green pixel, $Q_G^\lambda$, a red pixel, $Q_R^\lambda$, or a blue pixel, $Q_B^\lambda$, that would be present in a typical Bayer CFA. These transmission curves also include the effects of quantum efficiency due to the sensor used in this example. As illustrated, this set of four cameras collectively captures eight unique channels or wavebands. Each filter passes two common wavebands (the two left-most peaks) to the respective cameras, as well as two additional wavebands. In this implementation, the first and third cameras receive light in a first shared NIR waveband (the right-most peak), and the second and fourth cameras receive light in a second shared NIR waveband (the peak second-most to the right). Each of the cameras also receives one unique waveband ranging from approximately 550 nm or 550 nm to approximately 800 nm or 800 nm. Thus, the camera can capture eight unique spectral channels using a compact configuration. A graph 1010 in FIG. 11B depicts the spectral irradiance of an LED board as described in FIG. 4E that may be used as illumination for the 4 cameras shown in FIG. 11A.

In this implementation, the eight wavebands have been selected based on producing spectral channels suitable for clinical tissue classification, and may also be optimized with respect to signal-to-noise ratio (SNR) and frame rate while limiting the number of LEDs (which introduce heat into the imaging system). The eight wavebands include a common waveband of blue light (the leftmost peak in the graphs 1000) that is passed by all four filters, because tissue (e.g., animal tissue including human tissue) exhibits higher contrast at blue wavelengths than at green or red wavelengths. Specifically, human tissue exhibits its highest contrast when imaged at a waveband centered on around 420 nm, as shown in the graphs 1000. Because the channel corresponding to the common waveband is used for disparity correction, this higher contrast can produce more accurate correction. For example in disparity correction the image processor can employ local or global methods to find a set of disparities so that a figure of merit corresponding to similarity between local image patches or images is maximized. Alternatively, the image processor can employ similar methods that minimize a figure of merit corresponding to dissimilarity. These figures of merit can be based on entropy, correlation, absolute differences, or on deep learning methods. Global methods of disparity calculation can operate iteratively, terminating when the figure of merit is stable. Local methods can be used to calculate disparity point by point, using a fixed patch in one image as an input into the figure of merit and a number of different patches, each determined by a different value of disparity under test, from the other image. All such methods can have constraints imposed on the range of disparities that are considered. These constraints can be based on knowledge of the object depth and distance, for instance. The constraints could also be imposed based on a range of gradients expected in an object. Constraints on the calculated disparities can also be imposed by projective geometry, such as the epipolar constraint. Disparity can be calculated at multiple resolutions, with the output of disparities calculated at lower resolutions acting as initial values or constraints on the disparities calculated at the next level of resolution. For instance, a disparity calculated at a resolution level of 4 pixels in one calculation can be used to set constraints of ±4 pixels in a next calculation of disparity at higher resolution. All algorithms that calculate from disparity will benefit from higher contrast, particularly if that source of contrast is correlated for all viewpoints. Generally speaking, the common waveband can be selected based on corresponding to the highest contrast imaging of the material that is expected to be imaged for a particular application.

After image capture, color separation between adjacent channels may not be perfect, and so this implementation also has an additional common waveband passed by all filters—depicted in the graphs 1000 as the green waveband adjacent to the blue waveband. This is because blue color filter pixels are sensitive to retions of the green spectrum due to its broad spectral bandpass. This typically manifests as spectral overlap, which may also be characterized as intentional crosstalk, between adjacent RGB pixels. This overlap enables the spectral sensitivity of color cameras to be similar to the spectral sensitivity of a human retina, such that the resultant color space is qualitatively similar to human vision. Accordingly, having a common green channel can enable separation of the portion of the signal generated by blue photodiodes that truly corresponds to received blue light, by separating out the portion of the signal due to green light. This can be accomplished using spectral unmixing algorithms that factor in the transmittance (shown in the legend by T with a solid black line) of the multi-band pass filter, the transmittance of the corresponding CFA color filter (shown in the legend by Q with dashed red, green, and blue lines). It will be appreciated that some implementations may use red light as a common waveband, and in such instances a second common channel may not be necessary.

Figure 12:
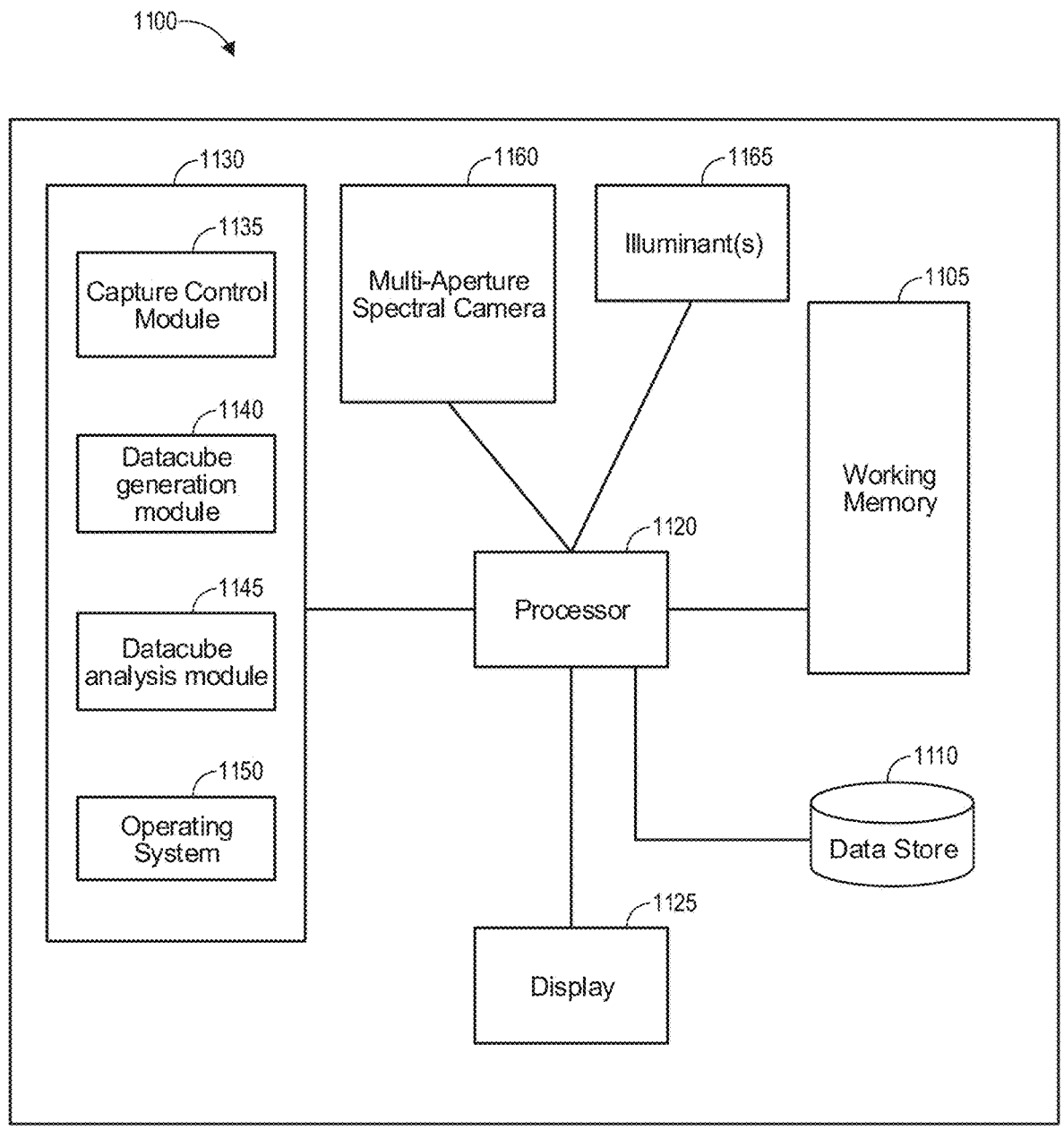
FIG. 12 depicts a schematic block diagram of an imaging system that can be used for the multispectral multi-aperture imaging systems of FIGS. 3A-10B.

FIG. 12 illustrates a high-level block diagram of an example compact imaging system 1100 with high resolution spectral imaging capabilities, the system 1100 having a set of components including a processor 1120 linked to an multi-aperture spectral camera 1160 and illuminant(s) 1165. A working memory 1105, storage 1110, electronic display 1125, and memory 1130 are also in communication with the processor 1120. As described herein, the system 1100 may capture a greater number of image channels than there are different colors of filters in the CFA of the image sensor by using different multi-bandpass filters placed over different openings of the multi-aperture spectral camera 1160.

System 1100 may be a device such as cell phone, digital camera, tablet computer, personal digital assistant, or the like. System 1100 may also be a more stationary device such as a desktop personal computer, video conferencing station, or the like that uses an internal or external camera for capturing images. System 1100 can also be a combination of an image capture device and a separate processing device receiving image data from the image capture device. A plurality of applications may be available to the user on system 1100. These applications may include traditional photographic applications, capture of still images and video, dynamic color correction applications, and brightness shading correction applications, among others.

The image capture system 1100 includes the multi-aperture spectral camera 1160 for capturing images. The multi-aperture spectral camera 1160 can be, for example, any of the devices of FIGS. 3A-10B. The multi-aperture spectral camera 1160 may be coupled to the processor 1120 to transmit captured images in different spectral channels and from different sensor regions to the image processor 1120. The illuminant(s) 1165 can also be controlled by the processor to emit light at certain wavelengths during certain exposures, as described in more detail below. The image processor 1120 may be configured to perform various operations on a received captured image in order to output a high quality, disparity corrected multispectral datacube.

Processor 1120 may be a general purpose processing unit or a processor specially designed for imaging applications. As shown, the processor 1120 is connected to a memory 1130 and a working memory 1105. In the illustrated embodiment, the memory 1130 stores a capture control module 1135, datacube generation module 1140, datacube analysis module 1145, and operating system 1150. These modules include instructions that configure the processor to perform various image processing and device management tasks. Working memory 1105 may be used by processor 1120 to store a working set of processor instructions contained in the modules of memory 1130. Alternatively, working memory 1105 may also be used by processor 1120 to store dynamic data created during the operation of device 1100.

As mentioned above, the processor 1120 is configured by several modules stored in the memory 1130. The capture control module 1135 includes instructions that configure the processor 1120 to adjust the focus position of the multi-aperture spectral camera 1160, in some implementations. The capture control module 1135 also includes instructions that configure the processor 1120 to capture images with the multi-aperture spectral camera 1160, for example multispectral images captured at different spectral channels as well as PPG images captured at the same spectral channel (e.g., a NIR channel). Non-contact PPG imaging normally uses near-infrared (NIR) wavelengths as illumination to take advantage of the increased photon penetration into the tissue at this wavelength. Therefore, processor 1120, along with capture control module 1135, multi-aperture spectral camera 1160, and working memory 1105 represent one means for capturing a set of spectral images and/or a sequence of images.

The datacube generation module 1140 includes instructions that configure the processor 1120 to generate a multispectral datacube based on intensity signals received from the photodiodes of different sensor regions. For example, the datacube generation module 1140 can estimate a disparity between the same regions of an imaged object based on a spectral channel corresponding to the common waveband passed by all multi-bandpass filters, and can use this disparity to register all spectral images across all captured channels to one another (e.g., such that the same point on the object is represented by substantially the same (x,y) pixel location across all spectral channels). The registered images collectively form the multispectral datacube, and the disparity information may be used to determine depths of different imaged objects, for example a depth difference between healthy tissue and a deepest location within a wound site. In some embodiments, the datacube generation module 1140 may also perform spectral unmixing to identify which portions of the photodiode intensity signals correspond to which passed wavebands, for example based on spectral unmixing algorithms that factor in filter transmittances and sensor quantum efficiency.

The datacube analysis module 1145 can implement various techniques to analyze the multispectral datacube generated by the datacube generation module 1140, depending upon the application. For example, some implementations of the datacube analysis module 1145 can provide the multispectral datacube (and optionally depth information) to a machine learning model trained to classify each pixel according to a certain state. These states may be clinical states in the case of tissue imaging, for example burn states (e.g., first degree burn, second degree burn, third degree burn, or healthy tissue categories), wound states (e.g., hemostasis, inflammation, proliferation, remodeling or healthy skin categories), healing potential (e.g., a score reflecting the likelihood that the tissue will heal from a wounded state, with or without a particular therapy), perfusion states, cancerous states, or other wound-related tissue states. The datacube analysis module 1145 can also analyze the multispectral datacube for biometric recognition and/or materials analysis.

Operating system module 1150 configures the processor 1120 to manage the memory and processing resources of the system 1100. For example, operating system module 1150 may include device drivers to manage hardware resources such as the electronic display 1125, storage 1110, multi-aperture spectral camera 1160, or illuminant(s) 1165. Therefore, in some embodiments, instructions contained in the image processing modules discussed above may not interact with these hardware resources directly, but instead interact through standard subroutines or APIs located in operating system component 1150. Instructions within operating system 1150 may then interact directly with these hardware components.

The processor 1120 may be further configured to control the display 1125 to display the captured images and/or a result of analyzing the multispectral datacube (e.g., a classified image) to a user. The display 1125 may be external to an imaging device including the multi-aperture spectral camera 1160 or may be part of the imaging device. The display 1125 may also be configured to provide a view finder for a user prior to capturing an image. The display 1125 may comprise an LCD or LED screen, and may implement touch sensitive technologies.

Processor 1120 may write data to storage module 1110, for example data representing captured images, multispectral datacubes, and datacube analysis results. While storage module 1110 is represented graphically as a traditional disk device, those with skill in the art would understand that the storage module 1110 may be configured as any storage media device. For example, the storage module 1110 may include a disk drive, such as a floppy disk drive, hard disk drive, optical disk drive or magneto-optical disk drive, or a solid state memory such as a FLASH memory, RAM, ROM, and/or EEPROM. The storage module 1110 can also include multiple memory units, and any one of the memory units may be configured to be within the image capture device 1100, or may be external to the image capture system 1100. For example, the storage module 1110 may include a ROM memory containing system program instructions stored within the image capture system 1100. The storage module 1110 may also include memory cards or high speed memories configured to store captured images which may be removable from the camera.

Although FIG. 12 depicts a system comprising separate components to include a processor, imaging sensor, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 12 illustrates two memory components—memory component 1130 comprising several modules and a separate memory 1105 comprising a working memory—one with skill in the art would recognize several embodiments utilizing different memory architectures. For example, a design may utilize ROM or static RAM memory for the storage of processor instructions implementing the modules contained in memory 1130. Alternatively, processor instructions may be read at system startup from a disk storage device that is integrated into system 1100 or connected via an external device port. The processor instructions may then be loaded into RAM to facilitate execution by the processor. For example, working memory 1105 may be a RAM memory, with instructions loaded into working memory 1105 before execution by the processor 1120.

Overview of Example Image Processing Techniques

Figure 13:
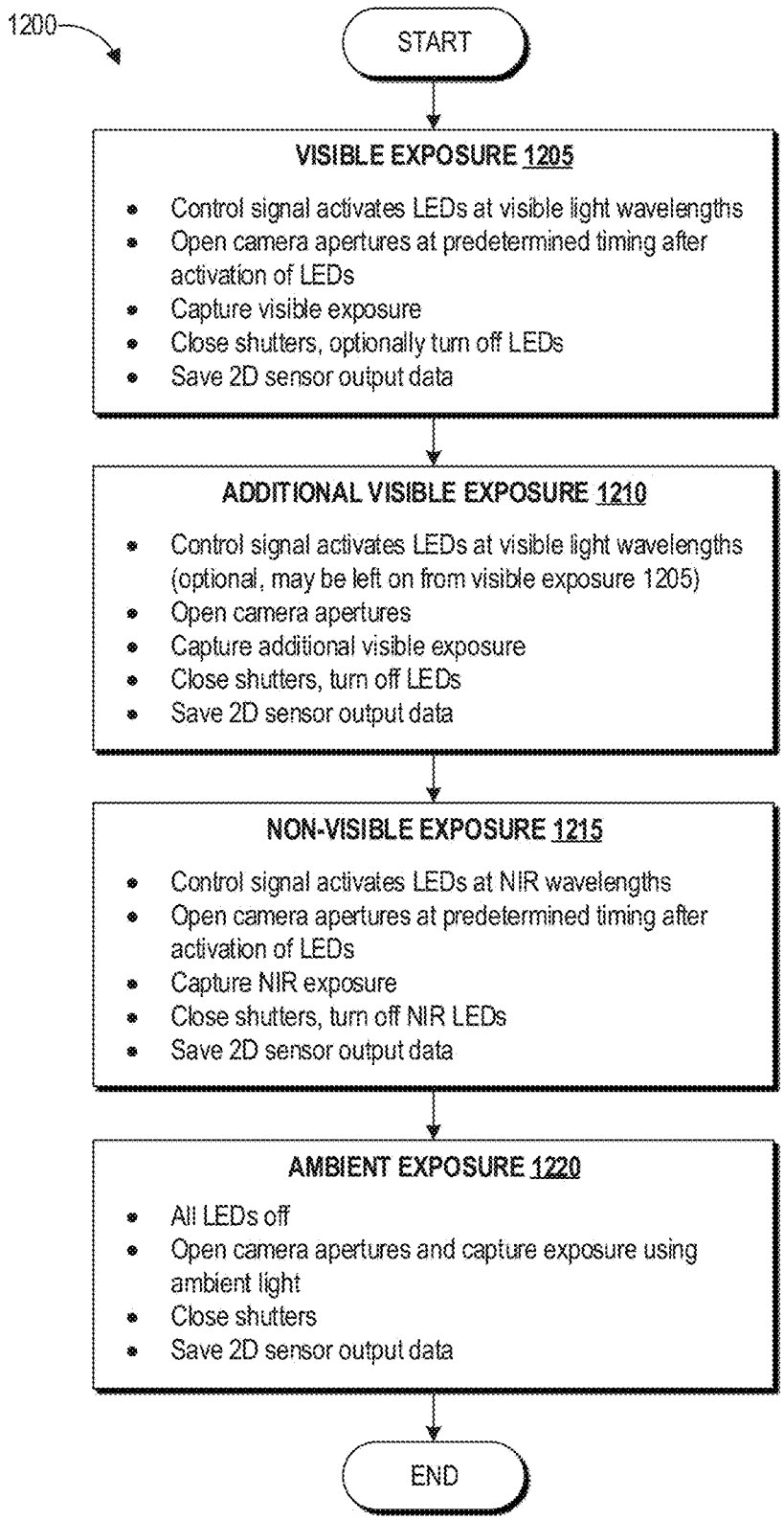
FIG. 13 is a flowchart of an example process for capturing image data using the multispectral multi-aperture imaging systems of FIGS. 3A-10B.

FIG. 13 is a flowchart of an example process 1200 for capturing image data using the multispectral multi-aperture imaging systems of FIGS. 3A-10B and 12. FIG. 13 depicts four example exposures that can be used to generate a multispectral datacube as described herein—a visible exposure 1205, an additional visible exposure 1210, a non-visible exposure 1215, and an ambient exposure 1220. It will be appreciated that these may be captured in any order, and some exposures may be optionally removed from or added to a particular workflow as described below. Further, the process 1200 is described with reference to the wavebands of FIGS. 11A and 11B, however similar workflows can be implemented using image data generated based on other sets of wavebands. Additionally, flat field correction may further be implemented in accordance with various known flat field correction techniques, to improve image acquisition and/or disparity correction in various embodiments.

For the visible exposure 1205, LEDs of first five peaks (the left five peaks corresponding to visible light in the graphs 1000 of FIG. 11A) can be turned on by a control signal to the illumination board. The wave of light output may need to stabilize, at a time specific to particular LEDs, for example 10 ms. The capture control module 1135 can begin the exposure of the four cameras after this time and can continue this exposure for a duration of around 30 ms, for example. Thereafter, the capture control module 1135 can cease the exposure and pull the data off of the sensor regions (e.g., by transferring raw photodiode intensity signals to the working memory 1105 and/or data store 1110). This data can include a common spectral channel for use in disparity correction as described herein.

In order to increase the SNR, some implementations can capture the additional visible exposure 1210 using the same process described for the visible exposure 1205. Having two identical or near-identical exposures can increase the SNR to yield more accurate analysis of the image data. However, this may be omitted in implementations where the SNR of a single image is acceptable. A duplicate exposure with the common spectral channel may also enable more accurate disparity correction in some implementations.

Some implementations can also capture a non-visible exposure 1215 corresponding to NIR or IR light. For example, the capture control module 1135 can activate two different NIR LEDs corresponding to the two NIR channels shown in FIG. 11A. The wave of light output may need to stabilize, at a time specific to particular LEDs, for example 10 ms. The capture control module 1135 can begin the exposure of the four cameras after this time and continue this exposure for a duration of around 30 ms, for example. Thereafter, the capture control module 1135 can cease the exposure and pull the data off of the sensor regions (e.g., by transferring raw photodiode intensity signals to the working memory 1105 and/or data store 1110). In this exposure, there may be no common waveband passed to all sensor regions, as it can safely be assumed that there is no change in the shape or positioning of the object relative to the exposures 1205, 1210 and, thus previously computed disparity values can be used to register the NIR channels.

In some implementations, multiple exposures can be captured sequentially to generate PPG data representing the change in shape of a tissue site due to pulsatile blood flow. These PPG exposures may be captured at a non-visible wavelength in some implementations. Although the combination of PPG data with multispectral data may increase the accuracy of certain medical imaging analyses, the capture of PPG data can also introduce additional time into the image capture process. This additional time can introduce errors due to movement of the handheld imager and/or object, in some implementations. Thus, certain implementations may omit capture of PPG data.

Some implementations can additionally capture the ambient exposure 1220. For this exposure, all LEDs can be turned off to capture an image using ambient illumination (e.g., sunlight, light from other illuminant sources). The capture control module 1135 can begin the exposure of the four cameras after this time and can keep the exposure ongoing for a desired duration of, for example, around 30 ms. Thereafter, the capture control module 1135 can cease the exposure and pull the data off of the sensor regions (e.g., by transferring raw photodiode intensity signals to the working memory 1105 and/or data store 1110). The intensity values of the ambient exposure 1220 can be subtracted from the values of the visible exposure 1205 (or the visible exposure 1205 corrected for SNR by the second exposure 1210) and also from the non-visible exposure 1215 in order to remove the influence of ambient light from the multispectral datacube. This can increase the accuracy of downstream analysis by isolating the portion of the generated signals that represent light emitted by the illuminants and reflected from the object/tissue site. Some implementations may omit this step if analytical accuracy is sufficient using just the visible 1205, 1210 and non-visible 1215 exposures.

It will be appreciated that the particular exposure times listed above are examples of one implementation, and that in other implementations exposure time can vary depending upon the image sensor, illuminant intensity, and imaged object.

Figure 14:
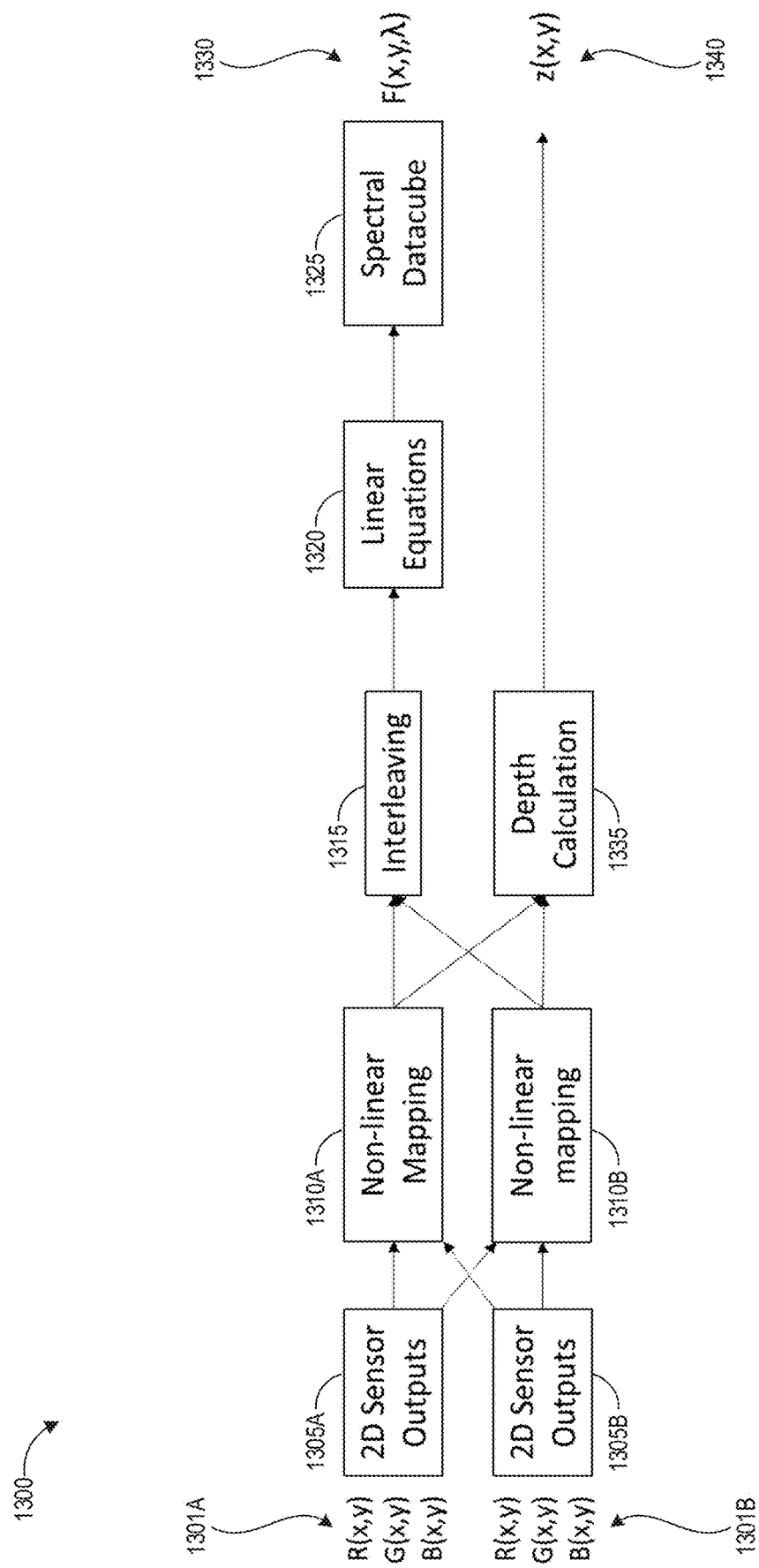
FIG. 14 depicts a schematic block diagram of a workflow for processing image data, for example image data captured using the process of FIG. 13 and/or using the multispectral multi-aperture imaging systems of FIGS. 3A-10B.

FIG. 14 depicts a schematic block diagram of a workflow 1300 for processing image data, for example image data captured using the process 1200 of FIG. 13 and/or using the multispectral multi-aperture imaging systems of FIGS. 3A-10B and 12. The workflow 1300 shows the output of two RGB sensor regions 1301A, 1301B, however the workflow 1300 can be extended to greater numbers of sensor regions and sensor regions corresponding to different CFA color channels.

The RGB sensor outputs from the two sensor regions 1301A, 1301B are stored at the 2D sensor outputs modules 1305A, 1305B, respectively. The values of both sensor regions are sent to the non-linear mapping modules 1310A, 1310B, which can perform disparity correction by identifying disparity between the captured images using the common channel and then applying this determined disparity across all channels to register all spectral images to one another.

The outputs of both non-linear mapping modules 1310A, 1310B are then provided to the depth calculation module 1335, which can compute a depth of a particular region of interest in the image data. For example, the depth may represent the distance between the object and the image sensor. In some implementations, multiple depth values can be computed and compared to determine the depth of the object relative to something other than the image sensor. For example, a greatest depth of a wound bed can be determined, as well as a depth (greatest, lowest, or average) of healthy tissue surrounding the wound bed. By subtracting the depth of the healthy tissue from the depth of the wound bed, the deepest depth of the wound can be determined. This depth comparison can additionally be performed at other points in the wound bed (e.g., all or some predetermined sampling) in order to build a 3D map of the depth of the wound at various points (shown in FIG. 14 as z(x,y) where z would be a depth value). In some embodiments, greater disparity may improve the depth calculation, although greater disparity may also result in more computationally intensive algorithms for such depth calculations.

The outputs of both non-linear mapping modules 1310A, 1310B are also provided to the linear equations module 1320, which can treat the sensed values as set of linear equations for spectral unmixing. One implementation can use the Moore-Penrose pseudo-inverse equation as a function of at least sensor quantum efficiency and filter transmittance values to compute actual spectral values (e.g., intensity of light at particular wavelengths that were incident at each (x,y) image point). This can be used in implementations that require high accuracy, such as clinical diagnostics and other biological applications. Application of the spectral unmixing can also provide an estimate of photon flux and SNR.

Based on the disparity-corrected spectral channel images and the spectral unmixing, the workflow 1300 can generate a spectral datacube 1325, for example in the illustrated format of $F(x,y,\lambda)$ where F represents the intensity of light at a specific (x,y) image location at a specific wavelength or waveband $\lambda$.

Figure 15:
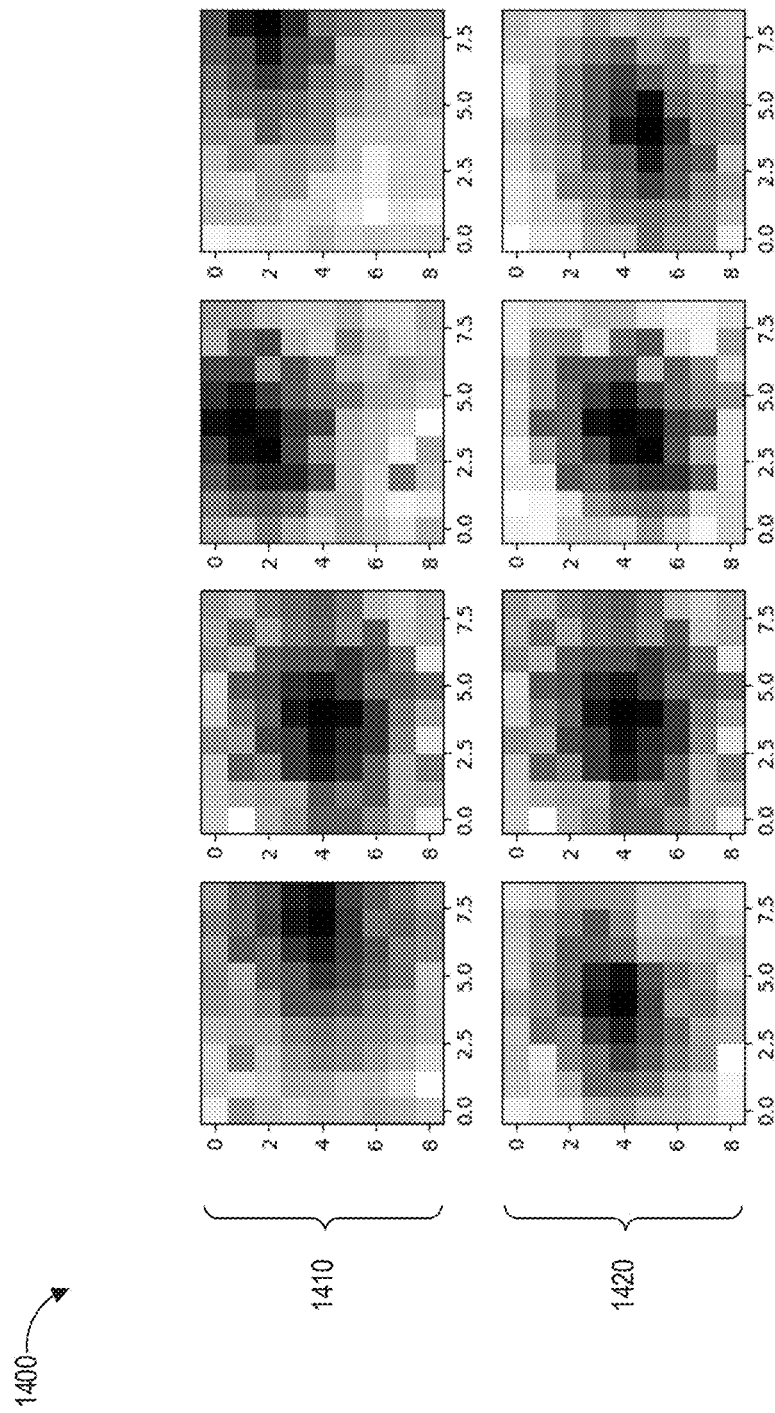
FIG. 15 graphically depicts disparity and disparity correction for processing image data, for example image data captured using the process of FIG. 13 and/or using the multispectral multi-aperture imaging systems of FIGS. 3A-10B.

FIG. 15 graphically depicts disparity and disparity correction for processing image data, for example image data captured using the process of FIG. 13 and/or using the multispectral multi-aperture imaging systems of FIGS. 3A-10B and 12. The first set of images 1410 show image data of the same physical location on an object as captured by four different sensor regions. As illustrated, this object location is not in the same location across the raw images, based on the (x,y) coordinate frames of the photodiode grids of the image sensor regions. The second set of images 1420 shows that same object location after disparity correction, which is now in the same (x,y) location in the coordinate frame of the registered images. It will be appreciated that such registration may involve cropping certain data from edge regions of the images that do not entirely overlap with one another.

Figure 16:
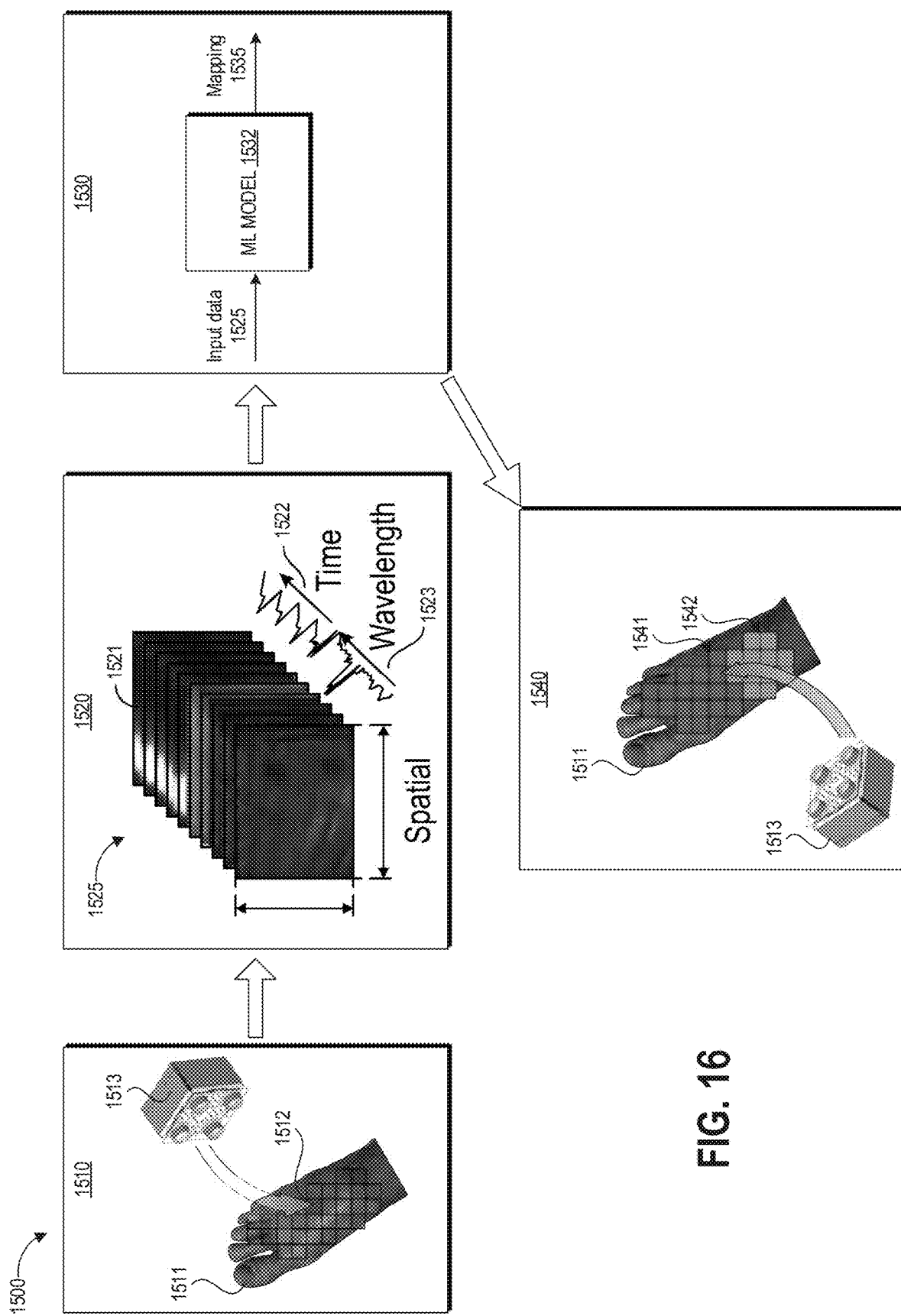
FIG. 16 graphically depicts a workflow for performing pixel-wise classification on multispectral image data, for example image data captured using the process of FIG. 13, processed according to FIGS. 14 and 15, and/or using the multispectral multi-aperture imaging systems of FIGS. 3A-10B.

FIG. 16 graphically depicts a workflow 1500 for performing pixel-wise classification on multispectral image data, for example image data captured using the process of FIG. 13, processed according to FIGS. 14 and 15, and/or using the multispectral multi-aperture imaging systems of FIGS. 3A-10B and 12.

At block 1510, the multispectral multi-aperture imaging system 1513 can capture image data representing physical points 1512 on an object 1511. In this example, the object 1511 includes tissue of a patient that has a wound. A wound can comprise a burn, a diabetic ulcer (e.g., a diabetic foot ulcer), a non-diabetic ulcer (e.g., pressure ulcers or slow-healing wounds), a chronic ulcer, a post-surgical incision, an amputation site (before or after the amputation procedure), a cancerous lesion, or damaged tissue. Where PPG information is included, the disclosed imaging systems provide a method to assess pathologies involving changes to tissue blood flow and pulse rate including: tissue perfusion; cardiovascular health; wounds such as ulcers; peripheral arterial disease, and respiratory health.

At block 1520, the data captured by the multispectral multi-aperture imaging system 1513 can be processed into a multispectral datacube 1525 having a number of different wavelengths 1523, and, optionally, a number of different images at the same wavelength corresponding to different times (PPG data 1522). For example, the image processor 1120 can be configured by the datacube generation module 1140 to generate the multispectral datacube 1525 according to the workflow 1300. Some implementations may also associated depth values with various points along the spatial dimensions, as described above.

At block 1530, the multispectral datacube 1525 can be analyzed as input data 1525 into a machine learning model 1532 to generate a classified mapping 1535 of the imaged tissue. The classified mapping can assign each pixel in the image data (which, after registration, represent specific points on the imaged object 1511) to a certain tissue classification, or to a certain healing potential score. The different classifications and scores can be represented using visually distinct colors or patterns in the output classified image. Thus, even though a number of images are captured of the object 1511, the output can be a single image of the object (e.g., a typical RGB image) overlaid with visual representations of pixel-wise classification.

The machine learning model 1532 can be an artificial neural network in some implementations. Artificial neural networks are artificial in the sense that they are computational entities, inspired by biological neural networks but modified for implementation by computing devices. Artificial neural networks are used to model complex relationships between inputs and outputs or to find patterns in data, where the dependency between the inputs and the outputs cannot be easily ascertained. A neural network typically includes an input layer, one or more intermediate ("hidden") layers, and an output layer, with each layer including a number of nodes. The number of nodes can vary between layers. A neural network is considered "deep" when it includes two or more hidden layers. The nodes in each layer connect to some or all nodes in the subsequent layer and the weights of these connections are typically learnt from data during the training process, for example through backpropagation in which the network parameters are tuned to produce expected outputs given corresponding inputs in labeled training data. Thus, an artificial neural network is an adaptive system that is configured to change its structure (e.g., the connection configuration and/or weights) based on information that flows through the network during training, and the weights of the hidden layers can be considered as an encoding of meaningful patterns in the data.

A fully connected neural network is one in which each node in the input layer is connected to each node in the subsequent layer (the first hidden layer), each node in that first hidden layer is connected in turn to each node in the subsequent hidden layer, and so on until each node in the final hidden layer is connected to each node in the output layer.

A CNN is a type of artificial neural network, and like the artificial neural network described above, a CNN is made up of nodes and has learnable weights. However, the layers of a CNN can have nodes arranged in three dimensions: width, height, and depth, corresponding to the 2×2 array of pixel values in each video frame (e.g., the width and height) and to the number of video frames in the sequence (e.g., the depth). The nodes of a layer may only be locally connected to a small region of the width and height layer before it, called a receptive field. The hidden layer weights can take the form of a convolutional filter applied to the receptive field. In some embodiments, the convolutional filters can be two-dimensional, and thus, convolutions with the same filter can be repeated for each frame (or convolved transformation of an input volume or for designated subset of the frames. In other embodiments, the convolutional filters can be three-dimensional and thus extend through the full depth of nodes of the input volume. The nodes in each convolutional layer of a CNN can share weights such that the convolutional filter of a given layer is replicated across the entire width and height of the input volume (e.g., across an entire frame), reducing the overall number of trainable weights and increasing applicability of the CNN to data sets outside of the training data. Values of a layer may be pooled to reduce the number of computations in a subsequent layer (e.g., values representing certain pixels may be passed forward while others are discarded), and further along the depth of the CNN pool masks may reintroduce any discarded values to return the number of data points to the previous size. A number of layers, optionally with some being fully connected, can be stacked to form the CNN architecture.

During training, an artificial neural network can be exposed to pairs in its training data and can modify its parameters to be able to predict the output of a pair when provided with the input. For example, the training data can include multispectral datacubes (the input) and classified mappings (the expected output) that have been labeled, for example by a clinician who has designated areas of the wound that correspond to certain clinical states, and/or with healing (1) or non-healing (0) labels sometime after initial imaging of the wound when actual healing is known. Other implementations of the machine learning model 1532 can be trained to make other types of predictions, for example the likelihood of a wound healing to a particular percentage area reduction over a specified time period (e.g., at least 50% area reduction within 30 days) or wound states such as, hemostasis, inflammation, pathogen colonization, proliferation, remodeling or healthy skin categories. Some implementations may also incorporate patient metrics into the input data to further increase classification accuracy, or may segment training data based on patient metrics to train different instances of the machine learning model 1532 for use with other patients having those same patient metrics. Patient metrics can include textual information or medical history or aspects thereof describing characteristics of the patient or the patient's health status, for example the area of a wound, lesion, or ulcer, the BMI of the patient, the diabetic status of the patient, the existence of peripheral vascular disease or chronic inflammation in the patient, the number of other wounds the patient has or has had, whether the patient is or has recently taken immunosuppressant drugs (e.g., chemotherapy) or other drugs that positively or adversely affect wound healing rate, HbA1c, chronic kidney failure stage IV, type II vs type I diabetes, chronic anemia, asthma, drug use, smoking status, diabetic neuropathy, deep vein thrombosis, previous myocardial infarction, transient ischemic attacks, or sleep apnea or any combination thereof. These metrics can be converted into a vector representation through appropriate processing, for example through word-to-vec embeddings, a vector having binary values representing whether the patient does or does not have the patient metric (e.g., does or does not have type I diabetes), or numerical values representing a degree to which the patient has each patient metric.

At block 1540, the classified mapping 1535 can be output to a user. In this example, the classified mapping 1535 uses a first color 1541 to denote pixels classified according to a first state and uses a second color 1542 to denote pixels classified according to a second state. The classification and resulting classified mapping 1535 may exclude background pixels, for example based on object recognition, background color identification, and/or depth values. As illustrated, some implementations of the multispectral multi-aperture imaging system 1513 can project the classified mapping 1535 back on to the tissue site. This can be particularly beneficial when the classified mapping includes a visual representation of a recommended margin and/or depth of excision.

These methods and systems may provide assistance to clinicians and surgeons in the process of dermal wound management, such as burn excision, amputation level, lesion removal, and wound triage decisions. Alternatives described herein can be used to identify and/or classify the severity of decubitus ulcers, hyperaemia, limb deterioration, Raynaud's Phenomenon, scleroderma, chronic wounds, abrasions, lacerations, hemorrhaging, rupture injuries, punctures, penetrating wounds, skin cancers, such as basal cell carcinoma, squamous cell carcinoma, melanoma, actinic keratosis, or any type of tissue change, wherein the nature and quality of the tissue differs from a normal state. The devices described herein may also be used to monitor healthy tissue, facilitate and improve wound treatment procedures, for example allowing for a faster and more refined approach for determining the margin for debridement, and evaluate the progress of recovery from a wound or disease, especially after a treatment has been applied. In some alternatives described herein, devices are provided that allow for the identification of healthy tissue adjacent to wounded tissue, the determination of an excision margin and/or depth, the monitoring of the recovery process after implantation of a prosthetic, such as a left ventricular assist device, the evaluation of the viability of a tissue graft or regenerative cell implant, or the monitoring of surgical recovery, especially after reconstructive procedures. Moreover, alternatives described herein may be used to evaluate the change in a wound or the generation of healthy tissue after a wound, in particular, after introduction of a therapeutic agent, such as a steroid, hepatocyte growth factor, fibroblast growth factor, an antibiotic, or regenerative cells, such as an isolated or concentrated cell population that comprises stem cells, endothelial cells and/or endothelial precursor cells.

Overview of Example Distributed Computing Environment

Figure 17:
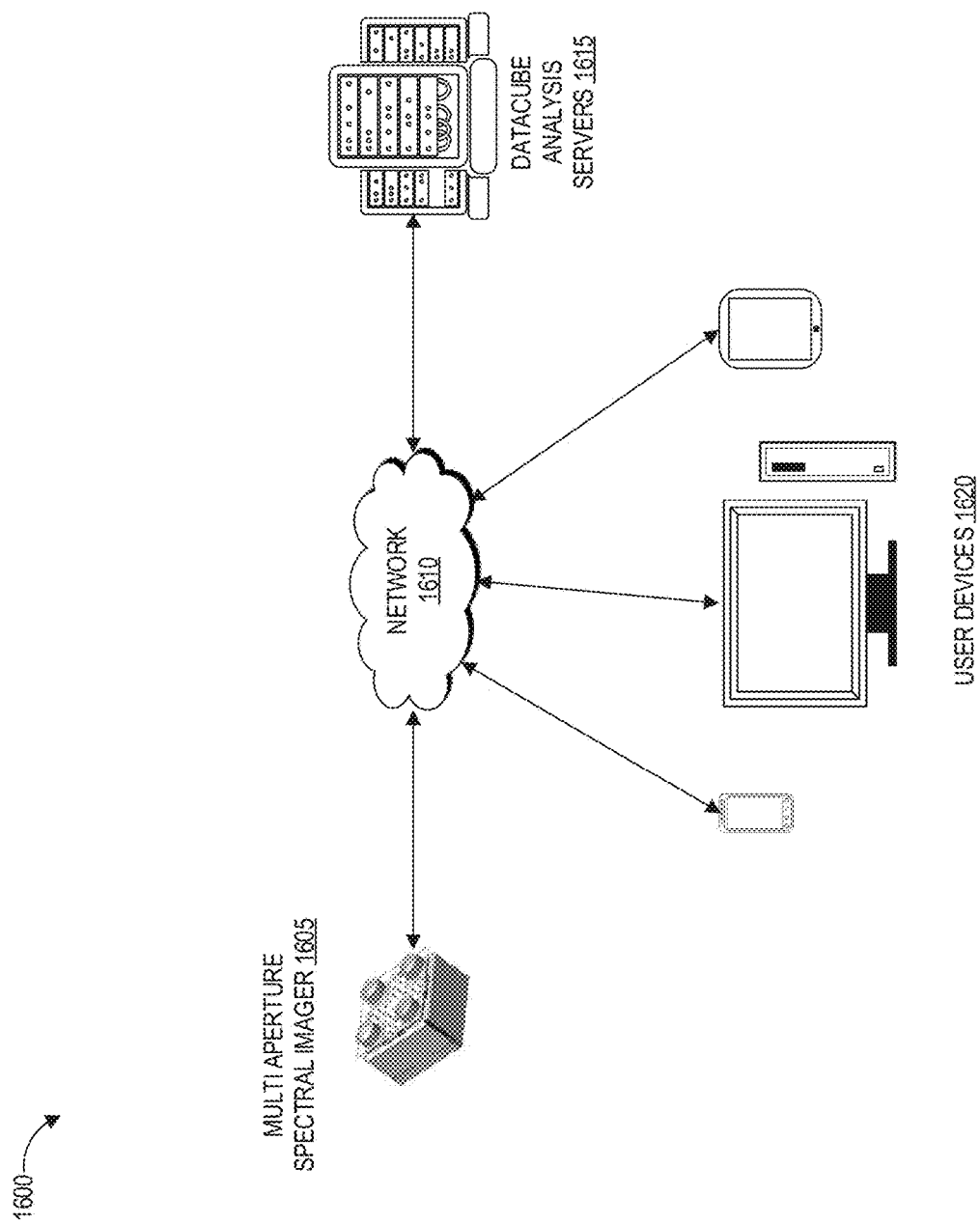
FIG. 17 depicts a schematic block diagram of an example distributed computing system including the multispectral multi-aperture imaging systems of FIGS. 3A-10B.

FIG. 17 depicts a schematic block diagram of an example distributed computing system 1600 including a multispectral multi-aperture imaging system 1605, which can be any of the multispectral multi-aperture imaging systems of FIGS. 3A-10B and 12. As depicted the datacube analysis servers 1615 may include one or more computers, perhaps arranged in a cluster of servers or as a server farm. The memory and processors that make up these computers may be located within one computer or distributed throughout many computers (including computers that are remote from one another).

The multispectral multi-aperture imaging system 1605 can include networking hardware (e.g., a wireless Internet, satellite, Bluetooth, or other transceiver) for communicating over the network 1610 with user devices 1620 and datacube analysis servers 1615. For example, in some implementations the processor of the multispectral multi-aperture imaging system 1605 may be configured to control image capture, and then send raw data to the datacube analysis servers 1615. Other implementations of the processor of the multispectral multi-aperture imaging system 1605 may be configured to control image capture and perform spectral unmixing and disparity correction to generate a multispectral datacube, which is then sent to the datacube analysis servers 1615. Some implementations can perform full processing and analysis locally on the multispectral multi-aperture imaging system 1605, and may send the multispectral datacube and resulting analysis to the datacube analysis servers 1615 for aggregate analysis and/or use in training or retraining machine learning models. As such, the datacube analysis servers 1615 may provide updated machine learning models to the multispectral multi-aperture imaging system 1605. The processing load of generating the end result of analyzing the multispectral datacube can be split between the multi-aperture imaging system 1605 and the datacube analysis servers 1615 in various ways, depending upon the processing power of the multi-aperture imaging system 1605.

The network 1610 can comprise any appropriate network, including an intranet, the Internet, a cellular network, a local area network or any other such network or combination thereof. User devices 1620 can include any network-equipped computing device, for example desktop computers, laptops, smartphones, tablets, e-readers, or gaming consoles, and the like. For example, results (e.g., classified images) determined by the multi-aperture imaging system 1605 and the datacube analysis servers 1615 may be sent to designated user devices of patients, doctors, hospital information systems storing electronic patient medical records, and/or centralized health databases (e.g., of the Center for Disease Control) in tissue classification scenarios.

Example Implementation Outcomes

Background: Morbidity and mortality resulting from burns is a major problem for wounded warfighters and their care providers. The incidence of burns among combat casualties has historically been 5-20% with approximately 20% of these casualties requiring complex burn surgery at the US Army Institute of Surgical Research (ISR) burn center or equivalent. Burn surgery requires specialized training and is therefore provided by ISR staff rather than US Military Hospital staff. The limited number of burn specialists leads to high logistical complexity of providing care to burned soldiers. Therefore, a new objective method of pre-operative and intra-operative detection of burn depth could enable a broader pool of medical staff, including non-ISR personnel, to be enlisted in the care of patients with burn wounds sustained in combat. This augmented pool of care providers could then be leveraged to provide more complex burn care further forward in the role of care of warfighters with burn wounds.

In order to begin addressing this need, a novel cart-based imaging device that uses multispectral imaging (MSI) and artificial intelligence (AI) algorithms to aide in the preoperative determination of burn healing potential has been developed. This device acquires images from a wide area of tissue (e.g., 5.9×7.9 in2) in a short amount of time (e.g., within 6, 5, 4, 3, 2, or 1 second(s)) and does not require the injection of imaging contrast agents. This study based in a civilian population shows that the accuracy of this device in determining burn healing potential exceeds clinical judgement by burn experts (e.g., 70-80%).

Methods: Civilian subjects with various burn severities were imaged within 72 hours of their burn injury and then at several subsequent time points up to 7 days post-burn. True burn severity in each image was determined using either 3-week healing assessments or punch biopsies. The accuracy of the device to identify and differentiate healing and non-healing burn tissue in first, second, and third degree burn injuries was analyzed on a per image pixel basis.

Results: Data were collected from 38 civilian subjects with 58 total burns and 393 images. The AI algorithm achieved 87.5% sensitivity and 90.7% specificity in predicting non-healing burn tissue.

Conclusions: The device and its AI algorithm demonstrated accuracy in determining burn healing potential that exceeds the accuracy of clinical judgement of burn experts. Future work is focused on redesigning the device for portability and evaluating its use in an intra-operative setting. Design changes for portability include reducing the size of the device to a portable system, increasing the field of view, reducing acquisition time to a single snapshot, and evaluating the device for use in an intra-operative setting using a porcine model. These developments have been implemented in a benchtop MSI subsystem that shows equivalency in basic imaging tests.

Additional Illuminants for Image Registration

Figure 21:
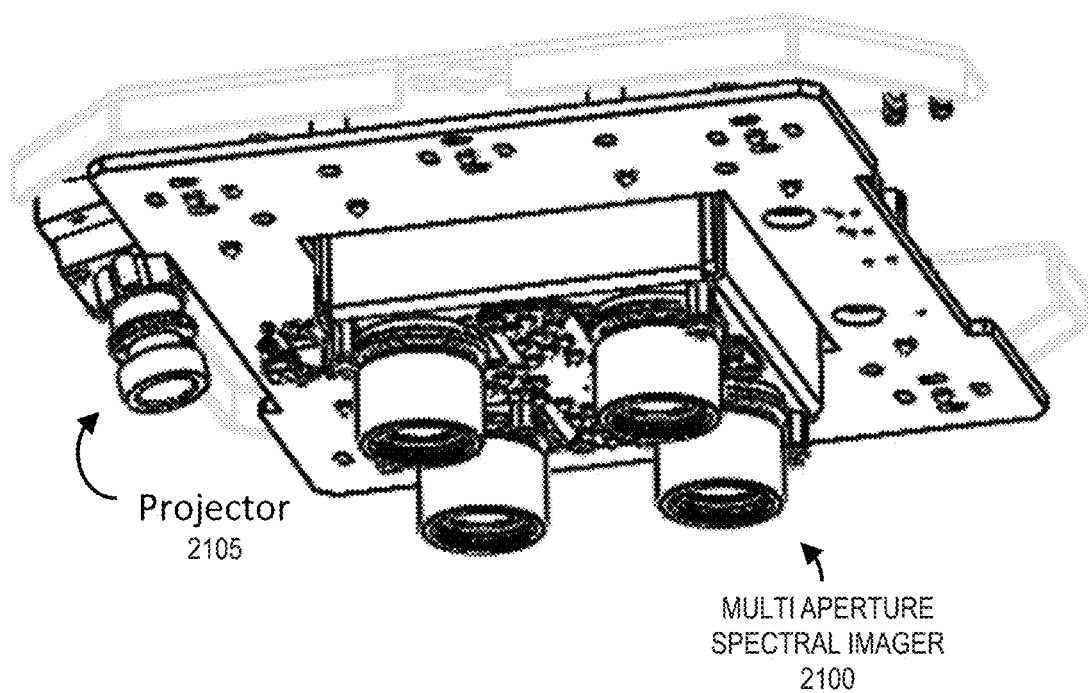
FIG. 21 illustrates an example multispectral, multi-aperture imaging system including an additional illuminant for improved image registration.

In various embodiments, one or more additional illuminants may be used in conjunction with any of the embodiments disclosed herein in order to improve the accuracy of image registration. FIG. 21 illustrates an example embodiment of a multi aperture spectral imager 2100 including a projector 2105. In some embodiments, the projector 2105 or other suitable illuminant may be, for example, one of the illuminants 1165 described with reference to FIG. 12 above. In embodiments including an additional illuminant such as a projector 2105 for registration, the method may further include an additional exposure. The additional illuminant such as the projector 2105 can project, into the field of view of the imager 2100, one or more points, fringes, grids, random speckle, or any other suitable spatial pattern in a spectral band, multiple spectral bands, or in a broad band, that are individually or cumulatively visible in all cameras of the imager 2100. For example, the projector 2105 may project light of the shared or common channel, broadband illumination, or cumulatively visible illumination that can be used to confirm the accuracy of the registration of the image calculated based on the aforementioned common band approach. As used herein, "cumulatively visible illumination" refers to a plurality of wavelengths selected such that the pattern is transduced by each of the image sensors in the multi-spectral imaging system. For example, cumulatively visible illumination may include a plurality of wavelengths such that every channel transduces at least one of the plurality of wavelengths, even if none of the plurality of wavelengths is common to all channels. In some embodiments, the type of pattern projected by the projector 2105 may be selected based on the number of apertures in which the pattern will be imaged. For example, if the pattern will be seen by only one aperture, the pattern may preferably by relatively dense (e.g., may have a relatively narrow autocorrelation such as on the order of 1-10 pixels, 20 pixels, less than 50 pixels, less than 100 pixels, etc.), while less dense or less narrowly autocorrelated patterns may be useful where the pattern will be imaged by a plurality of apertures. In some embodiments, the additional exposure that is captured with the projected spatial pattern is included in the calculation of disparity in order to improve the accuracy of the registration compared to embodiments without the exposure captured with a projected spatial pattern. In some embodiments, the additional illuminant projects, into the field of view of the imager, fringes in a spectral band, multiple spectral bands, or in a broad band, that are individually or cumulatively visible in all cameras, such as in the shared or common channel, or broadband illumination which can be used to improve the registration of images based on the phase of fringes. In some embodiments, the additional illuminant projects, into the field of view of the imager, a plurality of unique spatial arrangement of dots, grids, and/or speckle in a spectral band, multiple spectral bands, or in a broad band, that are individually or cumulatively visible in all cameras, such as in the shared or common channel, or broadband illumination which can be used to improve the registration of images. In some embodiments, the method further includes an additional sensor with a single aperture or a plurality of apertures, which can detect the shape of the object or objects in the field of view. For example, the sensor may use LIDAR, light field, or ultrasound techniques, to further improve the accuracy of registration of the images using the aforementioned common band approach. This additional sensor may be a single aperture or a multi-aperture sensor, sensitive to light-field information, or it may be sensitive to other signals, such as ultrasound or pulsed lasers.

Machine Learning Implementations for Wound Assessment, Healing Prediction, and Treatment Example embodiments of machine learning systems and methods for wound assessment, healing prediction, and therapy will now be described. Any of the various imaging devices, systems, methods, techniques, and algorithms described herein may be applied in the field of wound imaging and analysis. The following implementations may include the acquisition of one or more images of a wound in one or more known wavelength bands, and may include, based on the one or more images, any one or more the following: segmentation of the image into a wound portion and a non-wound portion of the image, prediction of percent area reduction of the wound after a predetermined time period, prediction of healing potenional of individual sections of the wound after a predetermined time period, display of a visual representation associated with any such segmentation or prediction, indication of a selection between a standard wound care therapy and an advanced wound care therapy, and the like.

In various embodiments, a wound assessment system or a clinician can determine an appropriate level of wound care therapy based on the results of the machine learning algorithms disclosed herein. For example, if an output of a wound healing prediction system indicates that an imaged wound will close by more than 50% within 30 days, the system can apply or inform a health care practitioner or patient to apply a standard of care therapy; if the output indicates that the wound will not close by more than 50% in 30 days, the system can apply or inform the health care practitioner or patient to use one or more advanced wound care therapies.

Figure 22:
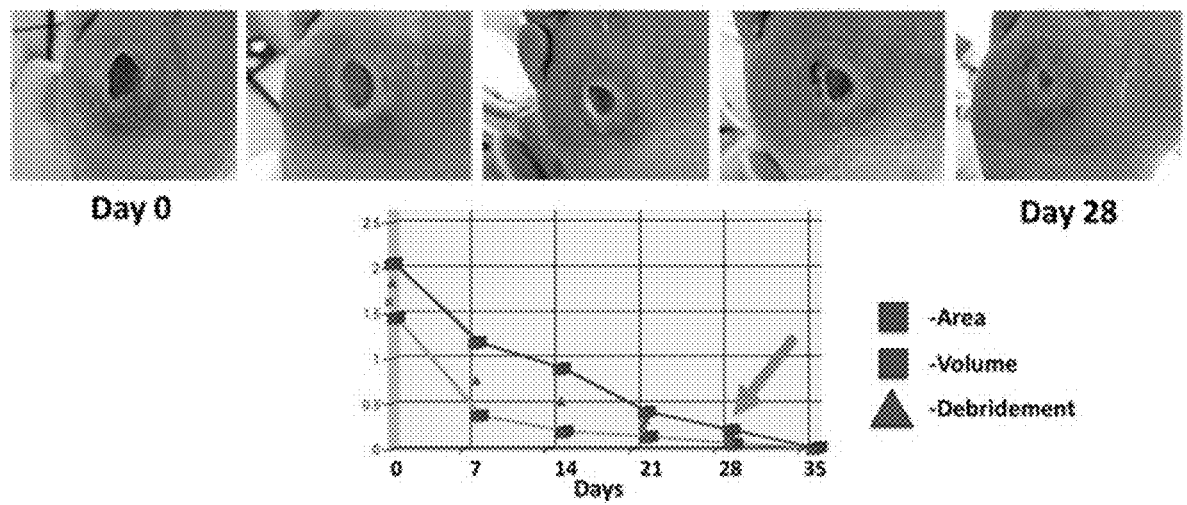
FIG. 22 shows an example time progression of a healing diabetic foot ulcer (DFU) with corresponding area, volume, and debridement measurements.

Under existing wound treatment, a wound such as a diabetic foot ulcer (DFU) may initially receive one or more standard wound care therapies for the initial 30 days of treatment, such as Standard of Care (SOC) therapy as defined by the Centers for Medicare and Medicaid. As one example of a standard wound care regimen, SOC therapy can include one or more of: optimization of nutritional status; debridement by any means to remove devitalized tissue; maintenance of a clean, moist bed of granulation tissue with appropriate moist dressings; necessary treatment to resolve any infection that may be present; addressing any deficiencies in vascular perfusion to the extremity with the DFU; offloading of pressure from the DFU; and appropriate glucose control. During this initial period of 30 days of SOC therapy, measurable signs of DFU healing are defined as: decrease in DFU size (either wound surface area or wound volume), decrease in amount of DFU exudate, and decrease in amount of necrotic tissue within the DFU. An example progression of a healing DFU is illustrated in FIG. 22.

Figure 23:
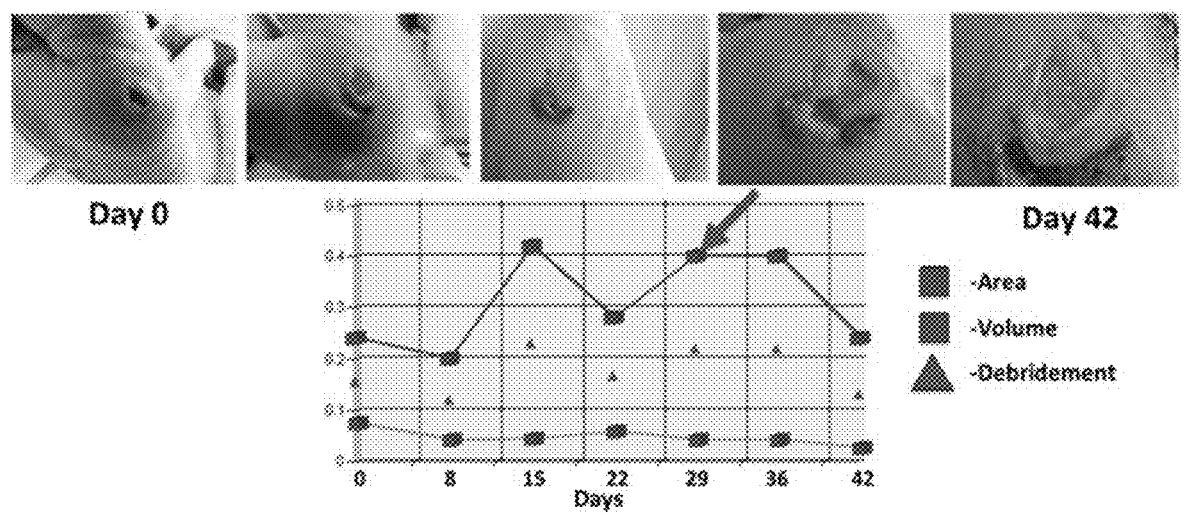
FIG. 23 shows an example time progression of a non-healing DFU with corresponding area, volume, and debridement measurements.

If healing is not observed during this initial period of 30 days of SOC therapy, Advanced Wound Care (AWC) therapies are generally indicated. The Centers for Medicare and Medicaid have no summary or definition of AWC therapies but are considered to be any therapy outside of SOC therapy as defined above. AWC therapies are an area of intense research and innovation with near-constant introduction of new options to be used in clinical practice. Therefore, coverage of AWC therapies are determined on an individual basis and a treatment considered AWC may not be covered for reimbursement for some patients. Based on this understanding, AWC therapies include, but are not limited to, any one or more of: hyperbaric oxygen therapy; negative-pressure wound therapy; bioengineered skin substitutes; synthetic growth factors; extracellular matrix proteins; matrix metalloproteinase modulators; and electrical stimulation therapy. An example progression of a non-healing DFU is illustrated in FIG. 23.

In various embodiments, wound assessment and/or healing predictions described herein may be accomplished based on one or more images of the wound, either alone or based on a combination of both patient health data (e.g., one or more health metric values, clinical features, etc.) and images of the wound. The described techniques can capture single images or a set of multispectral images (MSI) of a patient tissue site including an ulcer or other wound, process the image(s) using a machine learning system as described herein, and output one or more predicted healing parameters. A variety of healing parameters may be predicted by the present technology. By way of non-limiting example, some predicted healing parameters may include (1) a binary yes/no regarding whether the ulcer will heal to greater than 50% area reduction (or another threshold percentage, as desired according to clinical standards) within a period of 30 days (or another time period, as desired according to clinical standards); (2) a percentage likelihood that the ulcer will heal to greater than 50% area reduction (or another threshold percentage, as desired according to clinical standards) within a period of 30 days (or another time period, as desired according to clinical standards); or (3) a prediction regarding the actual area reduction that is expected within 30 days (or another time period, as desired according to clinical standards) due to healing of the ulcer. In further examples, systems of the present technology may provide a binary yes/no or a percentage likelihood of healing with regard to smaller portions of a wound, such as for individual pixels or subsets of pixels of a wound image, with the yes/no or percentage likelihood indicating whether each individual portion of the wound is likely to be healing tissue or non-healing tissue following the predetermined time period.

Figure 24:
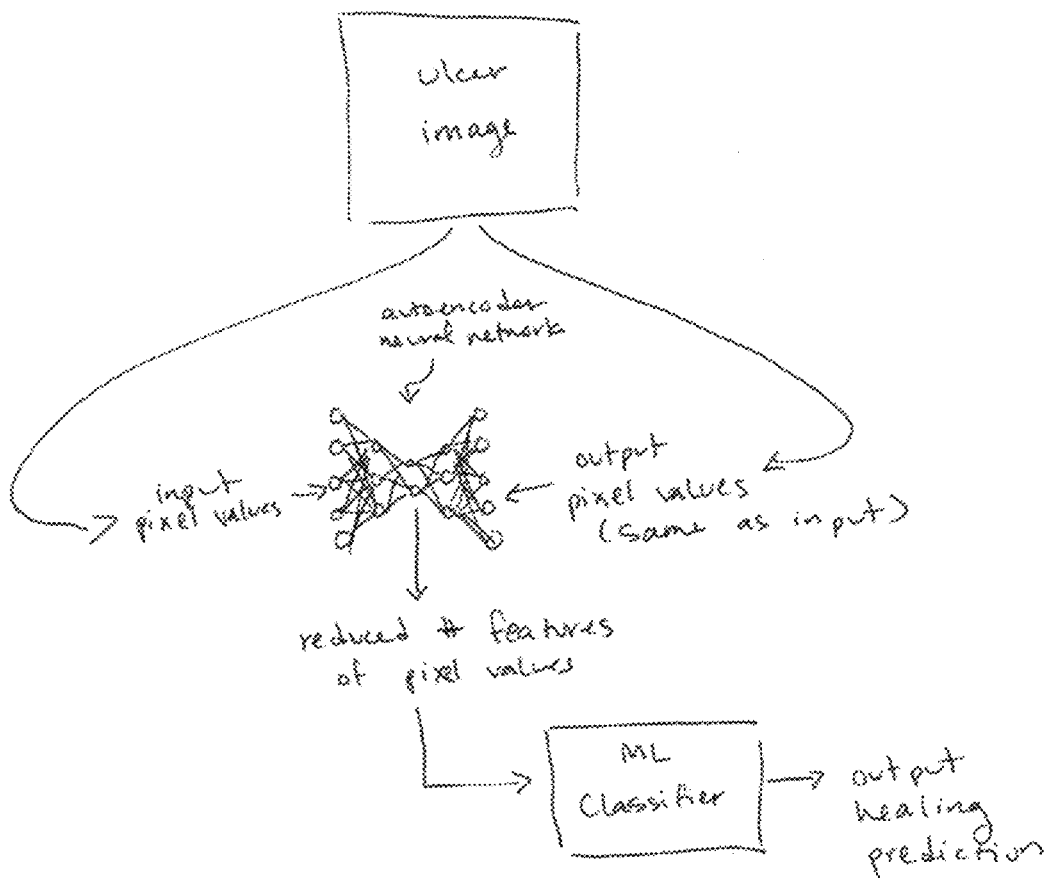
FIG. 24 schematically illustrates an example machine learning system for generating a healing prediction based on one or more images of a DFU.

FIG. 24 presents one example approach to providing such healing predictions. As illustrated, an image of a wound, or a set of multispectral images of the wound captured at different wavelengths, either at different times or simultaneously using a multispectral image sensor, may be used to provide both the input and output values to a neural network such as an autoencoder neural network, which is a type of artificial neural network as described in greater detail below. This type of neural network is able to generate a reduced feature representation of the input, here a reduced number of values (e.g., numerical values) representing the pixel values in the input image(s). This can in turn be provided to a machine learning classifier, for example a fully connected feedforward artificial neural network or the system shown in FIG. 25, in order to output a healing prediction for the imaged ulcer or other wound.

Figure 25:
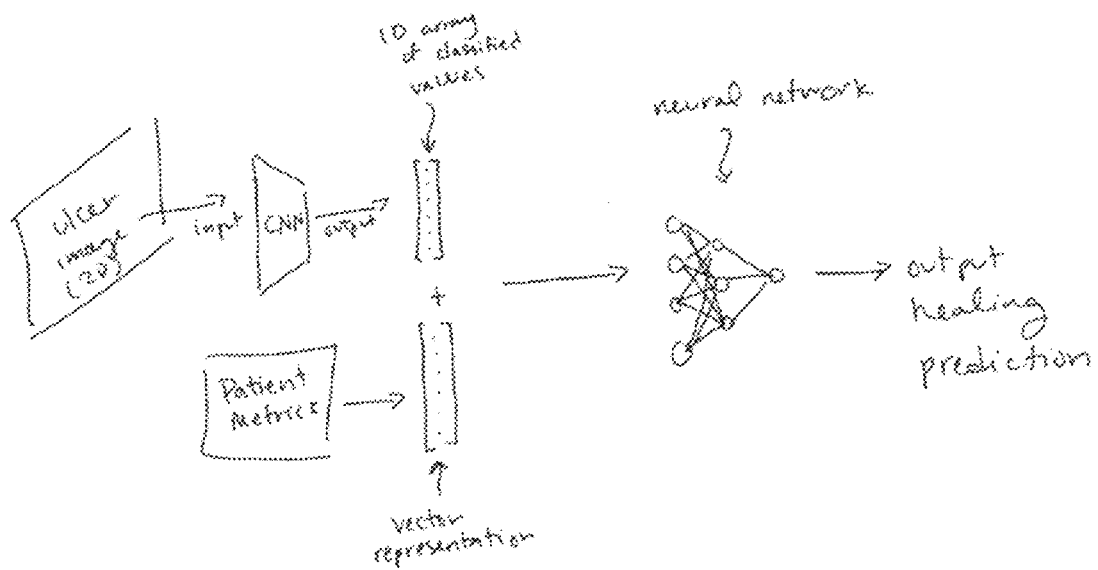
FIG. 25 schematically illustrates an example machine learning system for generating a healing prediction based on one or more images of a DFU and one or more patient health metrics.

FIG. 25 presents another approach to providing such healing predictions. As illustrated, an image (or set of multispectral images captured at different wavelengths, either at different times or simultaneously using a multispectral image sensor) is provided as input into a neural network such as a convolutional neural network ("CNN"). The CNN takes this two-dimensional ("2D") array of pixel values (e.g., values along both the height and width of the image sensor used to capture the image data) and outputs a one-dimensional ("1D") representation of the image. These values can represent classifications of each pixel in the input image, for example according to one or more physiological states pertaining to ulcers or other wounds.

As shown in FIG. 25, a patient metric data repository can store other types of information about the patient, referred to herein as patient metrics, clinical variables, or health metric values. Patient metrics can include textual information describing characteristics of the patient, for example, the area of the ulcer, the body mass index (BMI) of the patient, the number of other wounds the patient has or has had, diabetic status, whether the patient is or has recently taken immunosuppressant drugs (e.g., chemotherapy) or other drugs that positively or adversely affect wound healing rate, HbA1c, chronic kidney failure stage IV, type II vs. type I diabetes, chronic anemia, asthma, drug use, smoking status, diabetic neuropathy, deep vein thrombosis, previous myocardial infarction, transient ischemic attacks, or sleep apnea or any combination thereof. However, a variety of other metrics may be used. A number of example metrics are provided in Table 1 below.

TABLE 1

Example clinical variables for wound image analysis

| Variable | Description |
| --- | --- |
| General demographics | |
| Age | Age of the patient. |
| Gender | Gender of the patient. |
| Race | Race of the patient. |
| Ethnicity | Ethnicity of the patient. |
| Height | Height of patient. |
| Weight | Weight of patient. |
| BMI | Body-mass-index of patient. |
| DFU History | |
| Prior DFU | Number of prior DFUs |
| Prior DFU Healing | Healing rates and times of prior DFUs |
| Prior DFU Location | Locations of prior DFUs |
| Prior DFU Size | Size of prior DFUs |
| Current DFU | Number of current DFUs |
| Current DFU Location | Location of current DFUs |
| Current DFU Size | Size of current DFUs |
| DFU Treatment Duration | Duration of current DFUs prior to seeking treatment. |
| DFU Treatment Prior | Prior treatments and duration of treatments performed on current DFUs. |
| DFU Treatment Planned | Planned treatment of current DFUs. |
| DFU Current Healing | Healing response of current DFUs to prior treatments. |
| DFU Stage | Class and/or stage of current DFUs using widely accepted grading schemes including the Wagner classification. |
| DFU Cause | Causative event of current DFUs. |
| DFU Infection | Infection status of current DFUs. |
| DFU Infection Cause | Causative microorganism of current or prior DFU infections. |
| DFU CFU | Colony-forming-unit count of current DFU infections. |
| Compliance | |
| Socio-Economic | Socio-economic status of the patient. |
| Mal-Compliance | History of mal-compliance with healthcare. |
| Functional Status | Current functional status of patient. |
| Endocrine | |
| Diabetes Mellitus Duration | Duration of diabetes mellitus diagnosis for patient. |
| Diabetes Mellitus Type | Type of diabetes mellitus diagnosed in patient. |
| Hemoglobin A1C % | Current or most recent hemoglobin A1C % value for patient. |
| Serum Glucose | Current or most recent serum glucose value for patient. |
| Diabetes Mellitus Medications | Current glycemic control mediations, including insulin, taken by patient. |
| Diabetes Mellitus Neuropathy | Presence of diabetic peripheral neuropathy. |
| Diabetes Mellitus Foot | Presence of foot malformations due to diabetes mellitus and/or peripheral neuropathy. |
| Steroids | Current or prior use of glucocorticoid medications. |
| Other Endocrine | Current or prior medical diagnosis directly or indirectly altering endocrine or metabolic systems. |
| Other Endocrine Medications | Current or prior medications directly or indirectly altering endocrine or metabolic systems. |

TABLE 1-continued

Example clinical variables for wound image analysis

| Variable | Description |
| --- | --- |
| Cardiovascular | |
| Peripheral Vascular Disease | Presence of peripheral vascular disease. |
| Ankle Brachial Index | Current or most recent ankle-brachial index for available extremities. |
| Endovascular Procedures | History and locations of prior extremity endovascular angioplasty, stenting, or other procedure to treat peripheral vascular disease. |
| Bypass Procedures | History and locations of prior extremity surgical bypass procedures to treat peripheral vascular disease. |
| Bypass Healing | Healing rates and times of prior extremity surgical bypass procedures. |
| Endocarditis | Current or prior endocarditis. |
| Cerebrovascular Accidents | Current or prior cerebrovascular accidents (strokes). |
| Neurological Deficits | Neurological deficits remaining from prior cerebrovascular accidents. |
| Anemia | Current or prior diagnosis of anemia |
| Hemoglobin/Hematocrit | Current or most recent serum hemoglobin and hematocrit values. |
| Venous Thrombosis | Current or prior diagnosis of deep or superficial venous thrombosis. |
| Anticoagulation Medications | Current or prior use of anti-coagulation medications. |
| Atrial Fibrillation | Current or prior diagnosis of atrial fibrillation. |
| Heart Failure | Current or prior diagnosis of heart failure of any type. |
| Heart Attack | Current or prior diagnosis of myocardial infarction (heart attack). |
| Cardiac Stenting | Prior history of cardiac stenting procedures. |
| Platelet Medications | Current or prior anti-platelet or otherwise platelet-altering medications. |
| Calcium Blocking Medications | Current use of calcium blocking medications. |
| Sympathetic Medications | Current use of sympathetic-modifying medications including medications inducing beta-blockade. |
| Diuretic Medications | Current use of diuresis-inducing medications. |
| Renin Aldosterone Medications | Current use of medications altering the renin-aldosterone pathway. |
| Dromotropic Medications | Current use of medications altering the inotropy, chronotropy, or dromotropy of the heart. |
| Lipid Cholesterol Medications | Current use of medications altering lipid or cholesterol pathways. |
| Musculoskeletal | |
| Other Foot Deformities | Presence of foot malformations not due to diabetes mellitus and/or peripheral neuropathy. |
| Prior Amputations | History and locations of prior extremity amputations. |
| Prior Amputation Healing | Healing rates and times of prior amputations. |
| Nutrition | |
| Nutrition Deficit | Current diagnosis of malnutrition or malnourishment of any type including deficiencies of calories, fats, proteins, vitamins, and minerals. |
| Nutrition Illness | Presence of any medical illness directly or indirectly altering nutrition status of any type. |
| Nutrition Markers | Serum albumin, pre-albumin, or transferrin values below the normal range set by the measuring facility. |
| Nutrition Signs Symptoms | Presence of physical exam findings or patient history known to be indicative of malnutrition. |
| Nutrition Treatment | Current treatment for malnutrition or malnourishment of any type including enteral nutrition, parenteral nutrition, and supplementation of calories, fats, proteins, vitamins, and minerals. |
| Infectious Disease | |
| Infections Wound | Current or prior infections of any wounds. |
| Infections Deep | Current or prior diagnosis of deep tissue infections including osteomyelitis. |
| Infections Cause | Main causative microorganism for current or prior wound infections. |
| Infections Systemic | Current diagnosis of infection located anywhere. |
| Antibiotics Usage | Current or prior use of antibiotic treatment defined as prolonged. |
| Renal | |
| Chronic Kidney Disease | Current or prior diagnosis of chronic kidney disease. |
| Kidney Disease Stage | Stage or severity of chronic kidney disease. |
| Dialysis | Current need for dialysis of any type. |

TABLE 1-continued

Example clinical variables for wound image analysis

| Variable | Description |
| --- | --- |
| Creatinine | Current or most recent serum creatinine value. |
| Creatinine Clearance | Current or most recent creatinine clearance value. |
| Acute Kidney Injury | Presence of acute kidney injury. |
| Ob/Gyn | |
| Pregnancy | Current pregnancy status of the patient. |
| Past Pregnancy | Pregnancy history of the patient. |
| Menopause | Pre- or Post-menopausal status of the patient. |
| Hormone Medications | Current hormonal medications taken by patient. |
| Other | |
| Tobacco Use | Current and prior tobacco use status of patient. |
| Tobacco Method | Method of current or prior tobacco use. |
| Tobacco Amount | Amount of current or prior tobacco use. |
| Alcohol Use | Current and prior alcohol use of patient. |
| Alcohol Abuse | Current or prior alcohol abuse. |
| Illicit Drug Use | Current or prior illicit drug use, including marijuana. |
| Cancer Status | Current or prior diagnosis of cancers. |
| Cancer Locations | Locations and types of prior cancers. |
| Cancer Recurrence | Presence and location of cancer recurrences. |
| Chemotherapy Radiation | Current or prior treatment with chemotherapy medications, radiation therapy, or other treatments utilized for cancer. |
| Autoimmune Disorder | Current or prior diagnosis of autoimmune disorders. |
| Autoimmune Treatments | Current or prior treatments for autoimmune disorders including immunosuppressants. |
| Transplant Status | Prior history of organ transplant surgery. |
| Transplant Medications | Current or prior medications for management of transplanted organs including immunosuppressants. |
| Asthma | Current or prior history of asthma. |
| Asthma Treatments | Current or prior treatments for asthma including corticosteroids. |
| Liver Cirrhosis | Current or prior diagnosis of liver cirrhosis. |
| MELD Score | Current or most recent MELD or MELD XI score. |
| Child-Pugh Score | Current or most recent Child-Pugh score. |
| Other laboratory values | |
| Sodium | Current or most recent serum sodium value. |
| Potassium | Current or most recent serum potassium value. |
| Chloride | Current or most recent serum chloride value. |
| Bicarbonate | Current or most recent serum bicarbonate value. |
| Bilirubin | Current or most recent serum total and direct bilirubin values. |
| Aspartate Transaminase | Current or most recent serum aspartate transaminase value. |
| Alanine Transaminase | Current or most recent serum alanine transaminase value. |
| Total Protein | Current or most recent serum total protein value. |
| White Blood Cell | Current or most recent serum white blood cell count. |
| Platelet | Current or most recent serum platelet count. |
| Lactate | Current or most recent serum lactate value. |
| Lactate Dehydrogenase | Current or most recent serum lactate dehydrogenase value. |
| Calcium | Current or most recent serum calcium value. |
| Magnesium | Current or most recent serum magnesium value. |
| Phosphorus | Current or most recent serum phosphorus value. |
| Procalcitonin | Current or most recent serum procalcitonin value. |
| Other medications | |

These metrics can be converted into a vector representation through appropriate processing, for example through word-to-vec embeddings, a vector having binary values representing whether the patient does or does not have the patient metric (e.g., does or does not have type I diabetes), or numerical values representing a degree to which the patient has each patient metric. Various embodiments can use any one of these patient metrics or a combination of some or all of the patient metrics to improve the accuracy of predicted healing parameters generated by the systems and methods of the present technology. In an example trial, it was determined that image data taken during the initial clinical visit for a DFU, analyzed alone without considering clinical variables, could accurately predict percent area reduction of the DFU with approximately 67% accuracy. Predictions based on patient medical history alone were approximately 76% accurate, with the most important features being: wound area, BMI, number of previous wounds, HbA1c, chronic kidney failure stage IV, type II vs type I diabetes, chronic anemia, asthma, drug use, smoking status, diabetic neuropathy, deep vein thrombosis, previous myocardial infarction, transient ischemic attacks, and sleep apnea. When combining these medical variables with image data we observed an increase in prediction accuracy to approximately 78%.

In one example embodiment as shown in FIG. 25, the 1D representation of the image data can be concatenated with the vector representation of the patient metrics. This concatenated value can then be provided as an input into a fully connected neural network, which outputs a predicted healing parameter.

The system shown in FIG. 25 can be considered as a single machine learning system having multiple machine learning models as well as the patient metric vector generator. In some embodiments, this entire system can be trained in an end-to-end fashion such that the CNN and fully connected network tune their parameters through backpropagation in order to be able to generate predicted healing parameters from input images, with the patient metric vector added to the values passed between the CNN and the fully connected network.

Example Machine Learning Models

Artificial neural networks are artificial in the sense that they are computational entities, inspired by biological neural networks but modified for implementation by computing devices. Artificial neural networks are used to model complex relationships between inputs and outputs or to find patterns in data, where the dependency between the inputs and the outputs cannot be easily ascertained. A neural network typically includes an input layer, one or more intermediate ("hidden") layers, and an output layer, with each layer including a number of nodes. The number of nodes can vary between layers. A neural network is considered "deep" when it includes two or more hidden layers. The nodes in each layer connect to some or all nodes in the subsequent layer and the weights of these connections are typically learned based on training data during the training process, for example, through backpropagation in which the network parameters are tuned to produce expected outputs given corresponding inputs in labeled training data. Thus, an artificial neural network may be an adaptive system that is configured to change its structure (e.g., the connection configuration and/or weights) based on information that flows through the network during training, and the weights of the hidden layers can be considered as an encoding of meaningful patterns in the data.

A fully connected neural network is one in which each node in the input layer is connected to each node in the subsequent layer (the first hidden layer), each node in that first hidden layer is connected in turn to each node in the subsequent hidden layer, and so on until each node in the final hidden layer is connected to each node in the output layer.

Autoencoders are neural networks that include an encoder and a decoder. The goal of certain autoencoders is to compress the input data with the encoder, then decompress this encoded data with the decoder such that the output is a good/perfect reconstruction of the original input data. Example autoencoder neural networks described herein, such as the autoencoder neural network illustrated in FIG. 24, can take the image pixel values of an image of a wound (e.g., structured in vector or matrix form) as inputs into its input layer. The subsequent one or more layers, or "encoder layers," encode this information by lowering its dimensionality (e.g., by representing the input using fewer dimensions than its original n-dimensions), and the additional one or more hidden layers subsequent to the encoder layers ("decoder layers") decode this information to generate an output feature vector at the output layer. An example training process for the autoencoder neural network can be unsupervised, in that the autoencoder learns the parameters of its hidden layers that produce the same output as the provided input. As such, the number of nodes in the input and output layers are typically the same. The dimensionality reduction allows the autoencoder neural network to learn the most salient features of the input images, where the innermost layer (or another inner layer) of the autoencoder represents a "feature reduction" version of the input. In some examples, this can serve to reduce an image having, for example, approximately 1 million pixels (where each pixel value can be considered as a separate feature of the image) to a feature set of around 50 values. This reduced-dimensionality representation of the images can be used by another machine learning model, for example, the classifier of FIG. 25 or a suitable CNN or other neural network, in order to output a predicted healing parameter.

A CNN is a type of artificial neural network, and like the artificial neural networks described above, a CNN is made up of nodes and has learnable weights between nodes. However, the layers of a CNN can have nodes arranged in three dimensions: width, height, and depth, corresponding to the 2×2 array of pixel values in each image frame (e.g., the width and height) and to the number of image frames in a sequence of images (e.g., the depth). In some embodiments, the nodes of a layer may only be locally connected to a small region of the width and height of the preceding layer, called a receptive field. The hidden layer weights can take the form of a convolutional filter applied to the receptive field. In some embodiments, the convolutional filters can be two-dimensional, and thus, convolutions with the same filter can be repeated for each frame (or convolved transformation of an image) in the input volume or for designated subset of the frames. In other embodiments, the convolutional filters can be three-dimensional and thus extend through the full depth of nodes of the input volume. The nodes in each convolutional layer of a CNN can share weights such that the convolutional filter of a given layer is replicated across the entire width and height of the input volume (e.g., across an entire frame), reducing the overall number of trainable weights and increasing applicability of the CNN to data sets outside of the training data. Values of a layer may be pooled to reduce the number of computations in a subsequent layer (e.g., values representing certain pixels may be passed forward while others are discarded), and further along the depth of the CNN pool masks may reintroduce any discarded values to return the number of data points to the previous size. A number of layers, optionally with some being fully connected, can be stacked to form the CNN architecture. During training, an artificial neural network can be exposed to pairs in its training data and can modify its parameters to be able to predict the output of a pair when provided with the input.

Artificial intelligence describes computerized systems that can perform tasks typically considered to require human intelligence. Here, the disclosed artificial intelligence systems can perform image (and other data) analysis that, without the disclosed technology, may otherwise require the skill and intelligence of a human physician. Beneficially, the disclosed artificial intelligence systems can make such predictions upon an initial patient visit rather than requiring a wait time of 30 days to assess wound healing.

The capability to learn is an important aspect of intelligence, as a system without this capability generally cannot become more intelligent from experience. Machine learning is a field of computer science that gives computers the ability to learn without being explicitly programmed, for example, enabling artificial intelligence systems to learn complex tasks or adapt to changing environments. The disclosed machine learning systems can learn to determine wound healing potential through being exposed to large volumes of labeled training data. Through this machine learning, the disclosed artificially intelligent systems can learn new relationships between the appearances of wounds (as captured in image data such as MSI) and the healing potential of the wound.

The disclosed artificially intelligent machine learning systems include computer hardware one or more memories and one or more processors, for example, as described with reference to the various imaging systems herein. Any of the machine learning systems and/or methods of the present technology may be implemented on or in communication with processors and/or memory of the various imaging systems and devices of the present disclosure.

Example Multispectal DFU Imaging Implementation

In an example application of the machine learning systems and methods disclosed herein, machine learning algorithms consistent with those described above were used to predict the percent area reduction (PAR) of an imaged wound at day 30, following imaging on day 0. To accomplish this prediction, a machine learning algorithm was trained to take MSI data and clinical variables as inputs and to output a scalar value representing the predicted PAR. After 30 days, each wound was evaluated to measure its true PAR. The predicted PAR was compared to the true PAR measured during a 30-day healing assessment conducted on the wound. The performance of the algorithm was scored using a coefficient of determination ($R^2$).

The machine learning algorithm for this example application was a bagging ensemble of decision tree classifiers, fit using data from a database of DFU image. Other suitable classifier ensembles may equally be implemented, such as the XGBoost algorithm or the like. The database of DFU images contained 29 individual images of diabetic foot ulcers obtained from 15 subjects. For each image, the true PAR measured at day 30 was known. Algorithm training was conducted using the leave-one-out cross-validation (LOOCV) procedure. The $R^2$ score was computed after combining the predicted results on the test image from each fold of LOOCV.

Figure 26:
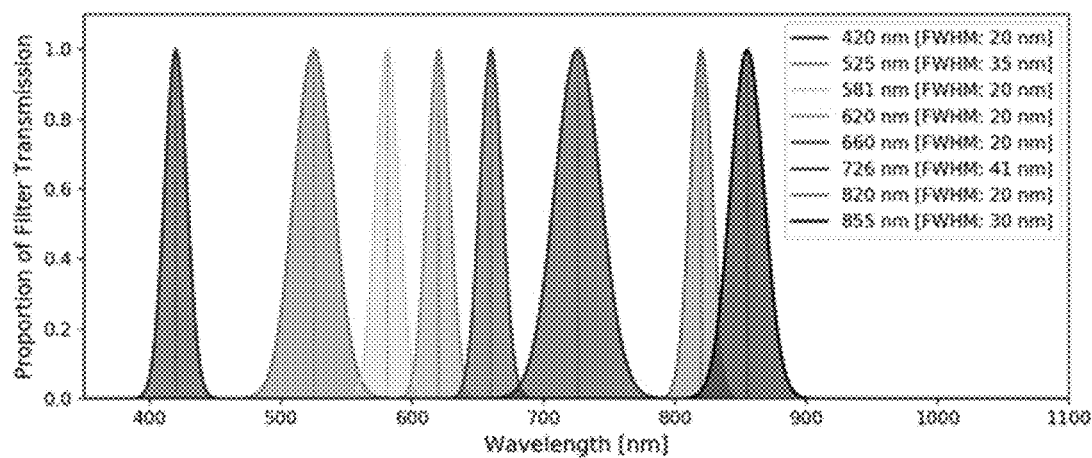
FIG. 26 illustrates an example set of wavelength bands used for spectral and/or multi-spectral imaging for image segmentation and/or generation of predicted healing parameters in accordance with the present technology.

The MSI data consisted of 8 channels of 2D images, where each of the 8 channels represented the diffuse reflectance of light from the tissue at a specific wavelength filter. The field of view of each channel was 15 cm×20 cm with a resolution of 1044 pixels×1408 pixels. The 8 wavelength bands included: 420 nm±20 nm; 525 nm±35 nm; 581 nm±20 nm; 620 nm±20 nm; 660 nm±20 nm; 726 nm±41 nm; 820 nm±20 nm; and 855 nm±30 nm, wherein "±" represents the full width at half maximum of each spectral channel. The 8 wavelength bands are illustrated in FIG. 26. From each channel, the following quantitative features were computed: the mean of all pixel values, the median of all pixel values, and the standard deviation of all pixel values.

Additionally, from each subject, the following clinical variables were obtained: age, level of chronic kidney disease, the length of the DFU at day 0, and the width of the DFU at day 0.

Separate algorithms were generated using features extracted from all possible combinations of the 8 channels (wavelength bands) in the MSI data cube using 1 channel to 8 channels, totaling $C_1(8)+C_2(8)+\ldots+C_8(8)=255$ different feature sets. The $R^2$ values from each combination were calculated and ordered from smallest to largest. The 95% confidence interval of the $R^2$ value was computed from the prediction results of the algorithm trained on each feature set. To determine if a feature set could provide an improvement over random chance, feature sets were identified wherein the value of 0.0 was not contained within the 95% CI of the results of the algorithm trained on that feature set. Additionally, the same analysis was performed an additional 255 times with the inclusion of all the clinical variables in every feature-set. In order to determine whether the clinical variables had an impact on the performance of the algorithm, the mean $R^2$ value from the 255 algorithms trained using the clinical variables was compared to the 255 algorithms trained without the clinical variables using a t-test. The results of the analysis are illustrated in Tables 2 and 3, below. Table 2 illustrates the performance of feature sets including only image data without including clinical variables.

TABLE 2

Top performing algorithms developed on feature sets that did not include clinical data

| Rank | Feature Set | $R^2$ | Lower 95% CI | Upper 95% CI |
|---|---|---|---|---|
| 1 | [420, 726, 855] | 0.53 | 0.34 | 0.72 |
| 2 | [420, 525, 660, 726, 820] | 0.51 | 0.40 | 0.63 |
| 3 | [420, 581, 660, 726, 820, 855] | 0.48 | 0.37 | 0.58 |
| 4 | [420, 525, 581, 620, 660, 726, 855] | 0.48 | 0.38 | 0.57 |
| 5 | [660, 726, 855] | 0.46 | 0.26 | 0.67 |
| ... | ... | ... | ... | ... |
| 251 | [581] | 0.11 | −0.07 | 0.30 |
| 252 | [525] | 0.11 | −0.07 | 0.29 |
| 253 | [620] | 0.10 | −0.08 | 0.28 |
| 254 | [820] | 0.05 | −0.09 | 0.18 |
| 255 | [726] | 0.04 | −0.08 | 0.16 |

As shown in Table 2, among feature sets that did not include the clinical features, the top performing feature-set contained only 3 of the 8 possible channels in the MSI data. It was observed that the 726 nm wavelength band appears in all top 5 feature sets. Only one wavelength band appears in each of the bottom five feature sets. It was further observed that although the 726 nm wavelength band appeared in each of the top 5 feature sets, the 726 nm wavelength band performed the worst when used alone. Table 3 below illustrates the performance of feature sets including image data as well as the clinical variables of age, level of chronic kidney disease, length of the DFU at day 0, and width of the DFU at day 0.

TABLE 3

Top performing algorithms developed on feature sets that included clinical data

| Rank | Feature Set | $R^2$ | Lower 95% CI | Upper 95% CI |
|---|---|---|---|---|
| 1 | [CFs, 420, 525, 581, 620, 660, 726, 820, 855] | 0.56 | 0.47 | 0.65 |
| 2 | [CFs, 420, 581, 660, 820, 855] | 0.55 | 0.44 | 0.65 |
| 3 | [CFs, 420, 581, 660, 726, 855] | 0.52 | 0.41 | 0.63 |
| 4 | [CFs, 660, 726, 855] | 0.49 | 0.31 | 0.67 |
| 5 | [CFs, 525, 581, 620, 820, 855] | 0.46 | 0.24 | 0.68 |
| ... | ... | ... | ... | ... |
| 251 | [CFs, 420, 620, 660] | 0.17 | −0.04 | 0.37 |
| 252 | [CFs, 820] | 0.16 | −0.04 | 0.36 |
| 253 | [CFs, 420, 820, 855] | 0.15 | −0.02 | 0.32 |
| 254 | [CFs, 620] | 0.14 | −0.04 | 0.33 |
| 255 | [CFs, 420] | 0.11 | −0.07 | 0.29 |

Figure 27:
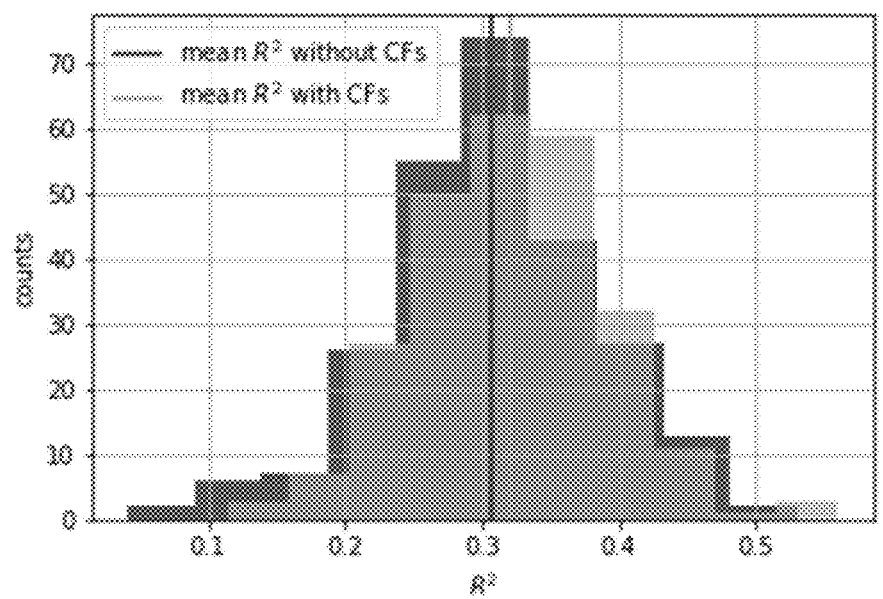
FIG. 27 is a histogram illustrating effects of the inclusion of clinical variables in example wound assessment methods of the present technology.

From feature sets that did include the clinical variables, the top performing feature set contained all 8 of the possible channels in the MSI data. The 855 nm wavelength band appears in all top 5 feature sets. Histograms from models with and without the inclusion of clinical variables are illustrated in FIG. 27, along with vertical lines representing the mean of each distribution.

In comparing the importance of clinical features, it was determined whether the mean $R^2$ between all features sets without clinical variables was equal to the mean $R^2$ from all feature sets that included clinical variables. It was determined that the mean $R^2$ from models trained on feature sets without clinical variables was 0.31, and 0.32 from model trained with clinical variables. In computing the t-test for the difference between means, the p-value was 0.0443. Therefore, it was determined that models trained with clinical variables were significantly more accurate than models trained without clinical features.

Extraction of Features from Image Data

Although the example application described above extracted mean, standard deviation, and median pixel values, it will be understood that a variety of other features may be extracted from image data for use in generating predicted healing parameters. Feature categories include local, semi-local, and global features. Local features may represent texture in an image patch, while global features can include contour representations, shape descriptors, and texture features. Global texture features and local features provide different information about the image because the support over which texture is computed varies. In some cases, global features have the ability to generalize an entire object with a single vector. Local features, on the other hand, are computed at multiple points in the image and are consequently more robust to occlusion and clutter. However, they may require specialized classification algorithms to handle cases in which there are a variable number of feature vectors per image.

Local features may include, for example, scale-invariant feature transform (SIFT), speeded-up robust features (SURF), features from accelerated segment test (FAST), binary robust invariant scalable keypoints (BRISK), Harris corner detection operator, binary robust independent elementary features (BRIEF), oriented FAST and rotated BRIEF (ORB), and KAZE features. Semi-local features may include, for example, edges, splines, lines, and moments in small windows. Global features may include, for example, color, Gabor features, wavelet features, Fourier features, texture features (e.g., $1^{st}$, $2^{nd}$, and high moments), neural network features from 1D, 2D, and 3D convolutions or hidden layers, and principal component analysis (PCA).

Example RGB DFU Imaging Application

As a further example of predicted healing parameter generation, similar MSI methods may be used based on RGB data, such as from a photographic digital camera. In this scenario, the algorithm can take data from an RGB image, and optionally the subject's medical history or other clinical variables, and output a predicted healing parameter such as a conditional probability that indicates whether the DFU will respond to 30 days of standard wound care therapy. In some embodiments, the conditional probability is the probability that the DFU in question is non-healing given the input data, x, to a model parameterized by θ; written as: $P_{model}(y=\text{"non-healing"}|x; \theta)$.

Scoring methods for RGB data may be similar to those for the example MSI application described above. In one example, the predicted non-healing region can be compared to the true non-healing region measured during a 30-day healing assessment conducted on a wound such as a DFU. This comparison represents the performance of the algorithm. The method applied to perform this comparison may be based on the clinical outcome of these output images.

In this example application, four outcomes are possible for each predicted healing parameter generated by the healing prediction algorithm. In a True Positive (TP) outcome, the wound demonstrates less than 50% area reduction (e.g., the DFU is non-healing), and the algorithm predicts less than 50% area reduction (e.g., the device outputs a non-healing prediction). In a True Negative (TN) outcome, the wound demonstrates at least 50% area reduction (e.g., the DFU is healing), and the algorithm predicts at least 50% area reduction (e.g., the device outputs a healing prediction). In a False Positive (FP) outcome, the wound demonstrates at least 50% area reduction, but the algorithm predicts less than 50% area reduction. In a False Negative (FN) outcome, the wound demonstrates less than 50% area reduction, but the algorithm predicts at least 50% area reduction. After prediction and assessment of actual healing, these outcomes can be summarized using the performance metrics of accuracy, sensitivity, and specificity, as shown in Table 4, below.

TABLE 4

Standard performance metrics used to evaluate predictions on images.

| Metric | Computation | |
|---|---|---|
| Accuracy | $\frac{TP + TN}{TP + FP + TN + FN}$ | eq. 1 |
| True Positive Rate (TPR; also known as Sensitivity) | $TPR = \frac{TP}{TP + FN}$ | eq. 2 |
| True Negative Rate (TNR; also known as Specificity) | $TNR = \frac{TN}{TN + FP}$ | eq. 3 |

A database of DFU images was obtained retrospectively and included 149 individual images of diabetic foot ulcers from 82 subjects. Of the DFUs in this data set, 69% were considered "healing" because they reached the target goal of 50% PAR at day 30. The average wound area was 3.7 cm², and the median wound area was 0.6 cm².

Color photography images (RGB images) were used as input data to the models developed. RGB imaged consisted of 3 channels of 2D images, where each of the 3 channels represented the diffuse reflectance of light from the tissue at the wavelengths utilized in a traditional color camera sensor. Images were captured by a clinician using a portable digital camera. The choice of imager, working distance, and field-of-view (FOV) varied between images. Prior to algorithm training, the images were manually cropped to ensure the ulcer was at the center of the FOV. After cropping, the images were interpolated to an image size of 3 channels×256 pixels×256 pixels. Maintaining the aspect ratio of the original image was not controlled for during this interpolation step. However, the aspect ratio could be maintained throughout these pre-processing steps if desired. From each subject, a set of clinical data (e.g., clinical variables or health metric values) was also obtained including their medical history, prior wounds, and blood work.

Two types of algorithm were developed for this analysis. The goal of each algorithm was to initially identify a new representation for the image data that could be combined with the patient health metrics in a traditional machine learning classification approach. There are many available methods to produce this image representation such as principal component analysis (PCA) or scale-invariant feature transform (SIFT). In this example, convolutional neural networks (CNN) were used to transform the images from a matrix (with dimensions 3 channels×265 pixels×256 pixels) to a vector in R". In one example, a separately trained unsupervised approach was used to compress the images, followed by machine learning to make predictions on DFU healing. In a second example, an end-to-end supervised approach was used to predict DFU healing.

Figure 28:
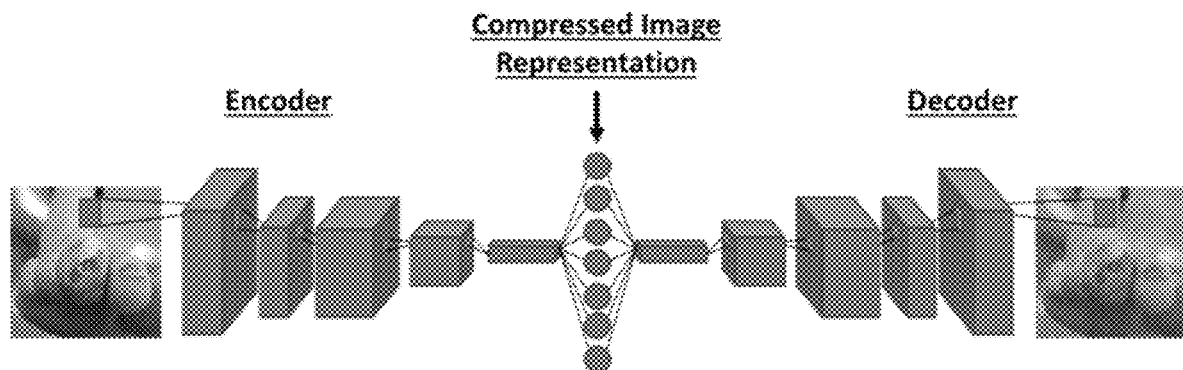
FIG. 28 schematically illustrates an example autoencoder in accordance with the machine learning systems and methods of the present technology.

In the unsupervised feature extraction approach, an autoencoder algorithm was used, for example, consistent with the method of FIG. 24. An example autoencoder is schematically illustrated in FIG. 28. The autoencoder included an encoder module and a decoder module. The encoder module was a 16-layer VGG convolutional network. The $16^{th}$ layer represented the compressed image representation. The decoder module was a 16-layer VGG network with up-sampling functions added and pooling functions eliminated. For each predicted pixel value (in $\mathbb{R}^3$) of the output of the decoder layer, the loss was computed with mean square error (MSE) wherein the target values were the pixel values of the original image.

The autoencoder was pre-trained using PASCAL visual object classes (VOC) data and fine-tuned using the DFU images in the present data set. Individual images comprising 3 channels×265 pixels×256 pixels (65,536 total pixels) were compressed into single vectors of 50 data points. Once trained, the identical encoder-decoder algorithm was used for all images in the data set.

Figure 29:
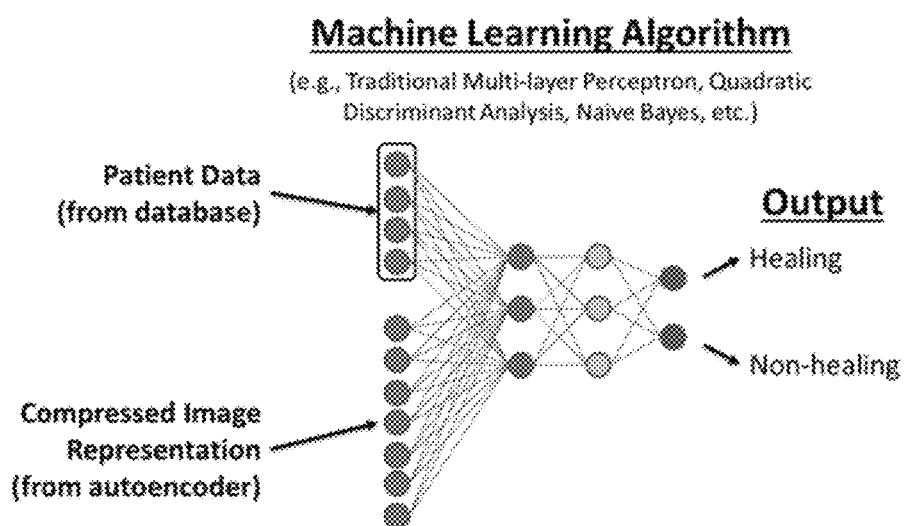
FIG. 29 schematically illustrates an example supervised machine learning algorithm in accordance with the machine learning systems and methods of the present technology.

Upon extraction of the compressed image vector, the compressed image vector was used as an input to a second supervised machine learning algorithm. The combination of image features and patient features were tested using a variety of machine learning algorithms, including logistic regression, K-nearest neighbors, support vector machine, and a variety of decision tree models. An example supervised machine learning algorithm, using the compressed image vector and patient clinical variables as inputs to predict DFU healing, is schematically illustrated in FIG. 29. The machine learning algorithm may be one of various known machine learning algorithms such as a multi-layer perceptron, quadratic discriminant analysis, naïve Bayes, or an ensemble of such algorithms.

The end-to-end machine learning approach, investigated as an alternative to the unsupervised feature extraction approach described above, is schematically illustrated in FIG. 30. In the end-to-end approach, the 16-layer VGG CNN was modified at the first fully connected layer by concatenating the patient health metrics data to the image vector. In this manner, the encoder module and subsequent machine learning algorithm could be trained simultaneously. Other methods of including global variables (e.g., patient health metrics or clinical variables) to improve the performance or alter the purpose of a CNN have been proposed. The most widely used method is the feature-wise linear modulation (FiLM) generator. For the supervised machine learning algorithms, training was performed using a k-fold cross-validation procedure. The results of each image were computed as one of True Positive, True Negative, False Positive, or False Negative. These results were summarized using the performance metrics described in Table 4, above.

Figure 31:
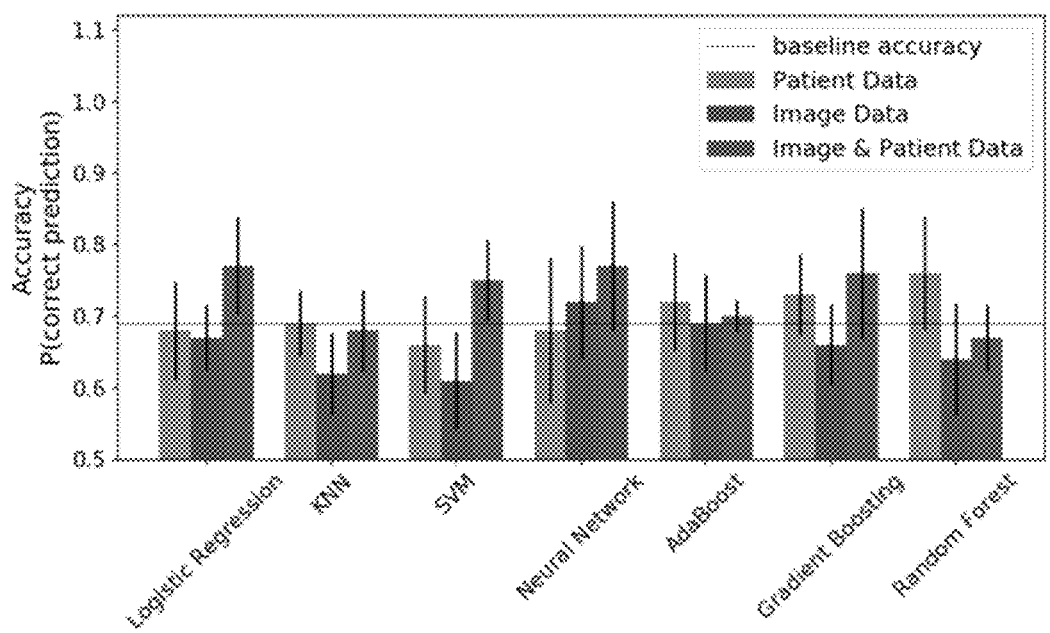
FIG. 31 is a bar graph illustrating the demonstrated accuracy of several example machine learning altorithms in accordance with the present technology.

Accuracy of predictions from the unsupervised feature extraction (autoencoder) and machine learning approach of FIGS. 28 and 29 were obtained using seven different machine learning algorithms and three different input feature combinations, as shown in FIG. 31. Each algorithm was trained using 3-fold cross validation and the average accuracy (±95% confidence interval) is reported. Only two algorithms trained in using this approach exceeded the baseline accuracy. The baseline accuracy occurred when a naive classifier simply predicted all DFUs as healing. The two algorithms that exceeded the baseline were logistic regression and support vector machines including a combination of both image data and patient data. The important patient health metrics that were predictive of the DFU healing and used to in these models included: wound area; body mass index (BMI); number of previous wounds; hemoglobin A1c (HbA1c); kidney failure; type II vs type I diabetes; anemia; asthma; drug use; smoking status; diabetic neuropathy; deep vein thrombosis (DVT); or previous myocardial infarction (MI) and combinations thereof.

Figure 30:
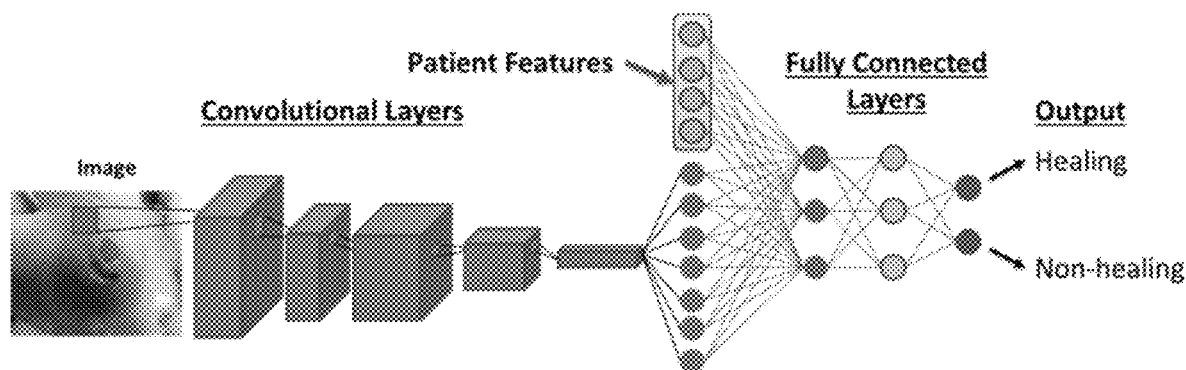
FIG. 30 schematically illustrates an example end-to-end machine learning algorithm in accordance with the machine learning systems and methods of the present technology.
Figure 32:
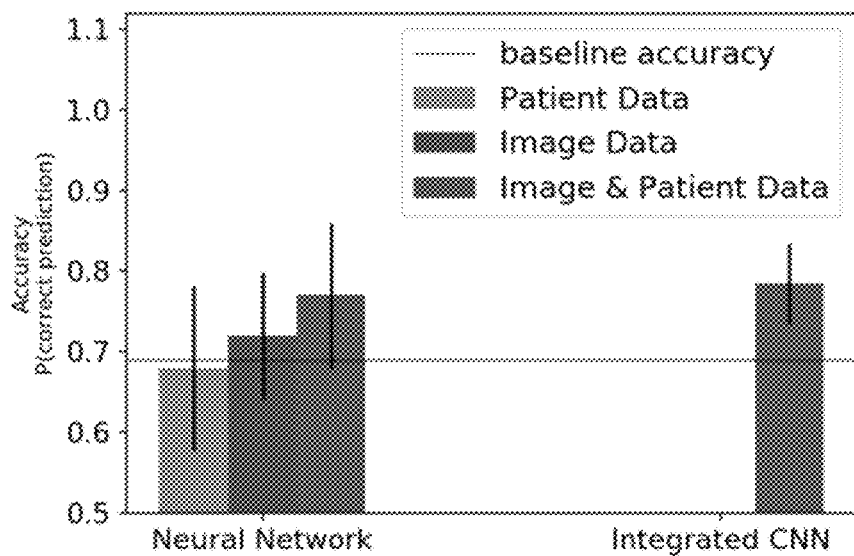
FIG. 32 is a bar graph illustrating the demonstrated accuracy of several example machine learning altorithms in accordance with the present technology.

Results using the end-to-end machine learning approach of FIG. 30 demonstrated performance that was significantly better than the baseline, as shown in FIG. 32. While this approach was not significantly better than the unsupervised approach, the average accuracy was higher than any other method attempted.

Prediction of Healing of a Subset of Wound Area

In further example embodiments, in addition to generating a single healing probability for an entire wound, the systems and methods of the present technology are further able to predict the area of tissue within an individual wound that will not be healed after 30 days of standard wound care. To accomplish this output, a machine learning algorithm was trained to take MSI or RGB data as input and generate predicted healing parameters for portions of the wound (e.g., for individual pixels or subsets of pixels in a wound image). The present technology can further be trained to output a visual representation such as an image that highlights the area of ulcer tissue that is not predicted to heal within 30 days.

Figure 33:
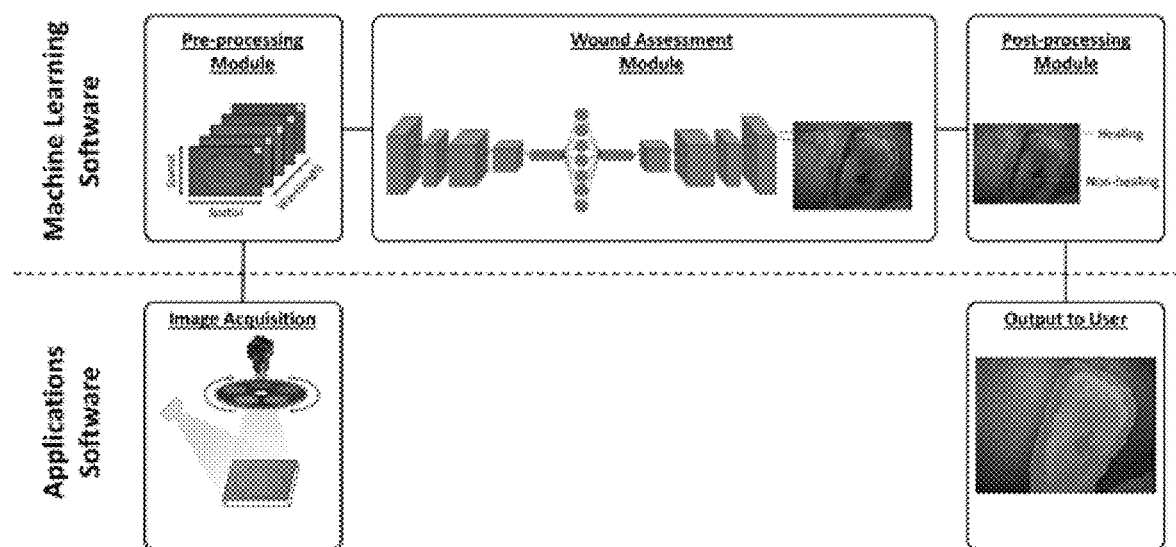
FIG. 33 schematically illustrates an example process of healing prediction and generation of a visual representation of a conditional probability mapping in accordance with the machine learning systems and methods of the present technology.

FIG. 33 illustrates an example process of healing prediction and generation of a visual representation. As shown in FIG. 33, a spectral data cube is obtained, as described elsewhere herein. This data cube is passed to the machine learning software for processing. Machine learning software can implement some or all of the following steps: pre-processing, a machine learning wound assessment model, and post-processing. The machine learning module outputs a conditional probability map that is processed by the post-processing module (e.g., thresholding of probabilities) to generate the results that can then be visually output to the user in the form of a classified image. As shown in the image output to the user in FIG. 33, the system can cause an image of the wound to be displayed to the user such that the healing pixels and the non-healing pixels are displayed in different visual representations.

The process of FIG. 33 was applied to a set of DFU images, and the predicted non-healing region was compared to the true non-healing region measured during a 30-day healing assessment conducted on the DFU. This comparison represents the performance of the algorithm. The method applied to perform this comparison was based on the clinical outcome of these output images. The database of DFU images contained 28 individual images of diabetic foot ulcers obtained from 19 subjects. For each image, the true area of wound that did not heal after 30 days of standard wound care was known. Algorithm training was conducted using the leave-one-out cross-validation (LOOCV) procedure. The results of each image were computed as one of True Positive, True Negative, False Positive, or False Negative. These results were summarized using the performance metrics described in Table 4 above.

A convolutional neural network was used to generate the conditional probability map for each input image. The algorithm includes an input layer, convolutional layers, deconvolutional layers, and output layer. The MSI or RGB data is typically input to a convolutional layer. The convolutional layer typically consists of a convolution stage (e.g., affine transformation) whose output is in turn used as input to a detector stage (e.g., nonlinear transformation such as rectified linear [ReLU]), the results of which may undergo further convolutions and detector stages. These results may be down sampled by a pooling function or be used directly as the results of the convolutional layer. The results of the convolution layer are provided as input to the next layer. The deconvolution layers typically begin with a reverse pooling layer followed by convolution and detector stages. Typically, these layers are organized in the order of input layer, convolution layers, and then deconvolution layers. This organization is often referred to having first the encoder layers followed by the decoder layers. The output layer typically consists of multiple fully connected neural networks applied to each vector across one of the dimensions of the tensor outputted from the previous layer. The aggregation of the results from these fully connected neural networks is a matrix called the conditional probability map.

Each entry in the conditional probability map represents a region of the original DFU image. This region may be a 1-to-1 mapping with the pixels in the input MSI image, or an n-to-1 mapping where n is some aggregation of pixels in the original image. The conditional probability values in this map represent the probability that the tissue in that area of the image will not respond to standard wound care. The result is a segmentation of the pixels in the original image wherein the predicted non-healing regions are segmented from the predicted healing regions.

Figure 34:
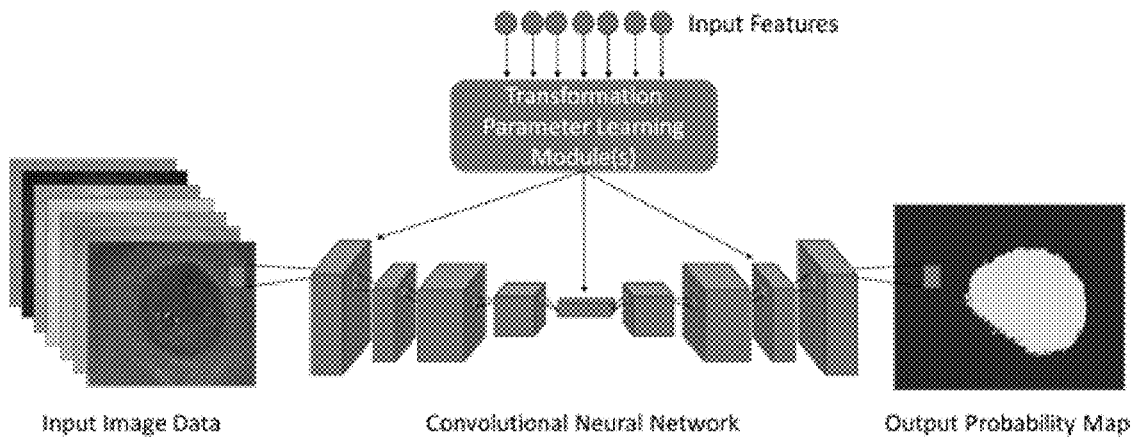
FIG. 34 schematically illustrates an example conditional probability mapping algorithm including one or more feature-wise linear transformation (FiLM) layers.

The results of a layer within the convolutional neural network can be modified by information from another source. In this example, clinical data from a subject's medical history or treatment plan (e.g., patient health metrics or clinical variables as described herein) can be used as the source of this modification. Thus, the results of the convolutional neural network can be conditioned on the level of a non-imaging variable. To do this, feature-wise linear transformation (FiLM) layers can be incorporated into the network architecture as shown in FIG. 34. The FiLM layer is a machine learning algorithm trained to learn the parameters of an affine transformation that is applied to one of the layers in the convolutional neural network. The input to this machine learning algorithm is a vector of values, in this case the clinically relevant patient medical history in the form of patient health metric values or clinical variables. The training of this machine learning algorithm may be accomplished simultaneously with the training of the convolutional neural network. One or more FiLM layers with varying inputs and machine learning algorithms can be applied to various layers of the convolutional neural network.

Input data for the conditional probability mapping included multispectral imaging (MSI) data and color photography images (RGB images). The MSI data consisted of 8 channels of 2D images, where each of the 8 channels represented the diffuse reflectance of light from the tissue at a specific wavelength filter. The field of view of each channel was 15 cm×20 cm with a resolution of 1044 pixels×1408 pixels. The 8 wavelengths included: 420 nm±20 nm, 525 nm±35 nm, 581 nm±20 nm, 620 nm±20 nm, 660 nm±20 nm, 726 nm±41 nm, 820 nm±20 nm, and 855 nm±30 nm, as illustrated in FIG. 26. The RGB images included 3 channels of 2D images, where each of the 3 channels represented the diffuse reflectance of light from the tissue at the wavelengths utilized in a traditional color camera sensor. The field of view of each channel was 15 cm×20 cm with a resolution of 1044 pixels×1408 pixels.

To perform image segmentation on the basis of healing probability, the CNN architecture called SegNet was used. This model was used as described by the original authors to take RGB images as input and output the conditional probability map. Additionally, it was modified to utilize the 8-channel MSI images in the input layer. Lastly, the SegNet architecture was modified to include a FiLM layer.

To demonstrate that the segmentation of DFU images into healing and non-healing regions can be accomplished, a variety of deep learning models were developed that each utilize different inputs. These models used the following two input feature categories: MSI data alone, and RGB images alone. In addition to varying the input features, a number of aspects of the algorithm training were varied. Some of these variations included pre-training the model with the PASCAL visual object classes (VOC) data set, pre-training the model with an image database of another type of tissue wound, pre-specifying the kernels of the input layer with a filter bank, early stopping, random image augmentations during algorithm training, and averaging the results of random image augmentations during inferencing to produce a single aggregated conditional probability map.

The top two performing models from each of the two feature input categories were identified to perform better than random chance. Results improved as RGB data was replaced with MSI data. The number of image-based errors reduced from 9 to 7. However, it was determined that both MSI and RGB methods are feasible for producing a conditional probability map for DFU healing potential.

Figure 35:
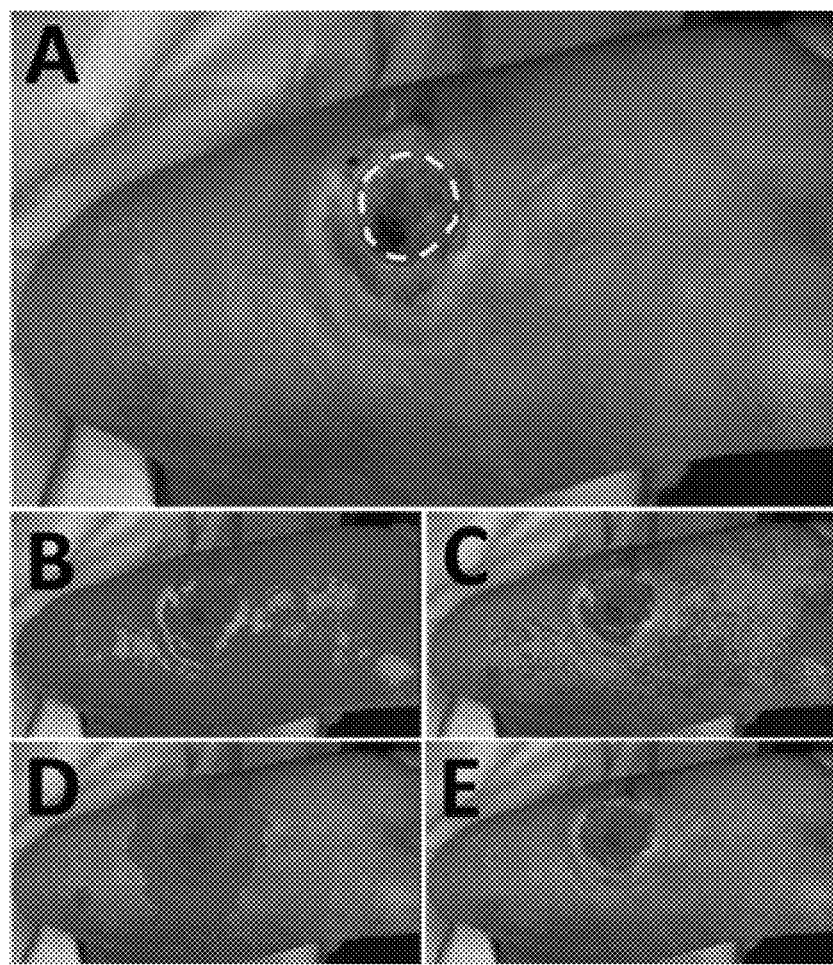
FIG. 35 illustrates the demonstrated accuracy of several image segmenation approaches for generating a conditional healing probability map in accordance with the present technology.

In addition to determining that a SegNet architecture can yield desirable segmentation accuracy for wound images, it was also determined that other types of wound images may be unexpectedly suitable for use in training systems to segment DFU images or other wound images on the basis of conditational probability mapping for healing. As described above, a SegNet CNN architecture may be suitable for DFU image segmentation when pre-trained using DFU image data as training data. However, in some cases a suitably large set of training images may not be available for certain types of wounds. FIG. 35 illustrates an example color DFU image (A), and four examples of segmentation of the DFU into predicted healing and non-healing regions by different segmentation algorithms. In image (A), which was captured on the day of initial assessment, the dashed line indicates the portion of the wound that was identified as non-healing in a subsequent assessment four weeks later. In images (B)-(E), each corresponding segmentation algorithm yields a section of predicted non-healing tissue indicated by shading. As shown in image (E), a SegNet algorithm, which was pre-trained using a burn image database rather than a DFU image database, nevertheless produced a highly accurate prediction of a non-healing tissue region that closely matches the contour of the dashed line in image (A) corresponding to an empirically determined non-healing area. In contrast, a naïve Bayes linear model trained with DFU image data (image (B)), a logistic regression model trained with DFU image data (image (C)), and a SegNet pre-trained using PACAL VOC data (image (D)) all showed inferior results, with each of images (B)-(D) indicating a much larger and inaccurately shaped area of non-healing tissue.

Example Individual Wavelength Analysis of DFU Images

In further example implementations, it has been found that the percent area reduction (PAR) of a wound at day 30, and/or segmentation in the form of a conditional probability map, can further be performed based on image data of a single wavelength band, rather than using MSI or RGB image data. To accomplish this method, a machine learning algorithm was trained to take features extracted from a single wavelength band image as input and output a scalar value representing the predicted PAR.

All images were obtained from subjects under an institutional review board (IRB) approved clinical study protocol. The dataset contained 28 individual images of diabetic foot ulcers obtained from 17 subjects. Each subject was imaged on their initial visit for treatment of the wounds. Wounds were at least 1.0 cm wide in their longest dimension. Only subjects prescribed standard wound care therapy were included in the study. To determine the true PAR after 30 days of treatment, a DFU healing assessment was performed by the clinician during a routine follow-up visit. In this healing assessment, an image of the wound was collected and compared to the image taken at day 0 to accurately quantify PAR.

Various machine learning algorithms, such as classifier ensembles or the like, may be used. Two machine learning algorithms for regression were employed in this analysis. One algorithm was a bagging ensemble of decision tree classifiers (bagged trees), and the second was a random forest ensemble. All features used for training the machine learning regression models were obtained from the DFU image obtained prior to treatment at the initial visit for the DFU included the study.

Eight grayscale images of each DFU were obtained from unique wavelengths in the visible and near-infrared spectrum. The field of view of each image was approximately 15 cm×20 cm with a resolution of 1044 pixels×1408 pixels. The eight unique wavelength were selected using a set of optical band-pass filters with the following wavelength bands: 420 nm±20 nm, 525 nm±35 nm, 581 nm±20 nm, 620 nm±20 nm, 660 nm±20 nm, 726 nm±41 nm, 820 nm±20 nm, and 855 nm±30 nm, as illustrated in FIG. 26.

Each raw 1044 pixels×1408 pixels image included, for each pixel, a reflectance intensity value for the pixel. Quantitative features were calculated based on the reflectance intensity values, including the first and second moments (e.g., mean and standard deviation) of the reflectance intensity values. In addition, the median was also computed.

Figure 36:
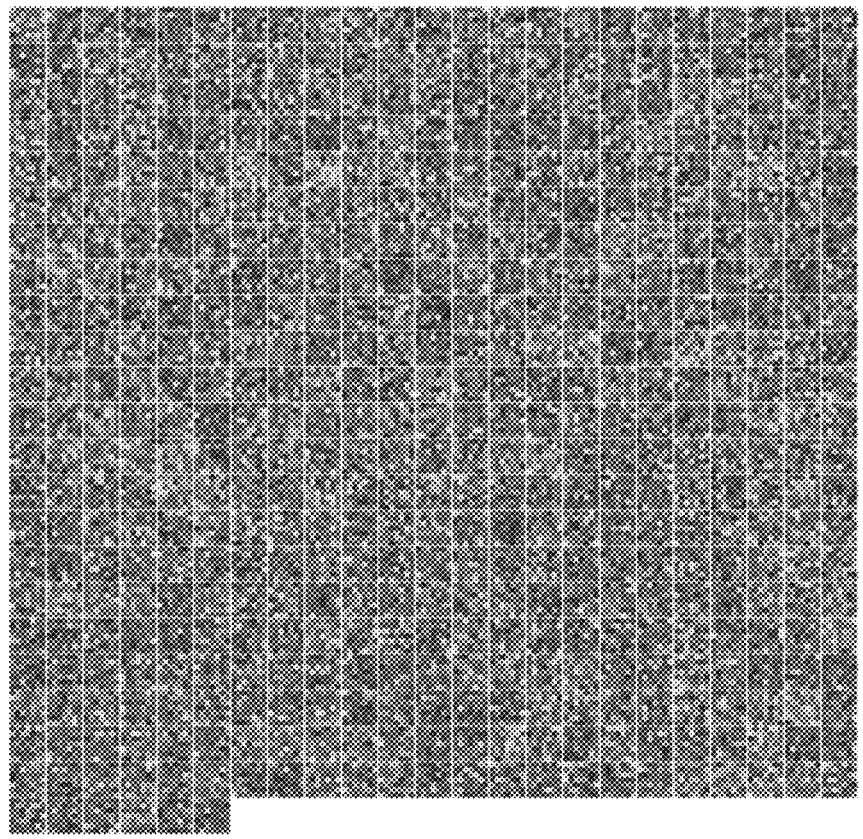
FIG. 36 illustrates an example set of convolutional filter kernels used in an example individual wavelength analysis method for healing prediction in accordance with the machine learning systems and methods of the present technology.

Following these computations, a set of filters can optionally be individually applied to the raw image to generate multiple image transformations. In one particular example, a total of 512 filters can be used, each having dimensions 7 pixels×7 pixels or another suitable kernel size. FIG. 36 illustrates an example set of 512 7×7 filter kernels that may be used in an example implementation. This non-limiting example set of filters can be obtained through the training of a convolutional neural network (CNN) for DFU segmentation. The 512 filters illustrated in FIG. 36 were obtained from the first set of kernels in the input layer of the CNN. The "learning" of these filters was regularized by constraining their weight updates to prevent large deviations to Gabor filters contained in a filter-bank.

Filters can be applied to the raw image by convolution. From the 512 images that result from these filter convolutions, a single 3D matrix may be constructed with dimensions 512 channels×1044 pixels×1408 pixels. Additional features may then be computed from this 3D matrix. For example, in some embodiments the mean, median, and standard deviation of the intensity values of the 3D matrix may be computed as further features for input into the machine learning algorithm.

In addition to the six features described above (e.g., mean, median, and standard deviation of pixel values of the raw image and of the 3D matrix constructed from the application of convolutional filters to the raw image), additional features and/or linear or non-linear combinations of such features may further be included as desired. For example, the product or the ratio of two features could be used as new input features to the algorithm. In one example, the product of a mean and a median may be used as an additional in put feature.

Algorithm training was conducted using the leave-one-out cross-validation (LOOCV) procedure. One DFU was selected for the test set and the remaining DFU images used as the training set. After training, the model was used to predict the percent area reduction for the held-out DFU image. Once this was done, the held-out image was returned to the full set of DFU images so that this process could be repeated with a different held-out image. LOOCV was repeated until each DFU image was part of the held-out set once. After accumulating test set results across every fold of cross-validation, the overall performance of the model was computed.

The predicted percent area reduction for each DFU image was compared to the true percent area reduction measured during a 30-day healing assessment conducted on the DFU. The performance of the algorithm was scored using coefficient of determination ($R^2$). The $R^2$ value was used to determine the utility of each individual wavelength, which is a measure of the proportion of the variance in DFU percent area reduction that was explained by the features extracted from the DFU image. The $R^2$ value is defined as:

$$R^2 = 1 - \frac{\Sigma_i(y_i - f(x_i))^2}{\Sigma_i(y_i - \overline{y})^2},$$

where $y_i$ is the true PAR for DFU i, $\overline{y}$ is the mean PAR across all DFUs in the data set, and $f(x_i)$ is the predicted PAR for DFU i. The 95% confidence interval of the $R^2$ value was computed from the prediction results of the algorithm trained on each feature set. The 95% CI was computed using the following equation:

$$R^2 \pm 2 * SE_{R^2},$$

where $$SE_{R^2} = \sqrt{\frac{4R^2(1 - R^2)^2(n - k - 1)^2}{(n^2 - 1)(n + 3)}}$$

In this equation n is the total number DFU images in the data set and k is the total number of predictors in the model.

The goal was to determine that each of the eight individual wavelengths could be used independently in a regression model to achieve results that were significantly better than random chance. To determine if a feature set could provide an improvement over random chance, feature sets were identified wherein zero was not contained within the 95% CI of $R^2$ for the algorithm trained on that feature set. To do this, eight separate experiments were conducted wherein models were trained with the following six original features: the mean, median, and standard deviation of the raw image; and the mean, median, and standard deviation of the 3D matrix generated from raw image transformations by application of the convolutional filters. The random forest and bagged trees models were trained. Results were reported for the algorithm with superior performance in cross-validation. The results of these eight models were reviewed to determine whether the lower-bound 95% CI was above zero. If not, the additional features generated by non-linear combinations of the six original features were employed.

Using the six original features, seven of the eight wavelengths examined could be used to generate regression models that explained a significant amount of the variance in percent area reduction from the DFU dataset. In order of most effective to least effective, the seven wavelengths were: 660 nm; 620 nm; 726 nm; 855 nm; 525 nm; 581 nm; and 420 nm. The final wavelength, 820 nm, was found to be significant if the product of mean and median of the 3D matrix was included as an additional feature. Results of these trials are summarized in Table 5.

TABLE 5

Results of regression models developed for the eight unique wavelength images

| Wavelength | $R^2$ | Lower 95% CI | Input Features | Algorithm | Algorithm Parameters |
|---|---|---|---|---|---|
| 660 | 0.410 | 0.210 | Original six | Random Forest | n_estimators = 1 |
| 620 | 0.340 | 0.137 | Original six | Random Forest | n_estimators = 1 |
| 726 | 0.270 | 0.060 | Original six | Bagged Trees | n_estimators = 1<br>max_features = 5<br>max_samples = 19 |
| 855 | 0.230 | 0.026 | Original six | Bagged Trees | n_estimators = 1<br>max_features = 5<br>max_samples = 15 |
| 525 | 0.210 | 0.010 | Original six | Bagged Trees | n_estimators = 1<br>max_features = 5<br>max_samples = 25 |
| 581 | 0.200 | 0.002 | Original six | Bagged Trees | n_estimators = 2<br>max_features = 5<br>max_samples = 24 |
| 420 | 0.190 | 0.003 | Original six | Random Forest | n_estimators = 2 |
| 820 | 0.183 | 0.007 | Original six, and the product of Mean(transformed) with Median(transformed) | Bagged Trees | n_estimators = 2<br>max_features = 7<br>max_samples = 5 |

Accordingly, it has been shown that the imaging and analysis systems and methods described herein may be able to accurately generate one or more predicted healing parameters based on even a single wavelength band image. In some embodiments, use of a single wavelength band may be facilitated the calculation of one or more aggregate quantitative features from the image, such as a mean, median, or standard deviation of raw image data and/or of a set of images or 3D matrix generated by application of one or more filters to the raw image data.

Example Wound Image Segmentation Systems and Methods

As described above, spectral images including reflectance data at an individual wavelength or a plurality of wavelengths can be analyzed using the machine learning techniques described herein, to reliably predict parameters associated with wound healing, such as overall wound healing (e.g., percent area reduction) and/or healing associated with portions of a wound (e.g., a healing probability associated with an individual pixel or subset of pixels of a wound image). Moreover, some of the methods disclosed herein predict wound healing parameters based at least in part on aggregate quantitative features, for example, statistical quanities such as means, standard deviations, median values, or the like, calculated based on a subset of pixels of a wound image that are determined to be the "wound pixels," or the pixels that correspond to the wound tissue region rather than callus, normal skin, background, or other non-wound tissue regions. Accordingly, in order to improve or optimize the accuracy of such predictions based on a set of wound pixels, it is preferable to accurately select the subset of wound pixels in an image of a wound.

Conventionally, segmentation of an image such as an image of a DFU into wound pixels and non-wound pixels has been performed manually, for example, by a doctor or other clinician who examines the image and selects the set of wound pixels based on the image. However, such manual segmentation may be time consuming, inefficient, and potentially prone to human error. For example, the formulas used to compute area and volume lack the accuracy and precision required to measure the convex shape of wounds. In addition, identifying the true boundaries of the wound and classification of tissues within the wound, such as epithelial growth, requires a high level of competency. Since changes in wound measurements are often the critical information used to determine treatment efficacy, errors in the initial wound measurements can result in incorrect treatment determinations.

To this end, systems and methods of the present technology are suitable for automated detection of wound margins and identification of tissue types in the wound area. In some embodiments, the systems and methods of the present technology can be configured for automated segmentation of wound images into at least wound pixels and non-wound pixels, such that any aggregate quantitiative features calculated based on the subset of wound pixels achieve a desirable level of accuracy. Moreover, it may be desirable to implement systems or methods capable of segmenting a wound image into wound and non-wound pixels, and/or into one or more sub-classes of wound or non-wound pixels, without necessarily further generating predicted healing parameters.

Figure 37:
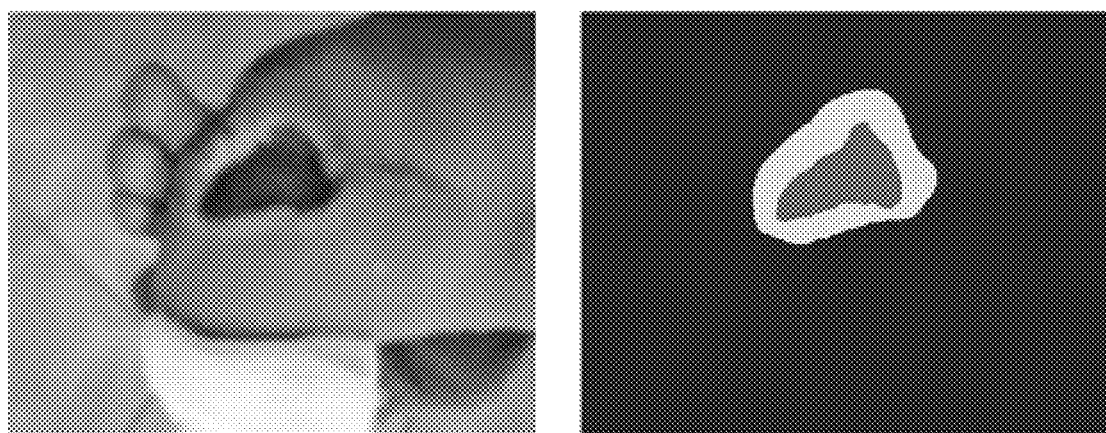
FIG. 37 illustrates an example ground truth mask generated based on a DFU image for image segmentation in accordance with the machine learning systems and methods of the present technology.

A dataset of diabetic foot ulcer images may be developed using color photographs of wounds. Various color camera systems can be used in the acquisition of this data. In one example implementation, 349 total images were used. A trained physician or other clinician may use a software program to identify and label the wound, callus, normal skin, background, and/or any other types of pixel categories in each wound image. The resulting labeled images, known as ground truth maks, may include a number of colors corresponding to the number of labeled categories in the image. FIG. 37 illustrates an example image of a DFU (left), and corresponding ground truth mask (right). The example ground truth mask of FIG. 37 includes a purple region corresponding to background pixels, a yellow region corresponding to callus pixels, and a cyan region corresponding to wound pixels.

Based on a set of ground truth images, a convolutional neural network (CNN) can be used for the automated segmentation of these tissue categories. In some embodiments, the algorithm structure can be a shallow U-net with a plurality of convolutional layers. In one example implementation, desirable segmentation outcomes were achieved with 31 convolutional layers. However, many other algorithms for image segmentation could be applied to achieve the desired output.

In the example segmentation implementation, the DFU image database was randomly split into three sets such that 269 training set images were used for algorithm training, 40 test set images for hyperparameter selection, and 40 validation set images for validation. The algorithm was trained with gradient descent and the accuracy of the test set images was monitored. The algorithm training was stopped when the test set accuracy was maximized. The results of this algorithm were then determined using the validation set.

Results from the U-net algorithm for each image in the validation set were compared to their corresponding ground truth mask. This comparison was done on a pixel-by-pixel basis. Within each of the three tissue types this comparison was summarized using the following categories. A True Positive (TP) category included the total number of pixels for which the tissue type of interest was present at a pixel in the ground truth mask, and the model predicted the tissue type was present at this pixel. A True Negative (TN) category included the total number of pixels for which the tissue type of interest was not present at a pixel in the ground truth mask, and the model predicted the tissue type was not present at this pixel. A False Positive (FP) category included he total number of pixels for which the tissue type of interest was not present at a pixel in the ground truth mask, and the model predicted the tissue type was present at this pixel. A False Negative (FN) category included the total number of pixels for which the tissue type of interest was present at a pixel in the ground truth mask, and the model predicted the tissue type was not present at this pixel. These results were summarized using the following metrics:

Accuracy:

$$Acc_{model} = \frac{1}{N} \sum_{i=1}^{N} [TP_{wound} + TP_{callus} + TP_{uninjured}] + [TN_{wound} + TN_{callus} + TN_{uninjured}],$$

where N is the total number of pixels in the validation set.

Average dice score:

$$AveDSC_{model} = \frac{1}{C} \sum_{j=1}^{C} \frac{2TP_j}{2TP_j + FP_j + FN_j},$$

where C represents the three tissue types.

Average intersection over union (IOU):

$$AveDSC_{model} = \frac{1}{C} \sum_{j=1}^{C} \frac{TP_j}{TP_j + FP_j + FN_j},$$

where C represents the three tissue types.

In some embodiments, algorithm training may be conducted over a plurality of epochs, and an intermediate number of epochs may be determined at which accuracy is optimized. In the example implementation described herein, algorithm training for image segmentation was conducted over 80 epochs. As training was monitored, it was determined that epoch 73 achieved the best accuracy for test dataset.

The performance of the U-net segmentation algorithm was computed with the accuracy being better than random chance. U-net also outperformed all three possible naïve approaches, where a naïve classifier is used to always predict one tissue class. Regardless of the potential overfitting issue, the model performance on the validation set was able to demonstrate feasibility based on these summary metrics.

Figure 38:
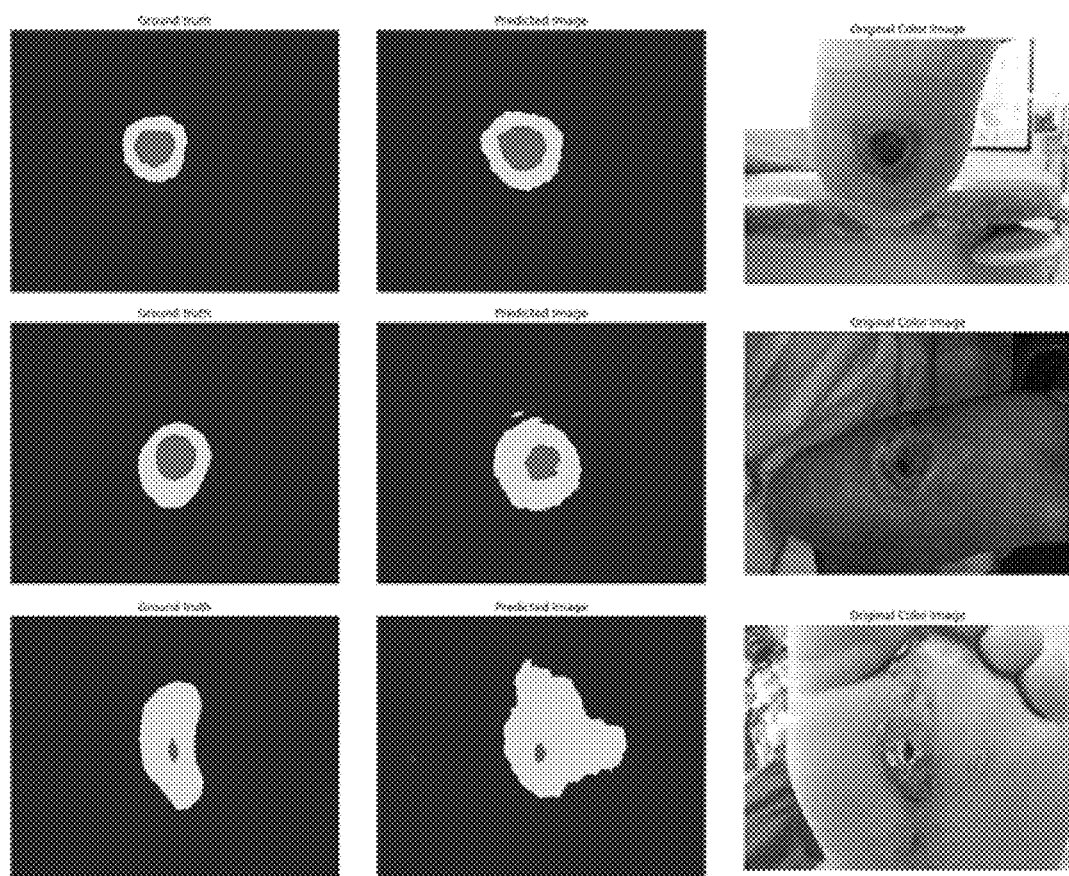
FIG. 38 illustrates the demonstrated accuracy of an example wound image segmentation algorithm in accordance with the machine learning systems and methods of the present technology.

FIG. 38 illustrates three example results of wound image segmentation using the U-net segmentation algorithm in combination with the methods described herein. For each of the three example DFU images in the right column, the U-net segmentation algorithm, trained as described herein, generated the automated image segmentation outputs shown in the middle column. The manually generated ground truth masks corresponding to each DFU image are shown in the left column of FIG. 38, visually illustrating the high segmentation accuracy that can be obtained using the methods described herein.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The disclosed processes may begin in response to an event, such as on a predetermined or dynamically determined schedule, on demand when initiated by a user or system administer, or in response to some other event. When the process is initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, the process or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multithreaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the scope of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A system for assessing or predicting wound healing, the system comprising:
   at least one light detection element configured to collect light of at least a first wavelength after being reflected from a tissue region comprising a diabetic foot ulcer; and
   one or more processors in communication with the at least one light detection element and configured to:
      receive a signal from the at least one light detection element, the signal representing light of the first wavelength reflected from the tissue region;
      generate, based on the signal, an image having a plurality of pixels depicting the tissue region;
      determine, based on the signal, a reflectance intensity value at the first wavelength for each pixel of at least a subset of the plurality of pixels;
      determine one or more quantitative features of the subset of the plurality of pixels based on the reflectance intensity values of each pixel of the subset; and
      generate, using one or more machine learning algorithms, at least one scalar value based on the one or more quantitative features of the subset of the plurality of pixels, the at least one scalar value corresponding to a predicted amount of healing of the diabetic foot ulcer over a predetermined time interval following generation of the image.

2. The system of claim 1, wherein the predicted amount of healing is a predicted percent area reduction of the diabetic foot ulcer.

3. The system of claim 1, wherein the predetermined time interval is 30 days.

4. The system of claim 1, wherein the one or more processors are further configured to identify at least one patient health metric value corresponding to a patient having the tissue region, and wherein the at least one scalar value is generated based on the one or more quantitative features of the subset of the plurality of pixels and on the at least one patient health metric value.

5. The system of claim 4, wherein the at least one patient health metric value comprises at least one variable selected from the group consisting of demographic variables, diabetic foot ulcer history variables, compliance variables, endocrine variables, cardiovascular variables, musculoskeletal variables, nutrition variables, infectious disease variables, renal variables, obstetrics or gynecology variables, drug use variables, other disease variables, or laboratory values.

6. The system of claim 4, wherein the at least one patient health metric value comprises at least one feature selected from the group consisting of an age of the patient, a level of chronic kidney disease of the patient, a length of the diabetic foot ulcer on a day when the image is generated, and a width of the diabetic foot ulcer on the day when the image is generated.

7. The system of claim 1, wherein the first wavelength is within the range of 620 nm±20 nm, 660 nm±20 nm, or 420 nm±20 nm, and wherein the one or more machine learning algorithms comprise a random forest ensemble.

8. The system of claim 1, wherein the first wavelength is within the range of 726 nm±41 nm, 855 nm±30 nm, 525 nm±35 nm, 581 nm±20 nm, or 820 nm±20 nm, and wherein the one or more machine learning algorithms comprise an ensemble of classifiers.

9. The system of claim 1, wherein the one or more processors are further configured to:
   automatically segment the plurality of pixels of the image into wound pixels and non-wound pixels; and
   select the subset of the plurality of pixels to comprise the wound pixels.

10. The system of claim 9, wherein the one or more processors automatically segment the plurality of pixels using a segmentation algorithm comprising at least one of a U-Net comprising a plurality of convolutional layers and a SegNet comprising a plurality of convolutional layers.

11. The system of claim 1, wherein the one or more quantitative features of the subset of the plurality of pixels are selected from the group consisting of a mean of the reflectance intensity values of the pixels of the subset, a standard deviation of the reflectance intensity values of the pixels of the subset, and a median reflectance intensity value of the pixels of the subset.

12. The system of claim 1, wherein the one or more processors are further configured to:
   individually apply a plurality of filter kernels to the image by convolution to generate a plurality of image transformations;
   construct a 3D matrix from the plurality of image transformations; and
   determine one or more quantitative features of the 3D matrix, wherein the at least one scalar value is generated based on the one or more quantitative features of the subset of the plurality of pixels and on the one or more quantitative features of the 3D matrix.

13. The system of claim 12, wherein the one or more quantitative features of the 3D matrix are selected from the group consisting of a mean of the values of the 3D matrix, a standard deviation of the values of the 3D matrix, a median value of the 3D matrix, and a product of the mean and the median of the 3D matrix.

14. The system of claim 13, wherein the at least one scalar value is generated based on the mean of the reflectance intensity values of the pixels of the subset, the standard deviation of the reflectance intensity values of the pixels of the subset, the median reflectance intensity value of the pixels of the subset, the mean of the values of the 3D matrix, the standard deviation of the values of the 3D matrix, and the median value of the 3D matrix.

15. The system of claim 1, wherein the at least one light detection element is further configured to collect light of at least a second wavelength after being reflected from the tissue region, and wherein the one or more processors are further configured to:
   receive a second signal from the at least one light detection element, the second signal representing light of the second wavelength reflected from the tissue region;
   determine, based on the second signal, a reflectance intensity value at the second wavelength for each pixel of at least the subset of the plurality of pixels; and
   determine one or more additional quantitative features of the subset of the plurality of pixels based on the reflectance intensity values of each pixel at the second wavelength;
   wherein the at least one scalar value is generated based at least in part on the one or more additional quantitative features of the subset of the plurality of pixels.

16. A method of predicting wound healing using the system of claim 1, the method comprising:
   illuminating the tissue region with illumination light of at least the first wavelength such that the tissue region reflects at least a portion of the illumination light to the at least one light detection element;
   using the system to generate the at least one scalar value; and
   determining the predicted amount of healing over the predetermined time interval.

17. The method of claim 16, wherein the one or more processors generate the at least one scalar value on a same day as a beginning of the predetermined time interval.

18. The method of claim 16, further comprising:
   measuring one or more dimensions of the diabetic foot ulcer after the predetermined time interval has elapsed following the determination of the predicted amount of healing of the diabetic foot ulcer;
   determining an actual amount of healing of the diabetic foot ulcer over the predetermined time interval; and
   updating at least one machine learning algorithm of the one or more machine learning algorithms by providing at least the image and the actual amount of healing of the diabetic foot ulcer as training data.

19. The method of claim 16, further comprising selecting, prior to an end of the predetermined time interval, between a standard wound care therapy and an advanced wound care therapy based at least in part on the predicted amount of healing of the diabetic foot ulcer.

20. The method of claim 19, wherein selecting between the standard wound care therapy and the advanced wound care therapy comprises:
   when the predicted amount of healing indicates that the diabetic foot ulcer will heal or close by greater than 50% in 30 days, indicating or applying one or more standard therapies selected from the group consisting of optimization of nutritional status, debridement by any means to remove devitalized tissue, maintenance of a clean moist bed of granulation tissue with appropriate moist dressings, necessary therapy to resolve any infection that may be present, addressing any deficiencies in vascular perfusion to an extremity comprising the diabetic foot ulcer, offloading of pressure from the diabetic foot ulcer, and appropriate glucose control; and when the predicted amount of healing indicates that the diabetic foot ulcer will not heal or close by greater than 50% in 30 days, indicating or applying one or more advanced care therapies selected from the group consisting of hyperbaric oxygen therapy, negative-pressure wound therapy, bioengineered skin substitutes, synthetic growth factors, extracellular matrix proteins, matrix metalloproteinase modulators, and electrical stimulation therapy.

* * * * *